US 12,156,972 B2

(12) United States Patent
Bryant

(10) Patent No.: US 12,156,972 B2
(45) Date of Patent: Dec. 3, 2024

(54) INTERMITTENT CATHETER

(71) Applicant: ConvaTec Limited, Flintshire (GB)

(72) Inventor: Jason Bryant, Erie, PA (US)

(73) Assignee: CONVATEC LIMITED, Flintshire (GB)

( * ) Notice: Subject to any disclaimer, the term of this patent is extended or adjusted under 35 U.S.C. 154(b) by 0 days.

(21) Appl. No.: 18/492,009

(22) Filed: Oct. 23, 2023

(65) Prior Publication Data

US 2024/0050691 A1 Feb. 15, 2024

Related U.S. Application Data

(63) Continuation of application No. PCT/GB2022/051013, filed on Apr. 22, 2022.

(30) Foreign Application Priority Data

Apr. 23, 2021 (GB) ..................................... 2105821

(51) Int. Cl.
*A61M 25/00* (2006.01)
*A61M 25/01* (2006.01)

(52) U.S. Cl.
CPC ...... *A61M 25/0017* (2013.01); *A61M 25/002* (2013.01); *A61M 25/0045* (2013.01); *A61M 25/0113* (2013.01); *A61M 2025/0046* (2013.01)

(58) Field of Classification Search
CPC ............ A61M 25/002; A61M 25/0111; A61M 25/0017; A61M 2025/0046; A61M 2210/1089; A61M 2210/1096; A61M 2210/1092; A61M 25/0113
See application file for complete search history.

(56) References Cited

U.S. PATENT DOCUMENTS

| | | | |
|---|---|---|---|
| 10,912,918 B1 | 2/2021 | Palmer | |
| 2005/0197627 A1* | 9/2005 | Huang | A61M 25/00 604/171 |
| 2006/0163097 A1* | 7/2006 | Murray | B65B 7/02 206/364 |
| 2007/0225649 A1 | 9/2007 | House | |
| 2011/0114520 A1* | 5/2011 | Matthison-Hansen | A61M 25/0111 206/364 |

(Continued)

FOREIGN PATENT DOCUMENTS

| | | |
|---|---|---|
| WO | 2007050685 A2 | 5/2007 |
| WO | 2019014344 A1 | 1/2019 |

OTHER PUBLICATIONS

International Preliminary Report on Patentability; International Application No. PCT/GB2022/051013; dated Jul. 3, 2023; 8 pages.

*Primary Examiner* — Adam Marcetich
(74) *Attorney, Agent, or Firm* — TAFT STETTINIUS HOLLISTER LLP; Ryan O. White; Derek B. Lavender

(57) ABSTRACT

An intermittent catheter, preferably a female intermittent catheter, is provided in an assembly. The assembly may include a cap which may be attachable to the base of the assembly in use, and/or a seal which misaligns with sealing surfaces of a chamber wall and a moveable insert in use. It may have a two-step deployment, and/or a sheath that pulls out a storage chamber. Internal and external housing may define the storage chamber. The housing may have a filling aperture and/or the storage chamber may comprise an insert configured to move axially in response to rotation.

20 Claims, 17 Drawing Sheets

(56) References Cited

U.S. PATENT DOCUMENTS

| | | | |
|---|---|---|---|
| 2012/0110951 A1* | 5/2012 | van Groningen | A61M 25/0111 53/425 |
| 2016/0038717 A1* | 2/2016 | Murray | A61M 25/0111 604/544 |
| 2017/0056622 A1* | 3/2017 | O'Flynn | A61M 25/0017 |
| 2017/0296776 A1* | 10/2017 | Palmer | A61M 25/0017 |
| 2019/0126004 A1* | 5/2019 | O'Brien | A61M 25/002 |
| 2020/0222659 A1* | 7/2020 | Schertiger | A61M 25/0111 |
| 2020/0230349 A1* | 7/2020 | McMenamin | B65D 43/162 |
| 2020/0391002 A1* | 12/2020 | Hilton | A61M 39/10 |
| 2021/0100979 A1* | 4/2021 | Donnelly | A61M 25/0067 |
| 2021/0170140 A1* | 6/2021 | Owen | A61M 25/002 |
| 2022/0387673 A1* | 12/2022 | Farrell | A61L 29/16 |
| 2023/0173246 A1* | 6/2023 | Takiguchi | A61M 39/20 604/544 |

\* cited by examiner

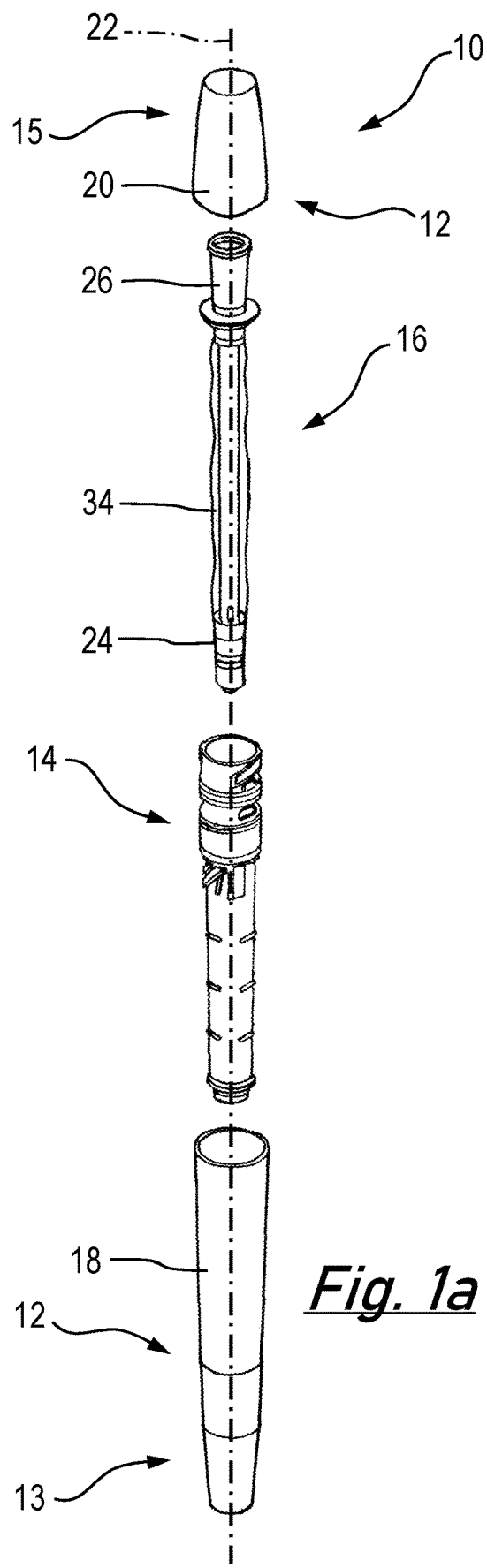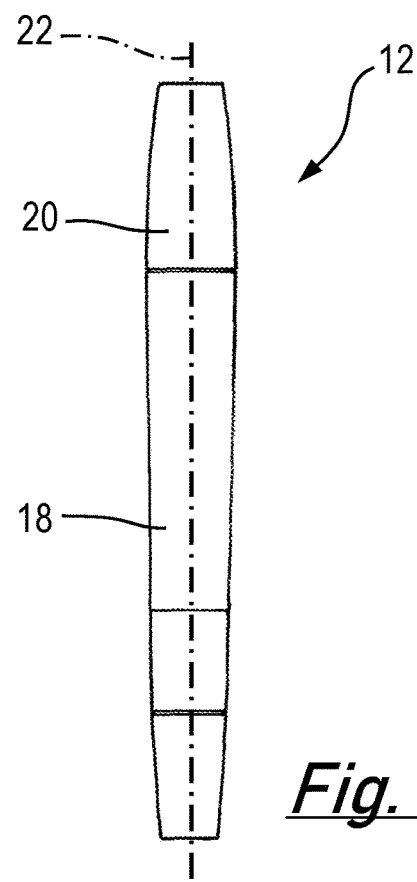
*Fig. 1a*
*Fig. 1b*

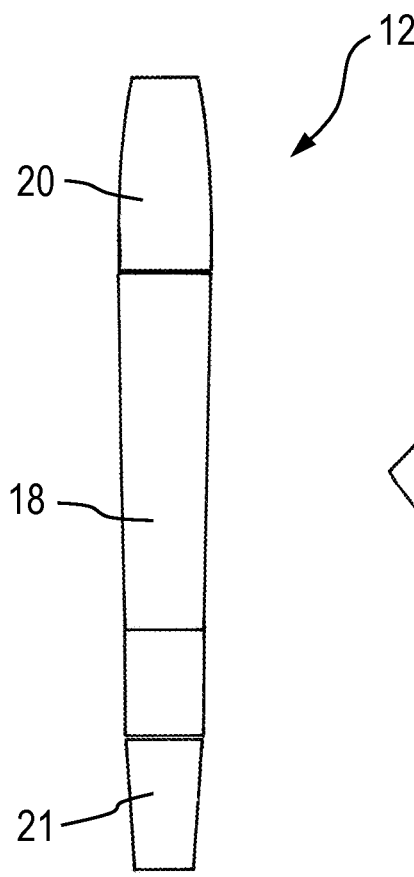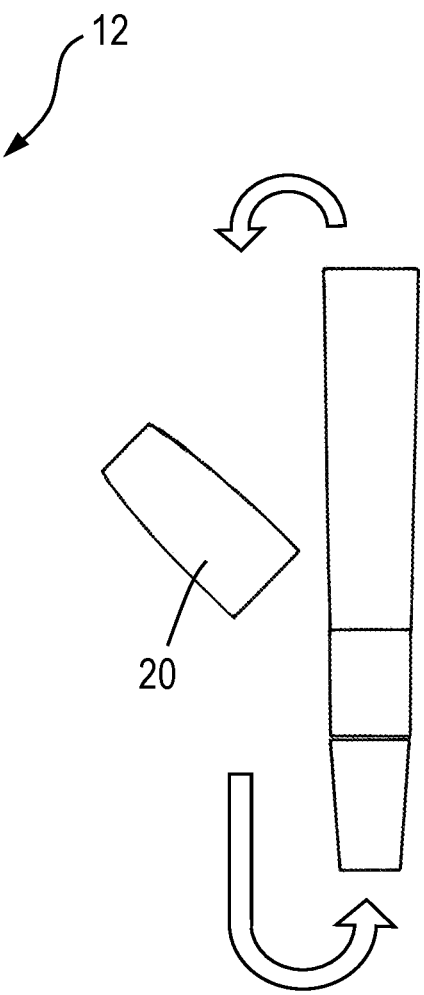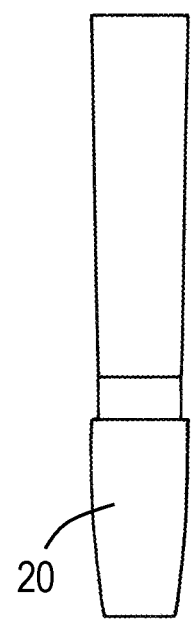
*Fig. 2a*  *Fig. 2b*  *Fig. 2c*

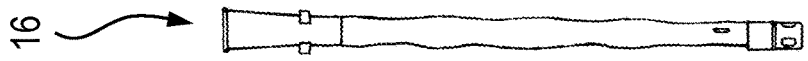
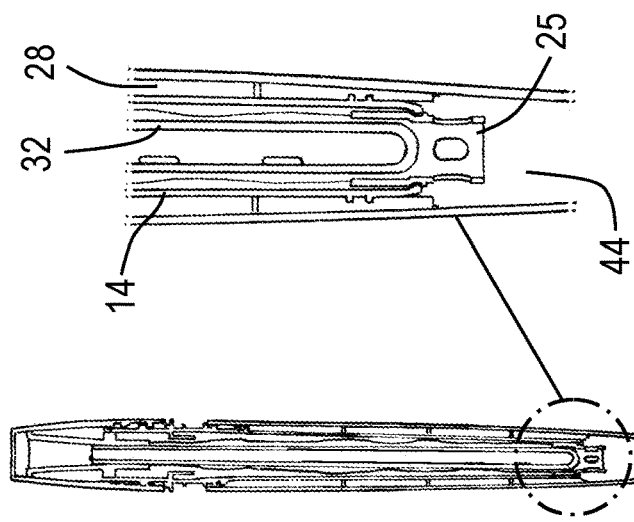
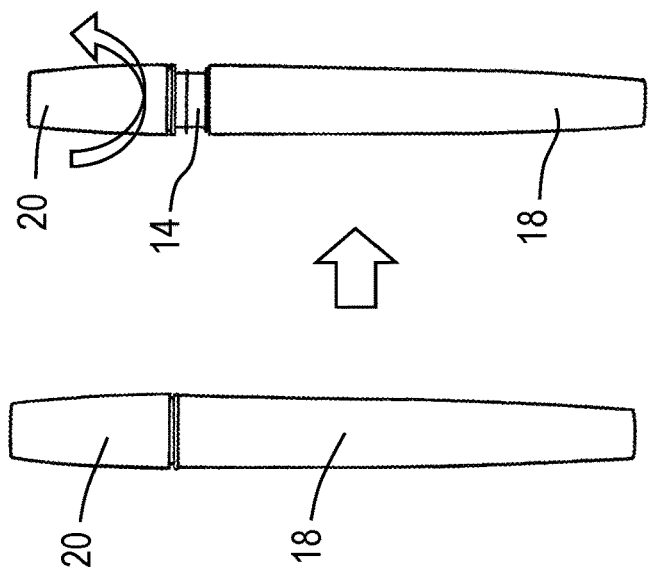

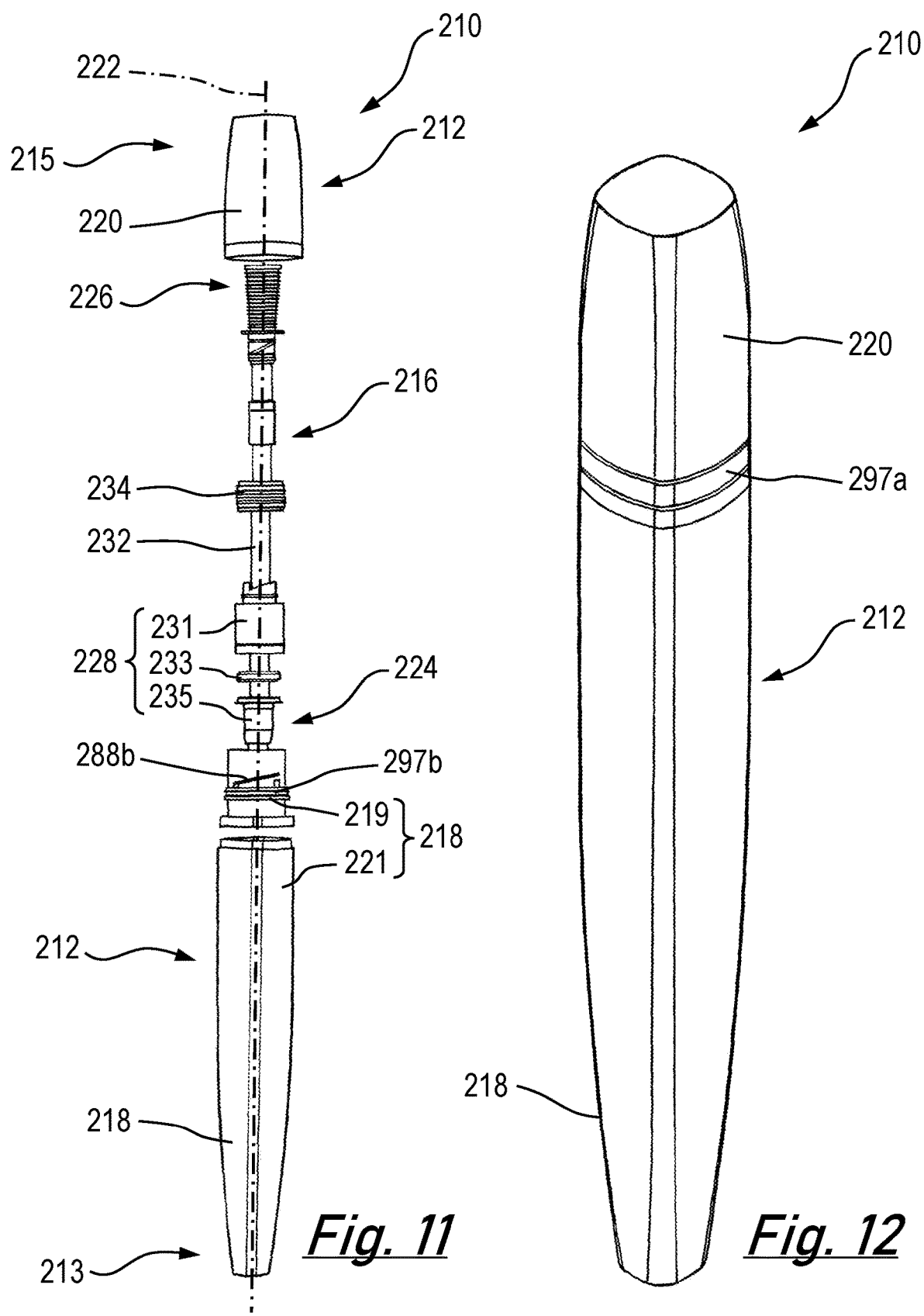

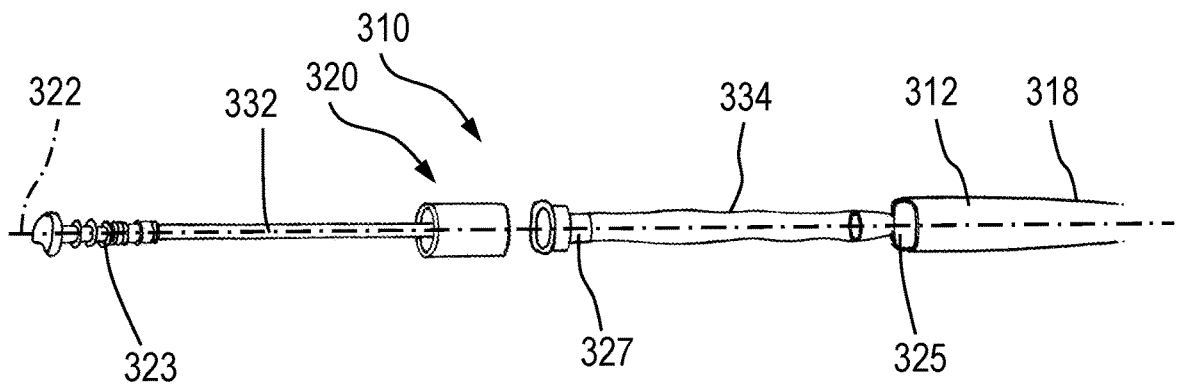
*Fig. 20*
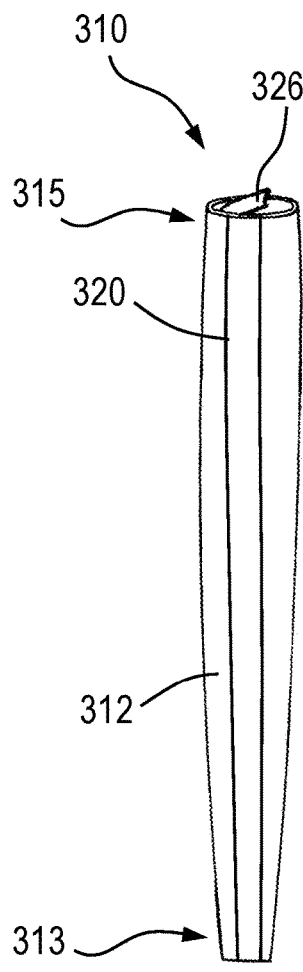
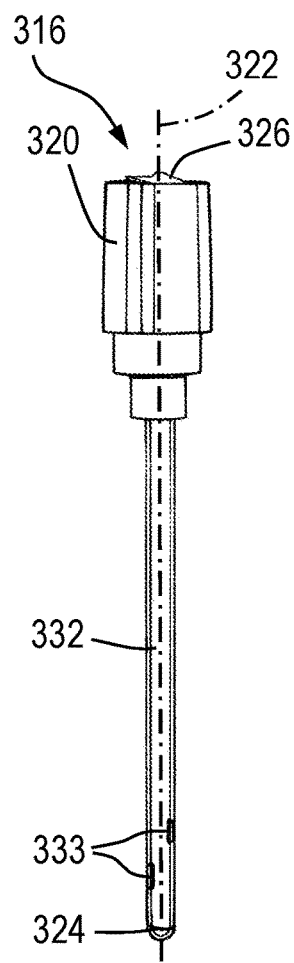
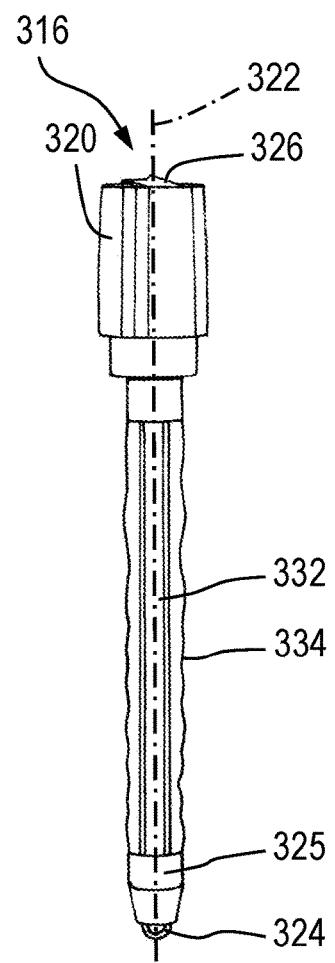
*Fig. 21a*   *Fig. 21b*   *Fig. 21c*

INTERMITTENT CATHETER

TECHNICAL FIELD OF THE INVENTION

The present invention relates to an intermittent catheter (e.g. a urinary catheter).

BACKGROUND TO THE INVENTION

A catheter is a medical device comprising a hollow catheter tube designed for insertion into canals, vessels, passageways or body cavities to permit injection, drainage or withdrawal of fluids or substances therefrom, or to ensure said canals, vessels, passageways etc. remain open. Urinary catheters are designed for use for insertion into a user's bladder via the urethra to drain the bladder.

To maximise comfort and minimise the risk of trauma and/or infection, an outer surface of the catheter tube is typically wetted using a wetting agent prior to insertion by the user. In further developments, the catheter tube itself comprises, is integrated with or is coated with a hydrophilic component (e.g. a hydrophilic polymer) which serves to reduce friction further upon application of the wetting agent.

Some catheters may be supplied pre-wetted in a packaging, for instance, where the catheter is at least partially submerged within wetting agent within the packaging. Whilst this may ensure the catheter tube is adequately wetted prior to use, such arrangements suffer in that components of the catheter other than the catheter tube such as a gripper element or funnel can also become wetted. This has a detrimental effect of the experience of the user where it may become difficult to hold and direct the catheter tube as required. This is particularly problematic where the user is performing self-catheterisation. Further, having the catheter submerged may effectively reduce the shelf-life of the catheter due to long-term exposure of components of the catheter to moisture.

It is therefore seen advantageous to provide a catheter which may be wetted at or immediately prior to the point of use.

In an attempt to address this, some catheters are provided in packaging which includes a rupturable container or sachet within the packaging which a user may burst to release the wetting agent. Typically, this involves the user squeezing the packaging to cause the container/sachet to break. However, such arrangements experience similar problems to those discussed above where the wetting agent is allowed to come into contact with other components of the catheter. Such arrangements also result in the possibility of the catheter tube not being fully wetted, or indeed wetted at all, prior to use. This can be harmful for the user.

It is therefore advantageous to provide a catheter which includes a means of supplying a wetting agent solely to the catheter tube to improve user experience.

In further prior art solutions, the catheter may be packaged within a packaging which includes a wetting device. In use, the catheter tube may be moved through the wetting device as the catheter is removed from the packaging and in doing so wetting the catheter tube. Examples of such catheters are shown in PCT application No. PCT/IB2018/001539 in the name of ConvaTec Limited.

However, due to packaging constraints the amount of wetting agent able to be contained in such wetting devices is low, and there therefore remains a possibility of the catheter tube not being fully wetted in such solutions, especially where the catheter is near the end of its shelf life and some of the solution may have evaporated.

For mechanisms which wet the catheter tube from the distal end, an insufficient volume of wetting agent may result in the tip end not being wetted at all which is undesirable since the tip end will be introduced into the urethra first and is hence most likely to cause injury if inadequately wetted before use.

Further a minimum length of catheter is required for regulatory approval and it is desirable to ensure that the length is wetted with a minimum impact on the packaging size.

It is an aim of an embodiment or embodiments of the invention to overcome or at least partially mitigate one or more problems with the prior art and/or to provide an improved intermittent catheter.

SUMMARY OF THE INVENTION

The present invention provides a catheter assembly according to the appended claims.

An aspect of the present disclosure provides a catheter assembly comprising: an external housing comprising a main body and a cap. The main body and cap may form a sterile cavity for housing a catheter. The catheter may be configured to be removed from the external housing in use. The main body may be elongate with an open end and a closed end. The cap and the closed end of the main body may comprise corresponding mating surfaces such that the cap is mountable on the closed end of the main body.

An aspect of the invention provides a catheter assembly comprising: an external housing comprising a main body and a cap, wherein the main body and cap form a sterile cavity for housing a catheter which is configured to be removed from the external housing in use; wherein the main body is elongate with an open end and a closed end; and, wherein the cap and the closed end of the main body comprise corresponding mating surfaces such that the cap is mountable on the closed end of the main body.

Providing a cap which is mountable on the closed end of the main body provides a convenient location to store the cap whilst the catheter is being used.

The cap may be configured to be mounted to the closed end of the case during use of the catheter. Thus, in use, the cap may be removed from the main body to expose the catheter for withdrawal from the external housing and placed on the closed end of the main body. The cap may be retained on the closed end of the main body whilst the catheter is being used. Following use, the catheter may be placed back within the main body and the cap replaced so as to house the catheter for disposal.

The temporary mounting of the cap to the main body may be resilient enough to withstand an amount of handling which might reasonably be expected whilst the catheter is removed and used. For example, the external housing may be temporarily placed on a surface whilst the catheter is used.

The mating surfaces may be any which allow the cap to be retainably mounted on the closed end of the main body. The mating surfaces may be provided by an internal surface of the cap and an external surface of the main body.

The internal surface of the cap may comprise one radial projections. The one or more radial projections may be ribs, or may be pips, pins, fins, or the like. The ribs may be longitudinally extending. The radial projections may provide at least part of the mating surface. The radial projections may mate with the external surface of the main body when the cap is mounted on the main body. The radial projections may be arranged to engage with a catheter within the external housing when the cap and the body form the sterile cavity. The radial projections may be arranged to rotate the catheter when the cap is being removed from the main body.

One or both of the mating surfaces may comprise an overmoulded element. The overmoulded element may comprise a layer, ring or insert arranged on the internal surface of the cap. The overmoulded element may comprise a layer, ring or projection arranged on the external surface of the main body. The overmoulded element may be comprised of softer material than the corresponding mating surface (that is, an overmoulded element arranged on the internal surface of the cap may be comprised of a material softer than the main body, or alternatively, an overmoulded element arranged on the external surface of the main body may be comprised of a material softer than the cap).

The mating surfaces may engage via an interference fit. The interference fit may be provided by a suitably large contacting area between the mating surfaces to allow for a frictional engagement suitable for retaining the cap on the main body. The interference fit may be referred to as a resistance fit.

The profiles of an internal surface of the cap and the external surfaces of the main body may correspond to one another. The mating surfaces may comprise corresponding tapered profiles. The tapered profiles may be uniformly tapered such that the angle of the taper is constant along its length.

The external housing may be suitable for an intermittent catheter. The catheter may be a female intermittent catheter. The catheter may have a length of between 90 mm to 200 mm. The catheter may have a length of between 100 mm and 150 mm or for example between 130 mm and 155 mm, such as about 135 mm. The catheter assembly may have a length corresponding to the length of the catheter. For example, the length of the catheter assembly, i.e. the closed length of the casing may be between 2 mm and 20 mm, for example between 2 mm and 15 mm, such as between 2 mm and 10 mm longer than the length of catheter The catheter assembly (when closed) may have a length of 10 and 25 cm; it may have a length of between 11 and 16 cm, for example, between 140 mm and 165 mm, such as 142 mm.

The external housing may be suitable for a catheter assembly. The external housing may be manufactured, imported and sold independently of the catheter. The catheter assembly may comprise a catheter.

The main body and/or cap may be rigid. The rigidity of the main body and cap may be configured to be resiliently deformable to aid the interference fit of the cap on the closed end of the main body.

The external housing may be comprised of plastic. The external housing may be comprised of thermoplastic. The cap and main body may be comprised of different materials. The external housing (optionally the cap or main body) may be comprised of polycarbonate; the external housing (optionally the cap or main body) may be comprised of polyethylene; the external housing (optionally the cap or main body) may be comprised of nylon. Preferably the external housing (optionally the cap or main body) may be comprised of polypropylene.

In one aspect, the present disclosure may provide a method of using a catheter assembly comprising an external housing comprising a cap and a main body. The main body may have a first end to which the cap is sealably attached prior to use and a second end. The method may comprise the steps of: removing the cap from a first end of the main body to expose the catheter for use, and mounting the cap on the second end of the main body. The method may further comprise inverting the cap prior to mounting it to the second end of the main body. The method may further comprise removing the catheter from the main body following (or prior to) mounting the cap on the second end of the main body. The method may further comprise replacing the catheter within the main body following the removal of the catheter from the main body. The method may further comprise dismounting the cap from the second end of the main body and replacing the cap on the first end of the main body. The method may comprise the step of twisting the cap to unscrew it from the main body. The step of twisting the cap may rotate the catheter in the assembly. The catheter may be rotated by radial projections on the cap, which may engage with the catheter, e.g. with corresponding radial projections of the catheter. The radial projections on the cap may further engage with the second end of the main body when the cap is mounted on the second end of the main body.

An aspect of the present disclosure provides a catheter assembly having a longitudinal axis. The catheter assembly may comprise: a catheter and a wetting agent storage chamber. The wetting agent storage chamber may comprise a chamber wall and a movable insert. The movable insert may be configured to move axially along the longitudinal axis with respect to the chamber wall between a first position and a second position.

The first position may correspond to a sealed configuration in which the storage chamber is sealed by a seal element. The seal element may be between the chamber wall and the movable insert. The seal element may be configured to align with sealing surfaces of the chamber wall and the movable insert in the first position.

The second position may be a position in which the seal is configured to be axially misaligned with at least one of the sealing surfaces.

An aspect of the present disclosure provides a catheter assembly having a longitudinal axis, the catheter assembly comprising: a catheter; and, a wetting agent storage chamber, the wetting agent storage chamber comprising a chamber wall and a movable insert, wherein the movable insert is configured to move axially along the longitudinal axis with respect to the chamber wall between a first position and a second position, wherein in the first position the storage chamber is sealed by a seal element located between the chamber wall and the movable insert; and, wherein the seal element is configured to align with sealing surfaces of the chamber wall and the movable insert in the first position; and, wherein in the second position the seal is configured to be axially misaligned with at least one of the sealing surfaces.

Advantageously the provision of a seal to seal the reservoir reduces the amount of wetting agent that is lost to evaporation or leakage prior to use. This is beneficial as it increases the certainty that there will be sufficient wetting agent at the end of the shelf life. It may also allow the storage chamber to contain less wetting agent as a smaller margin is required, thus the reservoir and therefore the overall packaging may be smaller.

Providing a catheter assembly having a storage chamber which is sealed using a seal element which is configurable to be aligned with a sealing surface in a first position and misaligned with the sealing surface in a second position provides a seal with improved functionality.

For example, in some embodiments the seal may be opened in the second position such that a flow path can be created for the wetting agent to flow to a further chamber, such as the wetting chamber or a priming chamber. Hence, the seal element can be configured to act as a valve for opening the storage chamber.

In some embodiments, the seal may remain intact in the second position such that the storage chamber remains functionally sealed, but the contact pressure exerted by the seal element is reduced. This may allow the movable insert to be withdrawn from the storage chamber when in the second position more readily whilst providing a tighter seal for transportation and storage purposes when in the first position.

The seal element may be an elastomeric material. For example, the seal may be a rubber seal or some other suitable material. The seal element may be an annular seal element. The seal element may comprise an O-ring. The seal element may comprise an X-ring. The seal element may comprise a U-cup seal. The seal element may lie in a radial plane, for example the normal plane of the longitudinal axis of the catheter assembly. The seal element may extend between radially opposed sealing surfaces. The O-ring may lie in a radial plane, for example, the normal plane of the longitudinal axis of the catheter assembly. The seal element may be provided in the form of a gasket.

The seal element may be compressible. The compression of the seal element in the first position may be greater than the compression in the second position.

The seal element may be located in a seal element housing in one of the chamber wall or the movable insert. The seal element housing may comprise a groove or channel provided within the chamber wall or movable insert. The groove or channel may be provided in part by a radially outer wall, an axial end wall and/or one or more catheter guide features provided within the storage chamber. The seal element may be overmoulded so as to become an integral part of the storage chamber or movable insert. One or more of the sealing surfaces may be provided by the seal element housing. The at least one sealing surface may slideably oppose the seal element. The at least one sealing surface may be referred to as a primary sealing surface.

The catheter assembly may further comprise a wetting agent. When in the second position, the wetting agent may be sealed within the storage chamber by the seal element maintaining a sealing contact with a secondary sealing surface adjacent to the (primary) sealing surface. Alternatively, in some embodiments, when in the second position, a flow path may be provided between the sealing surface and seal element such that the wetting agent may flow out of the storage chamber when in the second position.

At least one of the movable insert and the chamber wall may comprise a divergent portion over which the seal element passes when transitioning between the first position and second position such that the distance between the chamber wall and movable insert at the axial location of the seal element is increased when in the second position when compared to the first position. The distance may be a radial distance with respect to the longitudinal axis. The divergent portion may comprise a widening of a cavity adjacent to the seal surface. The cavity may be that of the storage chamber and/or an adjacent chamber. The adjacent chamber may be provided within the main body. The adjacent chamber may house a catheter tube. The adjacent chamber may be a priming chamber or a wetting chamber.

The divergent portion may comprise a step, taper or chamfer in the wall surface which is adjacent to the sealing surface. The sealing surface may comprise a cylindrical surface having a first diameter. An adjacent wall portion of the chamber wall or movable insert may have a second diameter which is different to the first diameter. The first diameter may be greater than the second diameter. The adjacent wall portion may be proximal an insertion end of the catheter. The adjacent wall portion may be a secondary surface.

The at least one sealing surface may be a primary sealing surface. The portion of the chamber wall or movable insert comprising the second diameter may be a secondary sealing surface. Thus, when in the second position, the seal element may contact and seal against the secondary sealing surface. The contact pressure between the secondary sealing surface and seal element may be reduced due to the increased separation between the movable insert and chamber wall at the location of the secondary seal surface and seal element. That is, the seal element may be provided in a compressed state in the first position and a decompressed state in the second position.

The catheter may be located within the storage chamber. The catheter may be co-axially nested within with the storage chamber. The catheter may be nested within a/the chamber wall so as to provide part of the storage chamber. The catheter may sealably extend through the chamber via openings in the axially opposed ends of the storage chamber.

The movable insert may be configured to move with respect to the chamber wall to a third position in which the catheter is wetted with the wetting agent. The movable insert may be configured to move in a first direction from the first position to the second position and from the second position to the third position. The first direction may be a rotational direction and/or axial direction. The movable insert may move in a second direction from the first position to the second position and a third direction from the second position to the third position. The second and third directions may be opposite to one another. The second and third directions may be axial. The movable insert may be configured to move rotationally and axially simultaneously.

The catheter assembly may further comprise a wetting chamber. The wetting chamber may be located radially inwards of the storage chamber. The catheter may be coaxially nested within the wetting chamber. The external housing, storage chamber, wetting chamber and catheter may be concentrically arranged and axially aligned on the longitudinal axis.

The catheter assembly may further comprise a priming chamber. The priming chamber being in flow series with the storage chamber and wetting chamber. The priming chamber may be located proximally of the storage chamber and the wetting chamber. The priming chamber and/or wetting chamber may be separated from the storage chamber by the seal element. The priming chamber may receive the wetting agent from the storage chamber prior to being pumped into the wetting chamber.

The storage chamber and wetting chamber may be separate chambers. The storage chamber and wetting chamber may be separated by an internal housing. The internal housing may be located in a spaced relation within the external housing to provide the storage chamber.

The storage chamber may be the wetting chamber. The wetting chamber may be defined as a cavity within the catheter assembly from which a wetting agent is able to contact an external surface of a catheter tube. The wetting agent may be applied to the catheter tube upon withdrawal of the catheter tube from the storage chamber, in which case the storage chamber can be considered to be or comprise the wetting chamber.

Alternatively, where the storage chamber and wetting chambers are separate chambers, the wetting agent may flow and/or may be pumped to and/or along the length of the wetting chamber and catheter tube. In such a case, the wetting agent may flow past the seal element. A priming chamber may be located between the storage chamber and wetting chamber and receive the wetting agent prior to it being passed along the wetting chamber. The priming chamber may be provided in the proximal end of the main body of the external housing.

When in the second position, the seal element may maintain a seal between the chamber wall and movable insert. When in the second position, the seal element may be separated from at least one of the sealing surfaces so as to provide a flow path for the wetting agent to pass the seal element.

The wetting agent may be provided within the wetting chamber when in the second position and/or a priming chamber.

The movable insert may comprise an internal housing. The internal housing may be the housing which defines the storage chamber and wetting chamber.

The catheter assembly may comprise a plurality of seals. The plurality of seals may comprise a proximal seal which is proximal to an insertion end of the catheter. The plurality of seals may comprise a second seal. The second seal may be axially separated from the proximal seal on the distal side thereof. The distal seal and proximal seal may be located radially between the movable insert and chamber wall. The distal seal and proximal seal may comprise respective distal and proximal seal elements and sealing surfaces.

The distal seal may maintain sealing contact in the first and second positions.

The catheter assembly may further comprise a pump configured to pump the wetting agent into the wetting chamber. The movable insert may comprise the pump. The internal housing may comprise the pump. The internal housing may comprise one or more pump enhancing features. The internal housing may comprise a plurality of circumferentially extending fins. The movable insert may be movable from the second position to the first position to pump the wetting agent into the wetting chamber.

The catheter may comprise a catheter tube which provides an insertion end for inserting into a patient and an outlet end comprising one or more external handling features.

The movable insert may be provided by the catheter. For example a portion of the catheter may provide the moveable insert. The portion of the catheter may be a portion other than the catheter tube, for example, a funnel or an additional body. The storage chamber may be adjacent to the outlet end of the catheter.

The catheter assembly may further comprise an actuator to move the movable insert relative to the storage chamber. The actuator may be referred to as a priming mechanism herein. The actuator may comprise a rotatable actuator. Rotating the rotatable actuator may move the movable insert relative to the chamber wall. The movement of the movable insert may be either or both of a rotational movement and an axial movement. The axial movement may be induced by the rotation of the rotational actuator. Rotation of the rotatable actuator may be converted into the axial movement between the movable insert and the chamber wall.

The catheter assembly may further comprise a cam drive for converting the rotation of the rotatable actuator into the axial movement. The catheter assembly may further comprise a screw thread for converting the rotation of the rotatable actuator into the axial movement. The cam drive may comprise a screw thread or a portion of a screw thread. The actuator may comprise one or more drive surfaces and one or more corresponding driving elements which drivably engage with one another to provide the rotational-axial movement.

The catheter assembly may further comprise an external housing which comprises a removable cap. The rotatable actuator may comprise the cap.

The cap may rotatably engage with the movable insert such that rotating the cap rotates the movable insert.

The movable insert may be configured to reciprocate upon rotation of the rotatable actuator.

The second position may be a wetting position in which the catheter is configured to be wetted by the wetting agent. Thus, when in the second position, the wetting agent may be in flow communication with an external surface of the catheter tube. The second position may be a primed position. When in the primed position, the catheter may be configured to be withdrawn from the storage chamber. In some embodiments, the primed position may correspond to a pre-pump configuration in which the wetting agent is pumped or otherwise moved into a wetting chamber.

An aspect of the present disclosure provides a catheter assembly comprising a wetting mechanism. The catheter assembly may have at least a two-step deployment. The two-step deployment may comprise: a first step which breaks a hermetic seal and at least primes the wetting mechanism, putting the catheter assembly into a leak-resistant primed configuration; and a second step which removes a catheter tube from the catheter assembly. The first stage and/or second step may additionally wet the catheter tube.

An aspect of the present disclosure provides a catheter assembly comprising: a catheter and a housing having an internal cavity in which the catheter is housed. The housing may be an external housing. The housing may comprise a hermetic seal for preserving the sterility of the internal cavity prior to use. A wetting agent chamber may be located in the internal cavity.

An aspect of the present disclosure may provide a catheter assembly comprising: a catheter. The catheter assembly may further comprise an external housing having an internal volume in which the catheter is housed. The external housing may comprise a hermetic seal for preserving the sterility of the internal volume prior to use. The catheter assembly may comprise a wetting agent chamber which may comprise one or more wetting agent seals for retaining the wetting agent within the wetting agent chamber. The catheter assembly may be configurable to comprise: a hermetically sealed configuration in which the hermetical seal is sealed and the wetting agent seal is sealed, and a primed configuration in which the hermetic seal is open and the one or more wetting agent seals are sealed.

An aspect of the present disclosure provides a catheter assembly comprising: a catheter; a housing having an internal cavity in which the catheter is housed, the housing comprising a hermetic seal for preserving the sterility of the internal cavity prior to use; a wetting agent chamber located in the internal cavity; and, wherein the catheter assembly is configured to deploy the catheter in a first step and a subsequent second step, wherein the first step comprises breaking the hermetic seal and priming the wetting agent chamber to put the catheter assembly into a leak-resistant primed configuration in which the catheter is configured to be wettable with the wetting agent; and, the second step comprises removing the catheter from the housing.

Providing a sealed configuration in which the sterility of the internal volume is preserved and a primed configuration in which the catheter assembly is retained in a potentially non-sterile but leak-resistant primed configuration allows the deployment of the catheter to be interrupted without risk of the wetting agent leaking out of the catheter assembly. This is advantageous if a user is required to temporarily put the catheter down prior to withdrawing the catheter but after breaking the hermetic seal.

The housing may comprise an external housing. The external housing may comprise a main body and a cap. The hermetic seal may be attached to the main body and/or cap. The hermetic seal may attach the cap to the main body. The hermetic seal may comprise an external surface of the catheter assembly. Thus, the external housing may comprise a cap, a main body and a hermetic seal. The hermetic seal may be a tear strip which is broken in use such that the cap is removable by hand. The hermetic seal may be broken and the wetting agent primed by rotation of the cap relative to the main body.

The first step and/or the second step may additionally wet a catheter tube of the catheter. Thus, placing the catheter assembly in a primed configuration may wet the catheter without the wetting agent being in flow communication with the exterior of the catheter assembly. Additionally or alternatively, the leak-resistant state may prevent flow communication between the wetting agent and a portion of the catheter which comprises a handling surface which is handled by a user in use. Thus, the handling surface may be maintained in a dry state prior to the catheter being removed from the housing. The handling surface may be provided by an outlet end of the catheter.

The catheter may be an intermittent catheter. The catheter may be a urinary catheter. The catheter may be a female intermittent catheter.

The catheter assembly may further comprise a priming mechanism. The priming mechanism may be referred to as actuator herein. The priming mechanism may be configured to carry out the first step with a single user action. Thus, a user may manipulate the priming mechanism by moving, for example, rotating or pulling a part of the catheter assembly to break the hermetic seal and prime the catheter assembly with a single action or movement. The first step may comprise simultaneously breaking the hermetic seal and priming the wetting agent chamber to put the catheter assembly into a leak-resistant primed configuration.

The housing may be an external housing. The housing may be rigid. The housing may comprise a cap and a main body. The cap and main body may remain engaged during the first step. The engagement of the cap and main body may be a mechanical engagement in which the cap is attached to the main body either directly or indirectly. For example, the cap may be attached to the main body via an internal housing or some other intermediate member.

The priming mechanism may comprise the cap. The cap may be drivably rotatable relative to the main body such that drivably rotating the cap breaks the hermetic seal and primes the wetting agent chamber.

The priming mechanism may comprise: a drive surface, and a driving element which engages with the drive surface such that rotational movement of the driving element or drive surface causes the other of driving element or drive surface to axially translate, or vice versa.

The drive surface may extend axially and circumferentially. The drive surface may comprise a ramp and/or helical surface. The drive surface may comprise a first axially facing surface provided by a radially projecting flange, rib, thread, track or rail, or an end wall surface.

The driving element may comprise a second axially facing surface of a radially extending flange, rib, thread, track, rail or pin, or an end wall surface.

The end wall surface may be an end wall surface of the chamber wall.

The driving element and drive surface may be collectively referred to as a cam drive.

The priming mechanism may comprise a movable insert which partially defines the wetting agent chamber. The movable insert may be configured to move between a sealed configuration and a primed configuration during the first step. The movable insert may be configured to move axially when rotated.

The wetting agent chamber may comprise a wetting agent storage chamber. Additionally, or alternatively, the wetting agent chamber may comprise a wetting chamber and/or a priming chamber. The wetting agent chamber may comprise a chamber wall and the movable insert.

Either the chamber wall or movable insert may comprise the driving element or drive surface. The other of the chamber wall and movable insert may comprise the other of the driving element and drive surface.

The driving element may comprise a plug for plugging an aperture. The aperture may be a filling aperture. The filling aperture may be provided in an external wall of the housing.

The movable insert may be configured to move axially when rotated. The cap may be rotatably engaged with the movable insert such that rotating the cap rotates and axially translates the movable insert.

The rotatable engagement between the cap and movable insert may disengage following the first step. The disengagement of the rotatable engagement may be induced by a further rotation of the cap. Thus, a user may rotate the cap in a first direction to prime the catheter assembly and further rotate the cap in the first direction to disengage the cap. The disengagement of the rotatable engagement may configure the cap for removal from the catheter assembly to expose the catheter for withdrawing.

The movable insert may be provided by the catheter (as outlined above).

The movable insert may comprise an internal housing located radially inwards of the external housing. The catheter may be located radially inwards of the internal housing.

The internal housing may be located radially within the external housing so as to provide the storage chamber therebetween.

The catheter assembly may be configured to provide mechanical feedback to a user. The mechanical feedback may be indicative of the end of the first step. The mechanical feedback may be between the first and second steps.

The first step may require a first actuating force and the second step may require a second actuating force. The first actuating force and second actuating force may be different. Thus, transitioning between the first and second actuating forces may provide a mechanical feedback for the user. The first actuating force and second actuating force may be either or both of: in different directions and different magnitudes.

The mechanical feedback may be provided by one or more stops in which the direction of actuation is required to change. Hence, the catheter assembly may comprise one or more limiters which limit the movement of the movable insert or an actuator associated with the movable insert.

The actuation of the catheter assembly required for the first and second steps may require the movement and/or removal of one or more parts. Thus, the first step may be actuated using the cap which is subsequently removed, prior to the catheter being withdrawn axially by the user.

The wetting agent chamber may comprise a wetting agent storage chamber. In some embodiments, the wetting agent storage chamber may comprise a portion of the catheter. In some embodiments, the wetting agent chamber may comprise the storage chamber and/or a wetting chamber, and/or a priming chamber.

The wetting agent seal may be any seal or combination of seals which are used to seal the storage chamber, wetting chamber or priming chamber. The wetting agent seal may comprise a seal element and sealing surface as described herein.

In some embodiments, the catheter assembly may be configured to provide the wetting agent to a wetting chamber. The catheter assembly may include a third configuration in which the hermetic seal is open and at least one of the wetting agent seals is open.

The primed configuration may relate to the storage chamber being primed such that the catheter can be removed from within the storage chamber whilst passing through the wetting agent provided therein.

The external housing may comprise a cap and a main body to which the cap is attached. The attachment may be via the hermetic seal. Rotating the cap relative to the main body may break the hermetic seal.

The wetting agent chamber may comprise a wetting agent storage chamber wall and a movable insert. The wetting agent seal may be provided between the wetting agent storage chamber wall and the movable insert. The seal may comprise a seal element.

The catheter may comprise an insertable portion. Prior to the first step the insertable portion may not be in contact with the wetting agent.

It is advantageous that prior to deployment of the catheter, for example during shipping and storage, that the insertable portion of the catheter is not in contact with the wetting agent. The insertable portion of the catheter is often made of materials which interact with the wetting agent, this interaction should only occur just prior to use.

The catheter assembly may further comprise a wetting chamber. The wetting agent may be in fluid communication with the wetting chamber when the catheter assembly is in the primed configuration. The wetting agent may be in the wetting chamber when in the third position.

The catheter assembly may further comprise a wetting chamber seal provided between the storage chamber and wetting chamber. The wetting chamber seal may be open when the catheter assembly is in the primed configuration.

The movable insert may be an internal housing in which the catheter is located. The movable insert may be the catheter. The catheter may be configured to be withdrawn from the wetting agent chamber and external housing when the catheter assembly is in the primed configuration.

The catheter assembly may further comprise an actuator to move the movable insert relative to the wetting agent chamber wall. The actuator may comprise a rotatable actuator. Rotation of the rotatable actuator may be converted into the axial movement between the movable insert and the chamber wall.

The catheter assembly may further comprise a cam drive for converting the rotation of the rotatable actuator into the axial movement. The catheter assembly may further comprise a screw thread for converting the rotation of the rotatable actuator into the axial movement. The catheter assembly may further comprise a cap, wherein the rotatable actuator comprises the cap. The cap may be rotatably engaged with the movable insert such that rotating the cap rotates the movable insert.

The cap may be rotatably engaged with the movable insert such that rotating the cap rotates the movable insert. Rotating or pulling the cap may break the hermetic seal.

Further rotating the cap or withdrawing the catheter may open the at least one wetting agent seal. The further rotation of the cap may be the same rotation which breaks the hermetic seal.

An aspect of the disclosure provides a catheter assembly comprising: a catheter having a distal outlet end and a proximal insertion end. The catheter assembly may further comprise a wetting agent storage chamber and a housing. The housing may be an external housing. The external housing may at least partially enclose the catheter and the storage chamber. The catheter assembly may further comprise a sheath connected between the catheter and the storage chamber such that withdrawing the catheter from the external housing causes withdrawal of the storage chamber from the external housing via the sheath.

An aspect of the disclosure provides a catheter assembly comprising: a catheter having a distal outlet end and a proximal insertion end; a wetting agent storage chamber; an external housing, the external housing at least partially enclosing the catheter and the storage chamber; and, a sheath connected between the catheter and the storage chamber such that withdrawing the catheter from the external housing causes withdrawal of the storage chamber from the external housing via the sheath.

Providing a sheath connected between the catheter and storage chamber provides a convenient way to remove the storage chamber from the catheter following the catheter being withdrawn through the storage chamber. Hence, a catheter tube which is insertable into a patient may be wetted with wetting agent stored in the storage chamber whilst the catheter is withdrawn from the housing, prior to/during sheathing the withdrawn catheter tube to help maintain the sterility of the catheter tube prior to insertion into the patient. Moreover, as the catheter is then introduced into the urethra it may pass through the wetting agent storage chamber for a second time, improving the wetting of the surface of the catheter.

Further, the provision of wetting mechanism which can be withdrawn from the external housing by the sheath allows the user to handle the wetted catheter tube by the storage chamber without risking contamination of the catheter tube. Providing the storage chamber as an insertion guide in this way provides an efficient way to use the space in the external housing and allow for a greater supply of wetting agent.

The sheath may be a retractable sheath. The retractable sheath may be stowed in a stowed configuration and deployed to an extended configuration. The sheath may be deployable from a stowed configuration in which the sheath is furled between the outlet end and storage chamber, to an extended configuration in which the sheath is unfurled and contains a catheter tube of the catheter located therein.

The catheter and storage chamber may be held within (e.g. attached to) the external housing such that a first predetermined force is required to withdraw the catheter from the external housing and a second predetermined force is required to disengage the storage chamber for withdrawal from the external housing. The first and second predetermined forces may be different. The second predetermined force may be greater that the first predetermined force.

The catheter assembly may further comprise an insertion guide which is deployable to the insertion end of the catheter for use. The insertion guide may comprise an external handling surface and be configured to aid the placement of the insertion end at the urethra of a patient. The storage chamber may comprise the insertion guide.

The catheter assembly may further comprise a release mechanism arranged to releasably retain the storage chamber.

The release mechanism may comprise a releasable coupling between the external housing and storage chamber. The release mechanism may provide mechanical feedback for a user withdrawing the catheter and/or storage chamber. Thus, the release mechanism may require a predetermined amount of force to actuate the releasable coupling. The predetermined amount of force may be the second predetermined force.

The releasable coupling may comprise one or more projections extending from either or both the external housing and wetting agent chamber. The projections may be received in one or more corresponding recesses provided in the other of the external housing and wetting agent chamber.

There may be an equal number of releasable projections and recesses. The projections and recesses may be configured to remain engaged when subjected to the first predetermined force and configured to disengage when subject to the second predetermined force.

The first and second predetermined forces may be axial forces. The axial forces may be applied by a user via the catheter.

The projections may be elongate having a longitudinal axis. The projections may be configured to deflect away from the longitudinal axis when the second predetermined force is applied or is exceeded.

The catheter may be elongate and may define a principal longitudinal axis of the catheter assembly. The longitudinal axis of the projections may extend in the direction of the principal longitudinal axis.

The catheter assembly may comprise a plurality of projections and recesses distributed circumferentially about the principal axis. The plurality of projections and recesses may combine to provide an annular clasp.

The deflection of the projections may be in a radially outwards direction.

The release mechanism may be configured to prevent relative rotation of the external housing and wetting agent chamber. Thus, rotating a movable insert within or which forms part of the storage chamber may not result in relative rotation between the storage chamber and external housing.

The catheter assembly may further comprise a seal element in the storage chamber and a movable insert received within the storage chamber. The seal element may be located between the storage chamber and movable insert and may be radially inwards and axially aligned with the plurality of projections and/or recesses. Axially aligning position of the seal element and the releasable coupling which positions the storage chamber relative to the housing may help maintain the seal provided by the seal element.

An aspect of the present disclosure provides a catheter assembly comprising: a catheter; and a wetting agent storage chamber in which the catheter is located. The wetting agent storage chamber may comprise at least one projection configured to guide the catheter within the wetting chamber.

The at least one projection may guide the catheter within the wetting chamber during a withdrawal of the catheter. The at least one projection may guide the catheter within the wetting chamber during a reinsertion of the catheter through the wetting chamber.

An aspect of the present disclosure provides a catheter assembly comprising: a catheter; and a wetting agent storage chamber in which the catheter is located, wherein the wetting agent storage chamber comprises at least one projection configured to guide the catheter within the wetting chamber, wherein the at least one projection retains a seal element in the wetting chamber.

Providing a storage chamber having one or more features such as a projection to locate the catheter within the wetting chamber during withdrawal or reinsertion allows the positioning of the catheter to be controlled which provides for an improved wetting of a catheter tube of the catheter. During reinsertion it also ensure the catheter does not become trapped with the wetting chamber.

An aspect of the disclosure provides a catheter assembly comprising: a catheter; and a wetting agent storage chamber in which the catheter is located. The wetting agent storage chamber may comprise at least one projection configured to retain a seal element within the wetting chamber. The at least one projection may be configured to retain the seal element within the wetting agent storage chamber during withdrawal of the catheter.

Providing a storage chamber having one or more features such as a projection to locate a seal element therein can provide a convenient way to locate the seal element and maintain its relation to the catheter during withdrawal of a catheter tube of the catheter. This is beneficial as it ensures the seal element is correctly located upon reinsertion of the catheter into the wetting agent storage chamber, ensuring a seal is maintained after reinsertion. It also avoids the seal element being carried out on the catheter, which would obviously cause problems on insertion of the catheter into the urethra.

The at least one projection configured to retain the seal element within the wetting chamber may be the at least one projection configured to guide the catheter withing the wetting chamber.

The at least one projection may comprise a plurality of ribs or fins. The plurality of ribs or fins may extend axially and radially. The at least one projection may comprise a plurality of pins or fins. The at least one projection may comprise a plurality of pedestals. The at least one projection may comprise a plurality of flanges. The plurality of projections may comprise any combination of ribs and/or fins and/or pins and/or pedestals and/or flanges.

The storage chamber may comprise an axially extending radially outer wall and at least one radially extending end wall. The storage chamber may comprise a first radially extending end wall and a second radially extending end wall. The end walls may comprise one or more tubular flanges extending axially therefrom.

The plurality of projections may extend from either or both of the radially outer wall or the at least one end wall. The plurality of projections may extend radially inwards from the radially outer wall of the wetting agent storage chamber.

The plurality of projections may be circumferentially distributed. There may be at least 2 projections. There may be at least 3 projections. There may be at least 4 projections. There may be at least 6 projections. There may be at least 8 projections. There may be 4 projections.

The catheter and storage chamber may be concentrically aligned.

The projections may be shaped to define a void. The void may be defined by a discontinuity in the projections. The projections may only partially extend along the axial extent of the storage chamber. The void may be partially defined by an axial edge of the projections. The void may be partially defined by an end wall of the storage chamber. The discontinuity may be provided by a first portion of each projection extending radially inwards by a first amount and a second portion of each projection extending radially inwards by a second, lesser amount.

The wetting agent storage chamber may comprise at least one radially extending end wall and at least one projection extending axially within the wetting agent storage chamber, the at least one projection terminating short of the end wall to define a void.

The catheter may define a longitudinal axis and the each of the plurality of projections may lie in a plane defined by the longitudinal axis. The plurality of projections may be provided in diametrically opposing pairs.

The seal element may be elastomeric. The seal element may be annular. The seal element may be an O-ring. The seal element may be an X-ring. The seal element may be a U-cup seal.

The O-ring may be arranged in the void. The void may define a seat for the seal element. The axial edges of the projections may define a seat for the seal element. The seat may axially restrain the seal element during transition of the catheter from a stowed position to a wetting position. The seat may axially restrain the seal element during withdrawal of the catheter. This is beneficial as it ensures the seal element is correctly located upon reinsertion of the catheter into the wetting agent storage chamber, ensuring a seal is maintained after reinsertion. It also avoids the seal element being carried out on the catheter, which would obviously cause problems on insertion of the catheter into the urethra.

The storage chamber may comprise two openings arranged at opposing axial ends of the storage chamber through which the catheter may pass. The projections may define a channel between the two openings. The radially inner edges of the projections may define a guide for guiding the passage of the catheter during a withdrawal or re-passing/re-insertion of the catheter. The radially inner edges of the projections may define a guide for guiding the passage of the catheter during a withdrawal or re-passing/re-insertion of the catheter. The guide may extend at least 50% of the distance between the two openings, preferably the guide may extend at least 80% of the distance between the two openings. The guide may extend at least 40% of the distance between the two openings. The guide may extend at least 50% of the distance between the two openings. The guide may extend at least 60% of the distance between the two openings. The guide may extend at least 70% of the distance between the two openings.

The separation between the radially inner edges of adjacent projections may be less than the diameter of the catheter. By ensuring the separation between the radially inner edges of adjacent protections being less than the diameter of the catheter, the catheter is restricted from deviating from the channel defined by the projections.

The diameter of the guide may be approximately equal to the diameter of one or more openings of the wetting chamber. The diameter of the guide may be approximately equal to the diameter of sealing surface of the moveable insert. The diameter of the guide may be larger than the diameter of sealing surface of the moveable insert.

An aspect of the invention provides a catheter assembly comprising: an external housing; a catheter located within the external housing; and a movable insert. The movable insert may be an internal housing arranged between the external housing and the catheter. An outer surface of the internal housing and an inner surface of the external housing may together define a wetting agent storage chamber.

An aspect of the invention provides a catheter assembly comprising: an external housing; a catheter located within the external housing; a movable insert comprising an internal housing arranged between the external housing and the catheter, wherein an outer surface of the internal housing and an inner surface of the external housing together define a wetting agent storage chamber.

Providing an internal housing between an external housing and the catheter may provide an advantageous location for the storage of the wetting agent. Such a location may provide a large volume for the wetting agent. Further, the location adjacent the external housing may provide a convenient location for filling purposes following the assembly of the catheter assembly. The internal housing may also advantageously be used to provide a wetting chamber around the catheter.

The internal housing may comprise an elongate tubular member. The elongate tubular member may be concentrically mounted within the external housing.

The internal housing may be located in a radially spaced relation within the external housing to provide the storage chamber therebetween. Either or both of the internal housing and external housing may comprise at least one projection extending between the internal housing and the external housing.

The at least one projection may be an elongate rib. The at least one projection may extend circumferentially around the internal housing.

The at least one projection may include an axial flow passage therethrough. The at least one projection may extend only partially around the internal housing to provide an axial flow passage therepast. The at least one projection may comprise an annular rib. The annular rib may be discontinuous so as to provide a flow passage therethrough. The axial flow passage allows the projections to extend between the internal housing and external housing to aid positioning of the internal housing within the external housing whilst still allowing fluid to flow along the length of the storage chamber. Additionally or alternatively, the flow passage may control the extent of the axial flow such that the internal housing may be utilised as a pump.

The catheter assembly may comprise a plurality of projections. The plurality of projections may be distributed axially along the length of the internal housing or external housing.

The at least one projection may extend from the internal housing so as to be movable in relation to the external housing. Moving the internal housing and projection(s) axially along the longitudinal axis against wetting agent will cause the at least one projection to urge the wetting agent in the direction of travel. Thus, the at least one projection may be configured to pump the wetting fluid out of the storage chamber during axial movement of the internal housing.

The at least one projection may extend between the external housing and internal housing with a minimum clearance. Hence, at least one projection may be configured to radially locate the internal housing whilst permitting axial movement therein.

The external housing may comprise a filling aperture in flow communication with the storage chamber. The external housing may comprise a cap and a main body. The filling aperture may be provided in an external wall of the main body. The filling aperture may be configured to receive a plug. The catheter assembly may further comprise the plug.

The catheter assembly may further comprise an actuator for moving the internal housing. The actuator may be referred to as a priming mechanism. The actuator may comprise a driving surface against which a driving element acts to move the internal housing. The driving element may comprise the plug.

Either of the driving element or drive surface may be provided on either of a chamber wall of the storage chamber or the movable insert received within the chamber wall. The other of the driving element and drive surface may be provided on the other of the chamber wall and movable insert. The drive surface and driving element may be configured such that relative rotation of the movable insert and chamber wall results in axial movement of the movable insert or chamber wall.

The catheter assembly may further comprise a wetting agent within the storage chamber and contacting the external housing and internal housing.

The movable insert may be movable between a sealed configuration and a primed configuration. During movement to the primed configuration, the storage chamber may be open to provide a flow path for the wetting agent to exit the storage chamber. The flow path may extend into a priming chamber or a wetting chamber in which the catheter is located.

The catheter assembly may comprise one or more vents. The storage chamber may comprise the one or more vents. The one or more vents may be air inlet vents configured to allow gas to enter the storage chamber to replace the wetting agent as it exits the storage chamber. The one or more vents may be internal to the external housing or external to the external housing. Movement of the movable insert may open the one or more vents. Moving the movable insert from a sealed configuration to an open configuration may open the one or more vents. Moving the movable insert from a sealed configuration to the primed configuration may open the one or more vents. The one or more vents and flow path opening may be arranged at axially opposing ends of the storage chamber.

The flow path may be provided by opening a seal which defines the storage chamber. The seal may be a proximal seal.

The outer surface of the movable insert may be an outer peripheral surface. The outer surface of the movable insert may be an outer circumferential surface. The inner surface of the external housing may be an inner circumferential surface.

An aspect of this disclosure provides a catheter assembly comprising an external housing, the external housing comprising a filling aperture and a wetting agent storage chamber. The filling aperture may be in flow communication with the storage chamber. The filling aperture may be configured to allow the catheter assembly to be assembled prior to the storage chamber being filled with wetting agent.

An aspect of the disclosure provides a catheter assembly comprising an external housing, the external housing comprising a filling aperture and a wetting agent storage chamber, the filling aperture being in flow communication with the storage chamber; wherein the filling aperture is configured to allow the catheter assembly to be assembled prior to the storage chamber being filled with wetting agent.

Providing a filling aperture in an external housing provides a convenient location for the filling of the storage chamber. The aperture may be conveniently plugged following a filling procedure to provide a hermetically sealed sterile assembly.

An aspect of this present disclosure may provide a method of assembling a catheter assembly (in particular, for example, a catheter assembly as defined immediately above), the method comprising: a) inserting a catheter tube and a wetting agent storage chamber into an interior cavity of an external housing; b) filling the storage chamber with a wetting agent via a filling aperture arranged on the external housing; c) sealing the external housing; and, d) sterilising the interior cavity. The steps a-d are preferably carried out in that order. Of course further steps may also be included. Sealing the external housing may comprise inserting a plug into the filling aperture. The plug may subsequently be welded to the external housing.

Sealing the external housing may comprises putting a cap on the housing. Sealing the external housing may comprise hermetically sealing the housing.

Sterilising may be irradiation sterilising, for example gamma sterilising, x-ray sterilising or EB (electron beam) sterilising.

The external housing may comprise a cap and a main body. The external housing may comprise a filling aperture in flow communication with the storage chamber. The external housing may comprise a cap and a main body. The filling aperture may be provided in an external wall of the main body. The filling aperture may be configured to receive a plug. The catheter assembly may further comprise the plug.

The catheter assembly may further comprise an actuator for moving the internal housing. The actuator may be referred to as a priming mechanism. The actuator may comprise a drive surface against which a driving element acts to move the internal housing. The driving element may comprise the plug.

Either of the driving element or drive surface may be provided on either of a chamber wall of the storage chamber or the movable insert received within the chamber wall, and wherein the other of the driving element and drive surface is provided on the other of the chamber wall and movable insert. The drive surface and driving element may be configured such that relative rotation of the movable insert and chamber wall results in axial movement of the movable insert or chamber wall.

The movable insert may be the catheter.

The catheter assembly may further comprise an internal housing within the external housing. The storage chamber may be provided between and be defined by the external housing and internal housing. The internal housing may be a movable insert configured to move axially and/or rotationally with respect to the external housing.

The drive surface may comprise at least one drive surface outlet to provide flow path between the filling aperture and storage chamber.

The drive surface may comprise at least one rail. The rail may comprise a discontinuity to provide a flow passage through the rail.

The drive surface may comprise a pair of axially spaced rails. The spacing between the rails may correspond to the diameter of the driving element.

The internal housing may be located in a spaced relation within the external housing to provide the storage chamber. The internal housing may comprise a plurality of ribs on a radially outer wall thereof so as to extend between the internal housing and the external housing.

The ribs may extend circumferentially. Each rib may include an axial flow passage therethrough.

An aspect of this disclosure may provide a catheter assembly having a longitudinal axis, the catheter assembly comprising: a catheter; a wetting agent storage chamber; and an external housing in which the catheter and storage chamber are housed. The storage chamber may comprise a movable insert configured to move axially along the longitudinal axis in relation to the external housing when the movable insert is rotated.

An aspect of the disclosure may provide a catheter assembly having a longitudinal axis, the catheter assembly comprising: a catheter; a wetting agent storage chamber; and, an external housing in which the catheter and storage chamber are housed; wherein the storage chamber comprises a movable insert configured to move axially along the longitudinal axis in relation to the external housing when the movable insert is rotated.

Providing a movable insert which translates axially when rotated allows the storage chamber to be conveniently configured for use. For example, the movable insert may be configured to transform the storage chamber from a sealed configuration to a primed configuration by rotating the movable insert, thereby allowing the catheter assembly to be primed with a single action from a user.

The movable insert may be movable between a sealed configuration and a primed configuration. The sealed configuration may correspond to a configuration in which the catheter assembly is sealed prior to use. The seal may be a hermetic or sterile seal in which the internal cavity of the external housing is sterile, or a leak-resistant sealed condition in which the wetting agent is sealed within the internal cavity of the external housing to so as to prevent escape of the wetting agent. The leak-resistant sealed condition may mean that the wetting agent is sealed within one or more of a storage chamber, a wetting chamber and a priming chamber. The leak resistant sealed condition may mean that egress from the external housing is prevented, or wetting agent contacting one or more handling surfaces of the catheter is prevented.

The primed configuration may correspond to a configuration in which the catheter is ready to be wetted. Thus, when in the wetted configuration, the catheter may be configured to be withdrawn by a user. In some embodiments, (e.g. in the sealed configuration) a seal may retain the catheter to restrict/prevent withdrawal. When in the primed configuration, the pressure exerted by the retaining seal on the catheter may be reduced to allow the catheter to be sealably withdrawn from the storage chamber, thereby wetting a catheter tube of the catheter. In some embodiments, the primed configuration may comprise an opening of a storage chamber seal such that a flow path between the storage chamber and a subsequent chamber is opened.

The storage chamber may comprise a chamber wall. The movable insert and chamber wall may be sealably engaged to seal the storage chamber via a seal.

The movable insert may be located radially inwards of the chamber wall. The seal may comprise a seal element retained by the movable insert or the chamber wall and an opposing sealing surface provided by the other of the movable insert and chamber wall.

The seal element may be adapted to align with the sealing surface when in the sealed configuration. The seal element may be adapted to be axially misaligned with the sealing surface when in the primed configuration.

The seal element may comprise an elastomeric material. The seal element may be an O-ring.

The seal element may be located in a seal element housing provided by the chamber wall or the movable insert.

At least one of the movable insert and the chamber wall may comprise a divergent portion over which the seal element passes when transitioning between the sealed configuration and primed configuration. As such the distance between the chamber wall and movable insert at the axial location of the seal element may be increased when in the primed configuration.

The divergent portion may comprise a step, taper or chamfer adjacent to the sealing surface.

The sealing surface may be a primary sealing surface. The catheter assembly may further comprise a secondary sealing surface. The seal element may seal against the secondary sealing surface when in the primed configuration.

The chamber wall or movable insert may comprise one or more axially and circumferentially extending drive surfaces. The other of the chamber wall and movable insert may comprise a driving element which engages with the drive surface to provide the axial movement of the movable insert upon relative rotation of the movable insert and chamber wall.

The drive surface may comprise a first axially facing surface provided by a radially projecting flange, rib, thread, track or rail, or an end wall surface of the respective movable insert or chamber wall.

The driving element may comprise a second axially facing surface of a radially extending flange, rib, thread, track, rail or pin, or an end wall surface of the respective movable insert or chamber wall.

The driving element may comprise a plug for plugging an aperture. The aperture may be a filling aperture. The filling aperture may be provided in an external wall of the external housing.

The drive surface may be provided by the chamber wall. The drive surface may be provided by an end wall surface of the chamber wall.

The movable insert may be movable between the primed configuration and a wetted configuration.

The external housing may comprise a main body and a cap. The cap may be rotatably engaged with the movable insert such that rotation of the cap rotates the moving insert to provide the axial movement. The rotatable engagement may be provided by one or more interlocks which rotatably couple the cap to the internal housing.

Rotating the cap may transition the movable insert from the sealed configuration to the primed configuration. Further rotating the cap may transition the movable insert from the primed configuration to the wetted configuration. Rotating the cap may transition the movable insert from the sealed configuration to the wetted configuration.

The movable insert may be configured to axially reciprocate along the longitudinal axis. The movable insert may be configured to reciprocate whilst being rotated in a continuous common direction. The reciprocating movement may comprise a distal movement followed by a proximal movement.

The cap may be sealably attached to the main body via an external housing seal. The cap and seal may be configured such that the cap breaks the external housing seal. The external housing seal may be a hermetic seal.

The chamber seal may be a proximal seal. The catheter assembly may further comprise a distal (chamber) seal. The distal seal and proximal seal may be axially spaced along the length of the movable insert and chamber wall to define a cavity for the wetting agent.

The distal seal may comprise a distal seal element and an opposing distal seal surface, wherein the distal seal surface and distal seal element are sealed in the sealed configuration and primed configuration.

The movable insert may be the catheter.

The movable insert may comprise an internal housing. The internal housing may at least partially define the storage chamber and wherein the catheter is located within the internal housing.

The internal housing may be located radially within the external housing so as to provide the storage chamber therebetween.

The catheter assembly may further comprise a movable insert rotation limiter. The rotation limiter may be configured to limit the rotation of the movable insert to less than a predetermined amount.

The internal housing may be rotatably attached to the cap via a torque activated release interlock. The release interlock may be configured to release upon continued rotation of the movable insert when the movable insert rotation limiter is engaged.

The drive surface may comprise a track. The track may be cosine shaped.

When the drive surface is a track, the track may extend between a first end point and a second end point and have a mid-point therebetween. The first end point and second end point may be axially distal relative to the mid-point. The second end point may comprise the rotation limiter.

The track may extend circumferentially through at least 180 degrees and less than 360 degrees. The track may extend circumferentially for 270 degrees. The cap may disengage from the movable insert after 270 degrees of rotation. The cap may be released from the catheter assembly after a further 90 degrees of rotation. Thus, a single full rotation of the cap relative to the main body may transition the catheter assembly from a sealed configuration to a primed configuration to an open/wetted configuration from which the catheter can be removed. The transition from the sealed configuration to the primed configuration may additionally break a hermetic seal.

The external surface of the catheter may be provided in a wetting chamber which exists between an inner surface of the external housing and an external surface of the catheter; such a wetting chamber may be defined by a sheath, or a sheath may be provided within the wetting chamber.

The catheter assembly may comprise a hermetic seal for preserving the sterility of the internal volume prior to use.

When in a sealed configuration, the hermetic seal may be intact. When in a primed or wetting configuration, the hermetic seal may be broken such that the internal volume of the external housing is at least partially open to the external air such that sterile environment may be considered breached.

When in a sealed configuration, a wetting agent chamber may be sealed by one or more wetting agent seals. The wetting agent storage chamber may comprise a wetting agent storage chamber and/or a priming chamber and/or a wetting chamber in which the catheter is located to be wetted.

When in a primed configuration and/or wetting configuration, the wetting agent seal may be intact so as to be sealed in a leak resistant manner thereby preventing escape of the wetting agent to the exterior of the catheter assembly or a catheter outlet end having external handling surfaces.

The catheter assembly may comprise a third configuration in which the hermetic seal is open and the wetting agent seal is open. When the wetting agent seal is open, the catheter may be configured to be withdrawn from the external housing.

The external housing may comprise a cap and a main body to which the cap is attached via the hermetic seal. The hermetic seal may comprise a tear strip which is removed by hand prior to use such that the cap is removable by hand. The hermetic seal may be broken by rotation of the cap relative to the main body.

The wetting agent chamber may comprise a wetting agent storage chamber. The storage chamber may comprise a chamber wall and a movable insert. The wetting agent seal may be provided between the wetting agent storage chamber wall and the movable insert.

The catheter assembly may further comprise a wetting chamber. The wetting agent may be in fluid communication with the wetting chamber when the catheter assembly is in the primed configuration.

The catheter assembly may comprise a wetting chamber seal provided between the storage chamber and wetting chamber. The wetting chamber seal may be open when the catheter assembly is in the primed configuration.

The movable insert may be an internal housing in which the catheter is located. The movable insert may be the catheter.

The catheter may be configured to be withdrawn from the wetting agent chamber and external housing when the catheter assembly is in the primed configuration.

Transitioning between the sealed configuration and the primed configuration may comprise moving the movable insert. The moving of the movable insert may comprise rotating the movable insert and/or moving the movable insert axially.

The catheter assembly may comprise an actuator for moving the movable insert. Optional features of the actuator are described herein.

The catheter comprises a catheter tube and an outlet body. The catheter may comprise an insertion end for inserting into the patient and an outlet end from which fluid is excreted during use. The outlet end may comprise one or more flow enhancing features such as a funnel which diverges along the flow direction. The outlet end may comprise an external handling surface. The external handling surface may be exposed for a user to handle when the cap is removed. The external handling surface may comprise one or more surface features to enhance a user's grip. The one or more surface features may comprise one or more grooves. The catheter tube may comprise one or more inlets for receiving urine at an insertion end thereof.

The catheter tube may be functionalised. For example it may comprise, be integrated with or be coated with a hydrophilic component (e.g. a hydrophilic polymer). The hydrophilic component serves to reduce friction further upon application of the wetting agent. At least an external surface of the catheter tube may be functionalised, e.g. the hydrophilic component may be provided on at least an external surface of the catheter tube (which is in contact with the urethra in use). The catheter may comprise a main flow path for the passage of urine. The main flow path may extend along and define a longitudinal axis of the catheter. The main flow path may be provided by a wall of catheter tube. The main flow path may have a proximal inlet at an insertion end of the catheter, and a distal outlet.

The catheter may comprise an outlet body. The outlet body may incorporate the terminal end of the catheter tube. The outlet body may comprise the external handling surface of the catheter. The outlet body may comprise one or more flow enhancing features for aiding the flow from catheter tube. The one or more flow enhancing features may comprise a funnel, for example.

The outlet body may comprise or be referred to as a connector which connects the outlet end, e.g. a funnel and/or the external handling features, and the catheter tube.

The external surface of the catheter may be provided in a wetting chamber which exists between an inner surface of the external housing and an external surface of the catheter tube.

The sheath may be a retractable sheath. The retractable sheath may be configured to be retracted during insertion of the catheter such that it provides a temporary enclosure around the catheter tube prior to insertion.

The sheath may provide a restraint for a retractable insertion guide which is provided at the proximal end of the catheter towards the insertion end and used to locate the catheter tube at the entrance to the urethra. The sheath may tether the insertion guide and/or storage chamber to the outlet end of the catheter such that withdrawal of the catheter tube unfurls the sheath and a full withdrawal of the catheter from the external housing results in the insertion guide and/or storage chamber being withdrawn from the external housing.

The storage chamber may comprise the insertion guide. The insertion guide may be provided by the proximal end of the storage chamber.

The catheter assembly may comprise a wetting chamber which may be defined by a sheath, or in which a sheath may be provided.

The storage chamber may comprise an annular chamber in which the catheter is located. The storage chamber may be located at a distal end of the catheter. The storage chamber may surround the catheter between an outlet end of the catheter and the catheter tube. The catheter outlet may be connected to the catheter tube by a connection portion. The catheter, for example, the connection portion, may comprise one or more sealing surfaces against which a seal element may seal in use.

The storage chamber may comprise a chamber wall and a surface of the catheter. The catheter may be a movable insert. The chamber wall may comprise an axially extending radially outer wall. The chamber wall may comprise end walls extending radially inwards from the radially outer wall towards the catheter. The end walls may comprise a radially extending portion and annular flanges extending along the catheter. The annular flanges may comprise a reduced radius compared with the radius of the radially outer wall.

The storage chamber may comprise a plurality of projections which define a guide tube through which the catheter passes. The plurality of projections may guide the catheter during withdrawal of the catheter so as to maintain concentricity. The plurality of projections may comprise a plurality of axially extending ribs. The plurality of projections may extend from a distal end wall of the storage chamber wall. The plurality of projections may extend radially inwards from the radially outer wall. The seal housing may be defined within the radially outer wall. The seal housing may be defined by the plurality of projections and an end wall of the chamber wall.

The storage chamber may be configured to have a sealed position and primed position. The sealed and primed positions may be referred to as sealed and primed configurations. The sealed position may correspond to the seal element being on the primary sealing surface. The primed position may correspond to the seal element being on a second sealing surface. The seal contact pressure may be greater in the sealed position than the seal contact pressure in the primed position.

The sealed configuration may correspond to a sealed configuration of the catheter assembly in which the catheter assembly is hermetically sealed by a hermetic seal.

The storage chamber may comprise at least two seal elements which are axially separated along the catheter so as to provide a distal seal comprising a distal seal element and a proximal seal comprising a proximal seal element.

The distal seal element may be provided on a seal surface having a constant profile between the sealed configuration and primed configuration and/or wetting configuration. The distal seal sealing surface may be defined by one or more radial projections which define a recess in which the distal seal element is retained. The distal seal element may be retained within the recess when the catheter is removed from the external housing.

The proximal seal may comprise a proximal seal surface. The proximal seal surface may be raised with respect to the proximal and/or distal portions of the seal surface. Thus, the proximal seal may comprise a divergent portion over which the seal element passes when transitioning between the sealed configuration and the primed configuration and/or wetting configuration such that the distance between the chamber wall and movable insert at the axial location of the seal element is increased when in the wetting configuration.

The proximal seal may be arranged in a proximal seal housing. The proximal seal housing may be provided within the radially outer wall. The proximal seal housing may be provided by the plurality of projections and an end wall of the chamber wall.

The storage chamber may be configured to have a sealed position and one or more of a primed position and wetting position. The sealed, primed and wetting positions may be referred to as configurations. Transitioning between the sealed configuration and primed configuration and/or wetting configurations may be achieved using an actuator. The actuator may be referred to as a priming mechanism.

The actuator may comprise a rotatable actuator in which a user may rotate a rotor, for example, a cap of the external housing or the catheter to transition the catheter assembly and/or wetting agent chamber and/or storage chamber between sealed, primed and/or wetting configurations. Rotation of the rotatable actuator may be converted into the axial movement between the movable insert and a chamber wall of the wetting agent storage chamber.

The actuator may comprise a drive surface which drivably engages with a driving element. The drive surface may comprise one or more helical members which urge against a corresponding driving element so as to drive the movable insert axially in relation to the storage chamber. The helical members may be fins which extend circumferentially and axially around the catheter. The drive surface and driving element may be located towards the outlet end of the catheter.

The drive surface may extend only partially around the longitudinal axis. For example, the drive surface may be extend around 90 degrees. There may be a plurality of circumferentially distributed drive surfaces members. The drive surface and driving element may be referred to as a cam drive for converting the rotation of the rotatable actuator into the axial movement.

The rotatable actuator may comprise the cap. The cap may be rotatably engaged with the movable insert such that rotating the cap rotates the movable insert. The movable insert may be the catheter.

The cap may comprise one or more radially extending cap projections which engage with corresponding radially extending catheter outlet end projections to provide the rotational engagement. Either or both of the cap projections and the catheter outlet projections may be axially extending radial fins. Each of the fins may lie in a plane defined by the longitudinal axis. The rotatable engagement between the cap and catheter may be configured to allow axial movement such that the cap can be removed axially from the rotatable engagement following a rotation of the cap though a predetermined angle.

The movable insert may be the internal housing. The internal housing may be configured to move axially upon rotation of the rotatable actuator. The internal housing may be configured to reciprocate upon rotation of the rotatable actuator. Thus, rotating the rotatable actuator may move the internal housing in a first axial direction followed by a second axial direction. The rotational direction of the rotating actuator may be in the same direction. The first axial direction may be distal in relation to the insertion end of the catheter. The second direction may be proximal.

The driving surface may comprise a track which engages with a driving element. The track may be referred to as a plunger track. The track may be provided on either the internal housing or main body of the external housing. The driving element may comprise a projection which may be provided on the other of the internal housing and external housing.

The track and driving element may be provided within the storage chamber. The driving element may comprise a plug which is received within a filling orifice for the storage chamber. Thus, the main body may comprise at least one aperture extending through an external wall thereof, the aperture providing access to the storage chamber such that the wetting fluid may be received via the aperture. The aperture may be configured to receive the driving element following the filling procedure. Thus, the aperture may oppose the guide track in which the driving element is received.

The track may extend from a first endpoint which corresponds to the sealed configuration, to a mid-point which corresponds to a primed configuration, to a third endpoint which corresponds to a wetted configuration. The track extends in a first circumferential direction and a first axial direction between the first end point and mid-point, and in the first circumferential direction and in a second axial direction between the mid-point and end point. The first axial direction and second axial direction may oppose one another. The first axial direction may be a proximal direction. The second axial direction may be a distal direction.

The track may be comprise one or more track walls. The track walls may be discontinuous so as to provide an outlet for wetting agent in the track. Thus, the track may receive the wetting agent from a filling aperture prior to flowing into the internal volume of the storage chamber.

Optional features set out above may apply to any aspect of the invention. Thus, for example, the preferred length of the catheter and assembly is only described once above, but applies to all aspects and combinations of aspects and other optional features

DETAILED DESCRIPTION OF THE INVENTION

In order that the invention may be more clearly understood one or more embodiments thereof will now be described, by way of example only, with reference to the accompanying drawings, of which:

FIG. 1a shows an exploded view of a catheter assembly according to an embodiment of the disclosure;

FIG. 1b shows a side view of the catheter assembly of FIG. 1 in a closed or sealed configuration;

FIGS. 2a to 2c show the steps of removing the cap from the catheter assembly and stowing the cap on the opposing end of the catheter assembly external housing;

FIGS. 10a to 10f show a sequence of side view images of the catheter assembly according to an embodiment of the invention demonstrating the principal steps for wetting and removing a catheter from the external housing;

FIG. 11 shows a longitudinally exploded view of a catheter assembly according to an embodiment of the disclosure;

FIG. 12 shows a perspective view of the catheter assembly of FIG. 11;

FIG. 20 shows an exploded view of a catheter assembly according to the present invention FIG. 21a shows a side view of a catheter assembly of FIG. 20;

FIG. 21b shows a side view of the catheter assembly of FIG. 20 with the case removed;

FIG. 21c shows a side view of the catheter assembly of FIG. 20, including a sheath, with the case removed.

Figure 3:
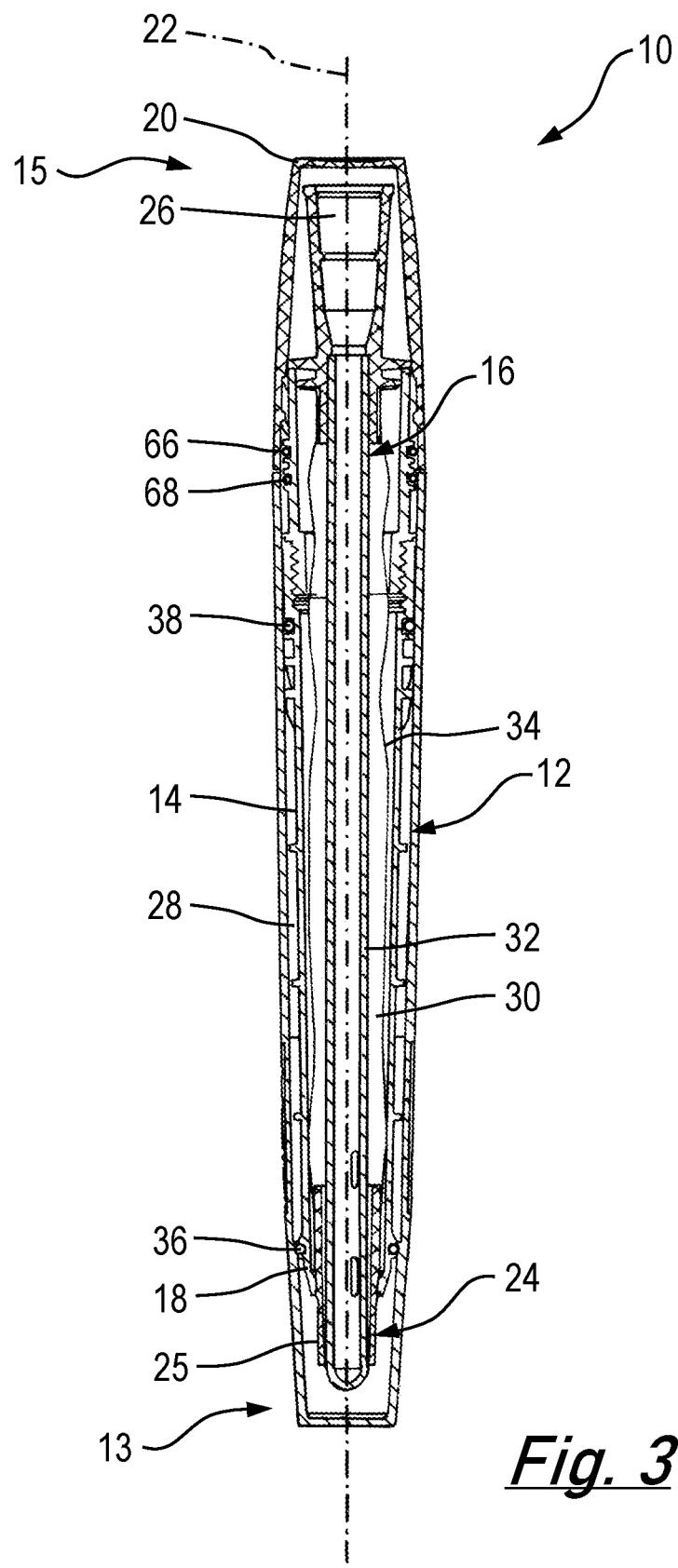
FIG. 3 shows a longitudinal section of the catheter assembly of FIG. 1.

FIG. 1 shows an axially exploded view of a catheter assembly 10 according to the present invention. The catheter assembly comprises an external housing 12, an internal housing 14 and a catheter 16. The external housing 12, internal housing 14 and catheter 16 are concentrically arranged such that the catheter 16 is located within the internal housing 14 which is located within the external housing 12 in a radially nested configuration.

The catheter assembly 10 may be configured such that the catheter 16 may be wetted prior to being withdrawn from the external housing 12. The wetting agent used to wet the catheter 16 prior to use and may be held in a wetting agent storage chamber which is defined between the external housing 12 and the internal housing 14. The wetting agent may be delivered to the catheter 16 via a wetting chamber which is defined between the internal housing 14 and catheter. The wetting agent may be pumped or driven into the wetting chamber from the storage chamber. The wetting agent may be water or some other suitable agent, as well known in the art.

Referring to FIGS. 1a, 1b, 3, 4 and 9b and 9c, the external housing 12 comprises a main body 18 in which a portion of the internal housing 14 and catheter 16 are housed, and a cap 20 which is detachable so as to be removable by a user prior to use of the catheter. Removing the cap 20 may expose the catheter 16 such that it can be withdrawn from the external housing 12.

The external housing 12 provides an enclosed volume in which the catheter 16 can be housed for storage and transportation prior to use. The main body 18 and cap 20 may provide a sterile cavity in which the catheter 16 is located. The external housing 12 is generally elongate having a longitudinal axis 22 which can be taken to be the principal axis of the catheter assembly 10 and also provide the longitudinal axis for the internal housing 14 and catheter 16 etc. References to a longitudinal axis, axial or radial in this disclosure should be taken to be with reference to the longitudinal axis 22 unless stated otherwise.

The enclosed volume provided by the external housing 12 is defined by an external wall of the housing 12 which extends from a first proximal end 13, which receives an insertion end 24 of the catheter 16, to a second distal end 15 in which a catheter outlet end 26 is received. In the embodiment shown, the second end 15 is provided by the cap 20. Thus, the removal of the cap 20 exposes the outlet end 26 of the catheter 16 such that a user can grip and remove the catheter 16 from the housing 12 for use.

The external profile of the housing 12 can be any required for aesthetic or functional purposes and, in the example shown, is generally cylindrical, tapering towards the first end to aid insertion into a storage receptacle or pocket, for example, and tapering towards the second end along the length of the cap 20.

The cap 20 comprises an open-ended generally cylindrical enclosure having a circumferential external wall which extends coaxially along the longitudinal axis 22, and a radially extending, axially facing end wall which provides a closed end at the terminal end of the cap 20 and external housing 12. The cap 20 mates with the distal end of the main body 18, such that the main body 18 is received within an open end of the cap 20. However, it will be appreciated that the cap 20 could be received within an open end of the main body in some embodiments.

Figure 5:
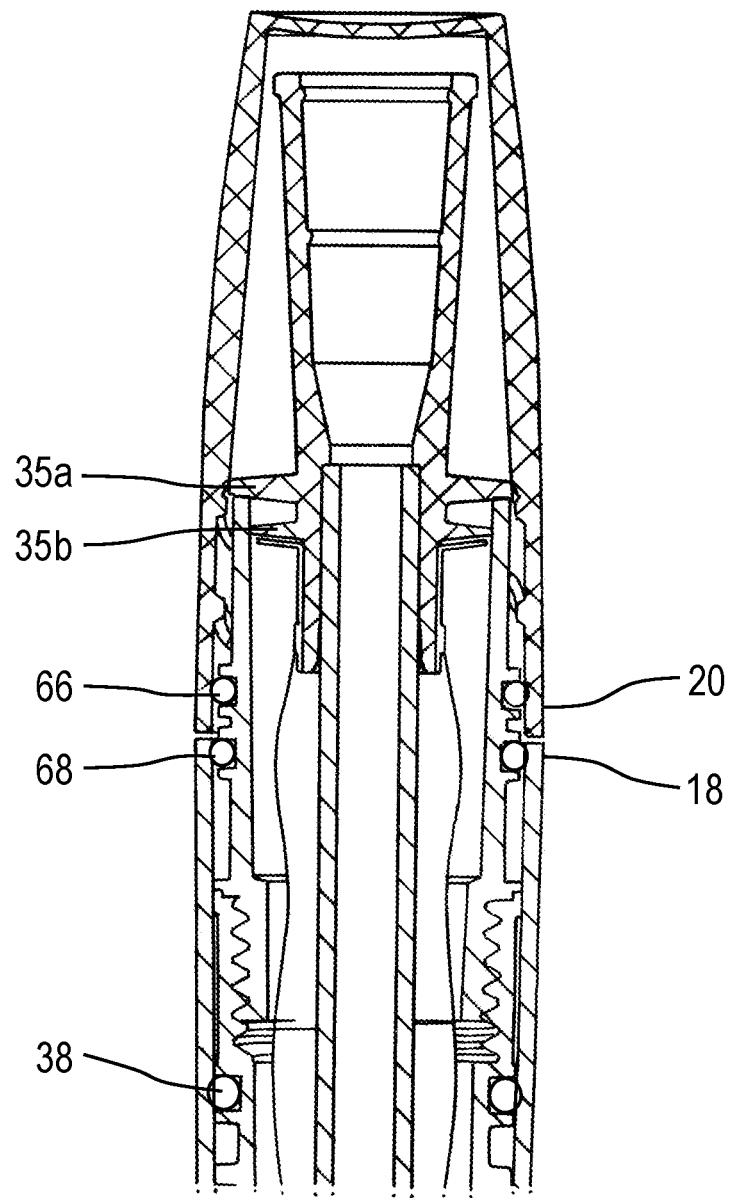
FIG. 5 shows an enlarged longitudinal sectional view of the distal end of the catheter assembly of FIG. 3.

A hermetic seal may be provided between the cap 20 and main body 18 to preserve the sterility of the internal volume of the external housing 12, prior to use. The hermetic seal of the embodiment described comprises one or more (in this case two) internal seals 66 and 68 as shown in FIGS. 3 and 5 and described further below. Additionally/alternatively a hermetic seal may be provided by a tamper proof connection or strip between the main body 18 and cap 20.

The external housing 12 may be used to transport the catheter 16 ready for use and also to dispose of the catheter following use. In order to prevent the cap 20 being misplaced or separated from the main body 18 whilst the catheter 16 is being used, and to avoid having an additional item to store in an environment which may not be conducive to hygienic storage (such as a public lavatory) the cap 20 may be temporarily mounted to the main body 18. Thus, the cap 20 may be removed from the open end of the main body 18 to expose the catheter 16 for removal and use, and mounted on the closed end of the main body 18. Once the catheter 16 has been used, it may be placed back within the main body 18 and the cap 20 re-connected with the open end of the main body 18 to enclose the used catheter 16 therein for disposal.

This process can be seen in FIGS. 2a to 2c in which FIG. 2a shows a catheter assembly 10 in which cap 20 is detachably attached prior to use, FIG. 2b shows the cap 20 being removed from the main body 18 and moved to the opposing end (as indicated by the arrows), and FIG. 2c shows the cap 20 attached to the opposing end of the main body 18. The catheter 16 is not shown but it will be appreciated that it would be exposed at the uppermost end of the main body 18 as shown, when present.

To enable the temporary mounting of the cap 20 onto the closed end of the main body 18, the external surface of the closed end of the main body 18 and the inner surface of the cap 20 may comprise corresponding mating surfaces. These are indicated by reference 21 for the main body 18 in FIG. 2a and reference numeral 21' in FIG. 9c for the cap 20. The mating surfaces 21, 21' may be configured to provide an interference fit in which the frictional engagement between the cap 20 and closed end of the main body 18 is sufficient to temporarily retain the cap 20. The interference fit may be achieved by providing a suitably shaped, and in this embodiment suitably large contacting surface area between the inner surface of the cap 20 and outer surface of the main body 18. As such, an axial portion of the outer surface of the main body 18 may have a profile which corresponds to the inner surface of the cap 20. In the example shown in FIGS. 2a-2c, the profile may be a uniform taper in which the angle of the taper along the mating surface is constant, but other profiles are possible.

The cap 20 and/or main body 18 will generally be substantially rigid so as to provide protection for the catheter 16 during transportation and to preserve integrity of the enclosed volume and maintain sterility. However, it will be appreciated that the cap 20 and/or main body 18 may be sufficiently resilient to allow a small amount of deformation to assist with the interference fit between the cap 20 and main body 18.

In addition, or alternatively, to the inner surface of the cap 20 and the outer surface of the main body 18 having corresponding profiles, either or both of the cap 20 and main body 18 may comprise mating surfaces 21, 21' comprising one or more formations which provide or enhance the interference fit and/or attachment of the cap 20 to the main body 18. For example, the cap 20 may be fitted to the closed end of the main body 18 using radial projections such as the ribs 286b described in relation to the embodiment of FIG. 15 below, using a click-fit engagement in which the cap 20 resiliently engages with one or more interlocking features such as a circumferentially extending rib or a number of circumferentially distributed pips. Providing a click-fit engagement may help provide users with feedback that the cap 20 has been securely attached. Alternatively or additionally, the cap 20 and/or main body 18 may comprise one or more inserts, coatings (such as overmoulding with a softer material), liners, screw threads or other features which enhance one or more of the resilience, contacting surface area, coefficient of friction or engagement between the cap 20 and main body 18.

The main body 18 and cap 20 may be made from thermoplastics, for example polypropylene. Other polymers such as polycarbonate, polyethylene, or nylon could be used. Equally an overmoulded design where a softer material is utilised on the inside of the cap or a portion of the outside of the body may be used to aid with retention of the cap onto the body The cap 20 may be removed from the main body 18 in an axial direction prior to being inverted and located on the closed end of the main body 18 in the same axial direction. The cap 20 may be pulled linearly off the main body 18, or may be rotated or twisted off, for example, where the cap 20 is attached via a screw thread for example. An example of a screw thread 62b and 62a can be seen in FIGS. 9a and 9c.

Part or all of the internal surface of the cap 20 may provide the mating surfaces 21'. The embodiment of FIG. 9c includes three portions which provide separate functions. The first portion is the mating surface 21' portion located distal-most and extending from the closed end towards open proximal end, ending partway along the internal length of the cap 20. A second portion includes a screw thread 62a for engaging with an internal housing 14 of the catheter assembly 10, and the third portion provides anti-rotation features 60b, which are described further below. It will be appreciated that other configurations of cap 20 are possible, and the provision and respective location of the various portions may differ in other embodiments.

As noted above, the profile of the external housing 12 may be longitudinally tapered. The transverse cross-sectional profile of the external surface of the cap 20 may be any desired. The transverse cross-sectional profile may be round, for example, circular or oval. In some embodiments, the transverse profile may be polygonal such as triangular or square. FIG. 9b shows an embodiment in which the external surface 20' of the cap 20 is a rounded square to aid user's grip for rotating the cap 20 during actuation and/or removal steps.

Figure 4:
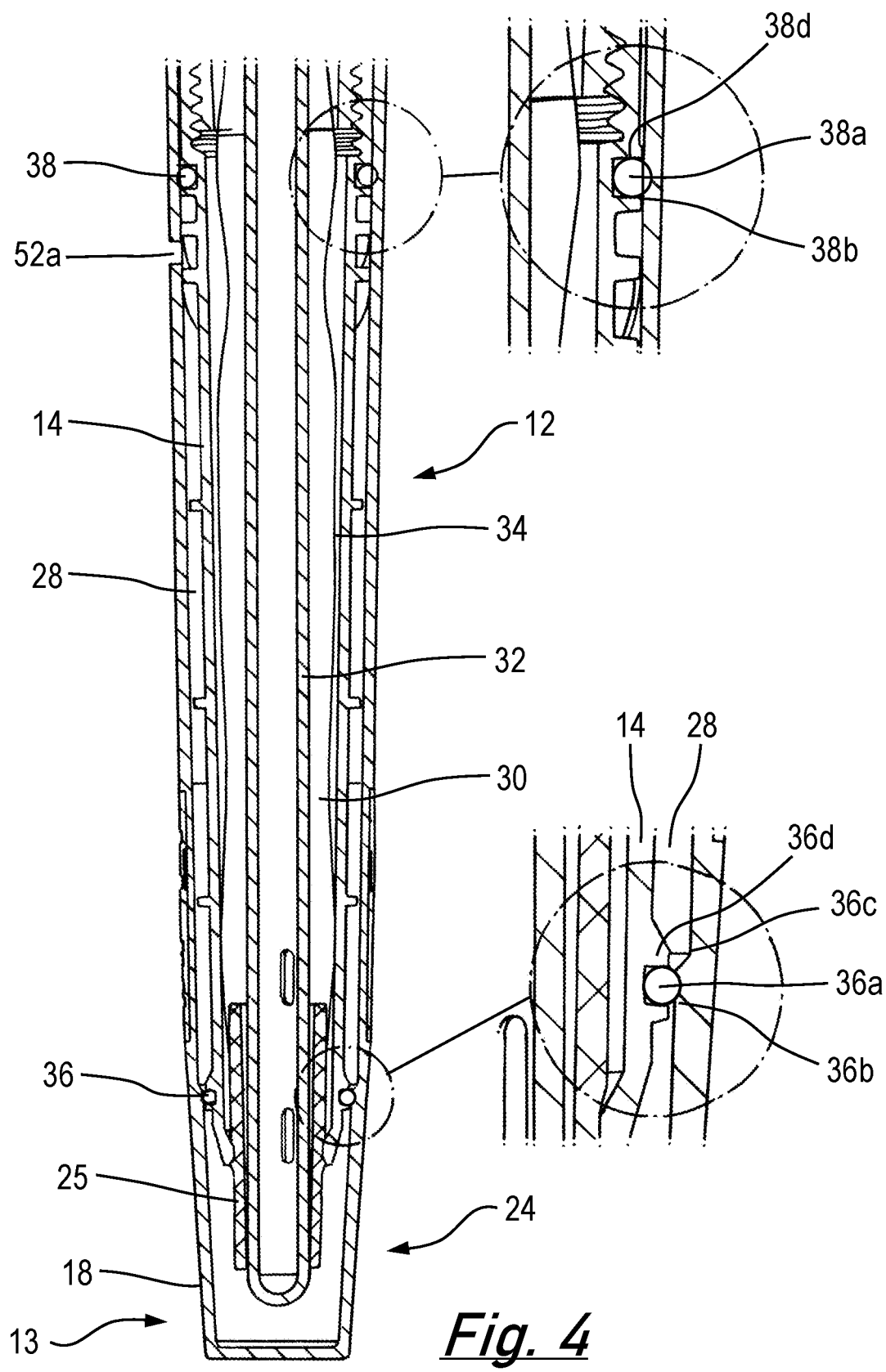
FIG. 4 shows an enlarged longitudinal sectional view of the proximal end of the catheter assembly of FIG. 3 detailing a storage chamber and a wetting chamber.

With reference to FIGS. 1a, 3 and 4, the main body 18 may provide an enclosure which defines a reservoir for a wetting fluid (not shown). The reservoir is formed between the main body 18 and the internal housing 14. Thus, the internal housing 14 may be provided within the external housing 12 in a spaced relation so as to define a cavity 28 therebetween. The cavity 28 may be referred to as a wetting agent storage chamber 28, or simply storage chamber 28 herein. The storage chamber 28 may comprise a first chamber wall provided by the main body 18 and a movable insert provided by the internal housing 14. The internal housing 14 may therefore provide a second storage chamber wall.

The storage chamber 28 is sealed in a first configuration such that the wetting agent is retained therein, and open in a second configuration such that the wetting agent can flow out of the cavity 28 so as to be in flow communication with and, in some embodiments, directly contact an external surface of the catheter tube 32 of the catheter 16.

When in the open configuration, the internal volume of the storage chamber 28 may be in fluid communication with a wetting chamber 30 in which the catheter is located such that the wetting agent can flow from the storage chamber 28 to the wetting chamber 30 and catheter tube 32. In some embodiments, the fluid communication between the storage chamber 28 and wetting chamber 30, may be via one or more valves, inlet channels, or intermediate chambers, such as a priming chamber for example. An example of a priming chamber is described further below.

As shown in FIGS. 1a, 3 and 4, the enclosed volume of the external housing 12 may be partitioned by the internal housing 14 which may be referred to as a movable insert. The internal housing 14 may comprise a tubular wall which is configured to define the wetting agent storage chamber 28 on a radially outer side thereof, and a wetting chamber 30 on a radially inner side thereof.

As shown best in FIG. 4, the internal housing 14 may comprise an elongate thin-walled structure which extends longitudinally along the principal axis 22 of the catheter assembly 10. The internal housing 14 comprises a first end which is distal to the insertion end of the catheter 16 and a second, proximal end which is proximal with respect to, and may surround, the insertion end 24 of the catheter 16. It will be appreciated that the length of the internal housing 14 and the position of the respective distal and proximal ends of the internal housing 14, as well as the separation from the external housing chamber wall, may be varied across embodiments and determined to provide a required volume for the wetting agent storage chamber 28. Further design considerations may arise where the internal housing 14 is configured to act as a pump for pumping the wetting agent from the storage chamber 28 and/or a priming chamber to the wetting chamber during a wetting procedure.

The wetting chamber 30 comprises an elongate cavity between an internal surface of the internal housing 14 and an external surface of the catheter tube 32 such that a wetting agent (not shown) can be provided to the wetting chamber 30 for wetting the exterior surface of the catheter tube 32 prior to use. The wetting chamber 30 may be fully or partially defined by an internal surface of the internal housing 14 and/or an intermediate member such as a sheath 34 which is located within the internal housing 14 and which surrounds the catheter tube 32 during a wetting procedure.

The storage chamber 28 may be an elongate annular cavity which encircles the longitudinal axis 22 and catheter tube 32 and extends axially between a first distal end and a second proximal end. The cavity may be sealed at the first and second ends using one or more seals 36, 38. The seals may comprise seal elements 36a, 38a which may be located between or against corresponding sealing surfaces 36b, 38b. The sealing surfaces 36b and 38b may be provided by corresponding parts of the internal housing 14 and external housing 12. The seal elements 36a, 38a may be elastomeric seals in the form of, for example, an O-ring, X-ring or U-cup seal. The seal elements may extend radially between the internal housing 14 and main body 18.

In order to open the storage chamber 28, the catheter assembly 10 may incorporate one or more valves which may be opened so as to fluidly connect the storage chamber 28 and wetting chamber 30. The one or more valves may be operated by moving the movable insert, e.g. the internal housing 14. The movable insert may be moved by direct manipulation from a user's hand, or by actuating the cap 20. For example, rotating or pulling the cap 20 may cause the one or more valves to open so as to fluidly connect the storage chamber 28 and wetting chamber 30 such that wetting agent can flow from the storage chamber 28 to the wetting chamber 30 and an external surface of the catheter tube 32. The valve may be provided in part by the internal housing 14.

The internal housing 14 may be axially movable along the principal axis 22 of the catheter assembly 10. The axial movement may induce an opening at one or more of the seals 36, 38 which seals the storage chamber 28 such that the opposing seal elements 36a, 38a and sealing surfaces 36b, 38b of the respective seals 36, 38 move from an aligned sealed (or closed) position, to a misaligned non-sealed (or open) position. Thus, for example, partially withdrawing the internal housing 14 from the main body 18 may cause the respective opposing surfaces' seal 36 to move axially in relation to one another and increase the separation of the internal housing 14 and external housing 12 across the seal 36 which provides an opening. As such, one or more of the seals 36, 38 may act as the aforementioned valve(s).

The seal 36 which is configured to act as a valve in this described embodiment may be located proximally such that wetting agent in the storage chamber 28 can flow from the proximal end of the storage chamber 28 into the closed end of the main body 18 of the housing 12. This may be referred to as a priming chamber. From there, the fluid is provided in flow communication with exterior of the catheter tube 32 either directly, or via one more inlets to the wetting chamber 30.

Also shown in FIGS. 3 and 4 is an optional insertion guide 25. The insertion guide 25 is a short elongate annular cuff which resides around a proximal end of the catheter tube 32. The catheter tube 32 is slidably received within the insertion guide 25 such that the insertion guide 25 can move distally when the catheter tube 32 is being inserted. This is described in more detail below.

As noted above, the storage chamber 28 is sealed by a proximal seal 36 and a distal seal 38 to provide an elongate annular cavity in which the wetting fluid can be stored away from the catheter 16. The seals 36, 38 of this described embodiment comprise elastomeric seals in the form of O-rings which are located between opposing sealing surfaces. It will be appreciated that the seals 36, 38 may be alternative annular seals, for example X-rings or U-cup seals. The sealing surfaces are provided by corresponding and radially opposing portions of the internal housing 14 and the external housing 12. It will be appreciated that, more generally, the catheter assembly 10 and storage chamber 28 in particular may be provided with more than one distal seal 38 or proximal seal 36 to provide the necessary sealing function.

One of the sealing surfaces may form part of a seal housing 36d, 38d which retains the seal element 36a, 38a and prevents axial movement of the seal element 36a, 38a. In some embodiments, the seal housing 36d, 38d, may be provided by overmoulding the seal 36, 38 such that it is moulded within a wall portion of the internal 14 or external housing 12. In the example shown, the seal housings 36d, 38d are provided by a wall of the internal housing 14. Hence, the seal housing 36d, 38d restrains the axial ends of the seal elements 36a, 38a such that axial movement of the internal housing 14 relative to the external housing 12 allows the seal 36, 38 to slide with the internal housing 14 along the opposing sealing surface of the external housing 12. It will be appreciated that the seal housing(s) 36d, 38d may be provided by the external housing 12 in some embodiments.

As noted above, the axial movement of the seal 36 may expose or provide one or more outlets for allowing fluid communication between the storage chamber 28 and wetting chamber 30. Additionally, one or more seals may open one or more vents. The vents may act as air inlets configured to allow gas to enter the storage chamber 28 to replace the wetting agent as it exits the storage chamber 28. The vents may be internal so as to open the storage chamber 28 to another internal cavity, or external so as to draw air in directly from the exterior of the assembly 10.

As shown in the embodiment of FIG. 4, the proximal seal 36 may be located adjacent a divergent portion 36c in the storage chamber 28. The divergent portion corresponds to an increased separation between the external housing 12 and the internal housing 14, which may be provided by a step or taper in the profile of the respective surface of the internal housing 14 and external housing 12. Hence, a seal 36 of the storage chamber 28 may be located at a local restriction between the opposing walls of the storage chamber 28.

The divergent portion provides a space into which the seal 36 can be moved when the storage chamber 28 is opened. Hence, when the internal housing 14 shown in FIG. 4 is moved distally (so as to rise in the image as shown), the seal 36 moves into the wider chamber portion, thereby opening a flow path from the storage chamber 28 into the proximal end of the main body 18. As such, the seal 36 operates as a valve and the insertion end 24 of the catheter 16 may be submerged in wetting agent which has flowed from the storage chamber 28. As can be seen in FIG. 4, although both the internal housing wall and external housing wall comprise steps/tapered portions which contribute to the divergence of the storage chamber 28, it is the wall which comprises the sealing surface 36b against which the seal element 36a urges and moves against that provides the separation.

The distal seal 38 of the storage chamber 28 is axially spaced from the proximal seal 36 along the internal housing 14 and provided in a fixed location relative to the proximal seal 36. The distal seal 38 may include a seal housing 38d similar to the one provided for the proximal seal 36 such that axial movement of the internal housing 14 results a translation of the seal element 38a along the length of the external housing 12. The distal seal 38 in the embodiment of FIG. 4 differs from the proximal seal 36 in that the seal surfaces are substantially uniformly spaced and the seal surface 38b which opposes the seal housing 38d and the active sealing surface of the seal element 38a remains in contact with the seal element 38a upon displacement of the internal housing 14. As such, the distal seal 36 may remain in-tact as the internal housing 14 is displaced and the proximate seal valve opened. As noted above, the axial movement of the proximal seal 38 may result in one or more vents being exposed and/or opened.

The internal housing 14 may be configured to provide pump for pumping the wetting agent into the wetting chamber 30. As such, the distal seal 38 may be configured to maintain a higher pressure than proximal seal 36 which is configured to maintain the integrity of the storage chamber 28 when the assembly is stored and transported prior to use. As can be seen in FIG. 4, the distal seal element 38a may be larger than the proximal seal element 36a.

As can be seen from FIG. 5, the distal seal 38 of the storage chamber 28 may be axially spaced from the open distal end of the main body 18. The extent of the distance may correspond to or be greater than the throw (axial movement) of the internal housing 14 when undergoing a wetting or priming operation. Hence, following a full movement of the internal housing 14, the distal seal 38 may remain in contact with the wall of the external housing 12.

Figure 7:
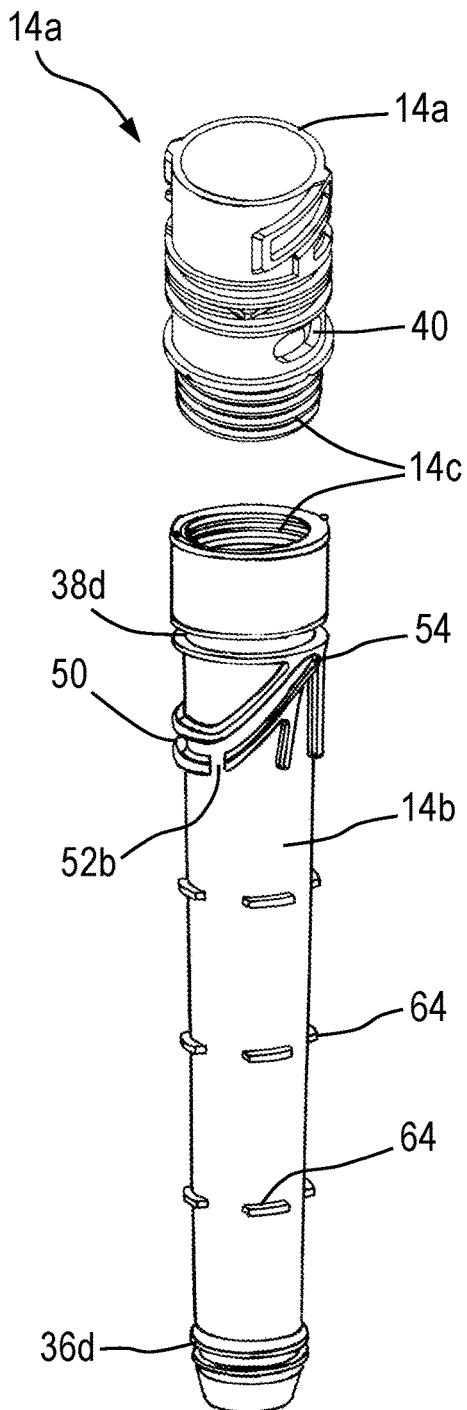
FIG. 7 show a perspective view of an internal housing which may be used in the catheter assembly of FIG. 1.

FIG. 7 shows an exploded view of an embodiment of the internal housing 14 which comprises first 14a and second 14b parts joined together by a screw threads 14c. It will be appreciated that the specific construction of internal housing 14 may vary and it may, in some embodiments, be provided by a unitary structure or parts which are joined using alternative methods, such as a push fit or bayonet construction.

As can be seen from FIG. 7, one or more vents 40 may be provided in the sidewall of the internal housing 14. The one or more vents 40 may provide an outlet for the wetting chamber 30 such that air displaced from the wetting chamber 30 when wetting agent flows up or into the wetting chamber 30 can escape.

In some embodiments, the opening of the storage chamber 28 may be sufficient to wet the catheter, in which case, once the wetting chamber 28 has been opened, it may be sufficient to withdraw the catheter 16 for use (optionally inverting the assembly between opening the chamber and withdrawing the catheter, in order to ensure adequate distribution of wetting agent). In some embodiments, the wetting procedure for wetting the catheter 16 may include a pumping or plunging action in which wetting agent is pneumatically and/or hydraulically driven from the storage chamber 28 into and along the wetting chamber 30.

In the embodiment shown in FIG. 1, the pumping action may be provided by the axial movement of the internal housing 14 within the external housing 12. The internal housing 12, acting as a movable insert, may be configured to move axially to reduce the volume of the storage chamber 28 thereby pumping/driving a flow of the wetting agent into the proximal end and the wetting chamber 30 so as to wet the catheter.

Figure 6A:
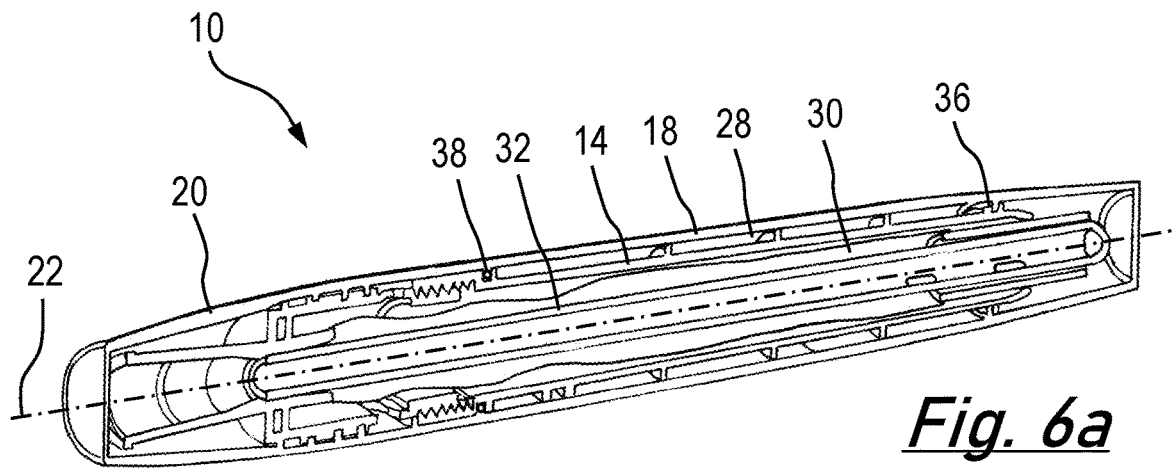
FIGS. 6a to 6c show a sequence of longitudinal sections of the catheter assembly of FIG. 1 highlighting the wetting procedure for the catheter.
Figure 6B:
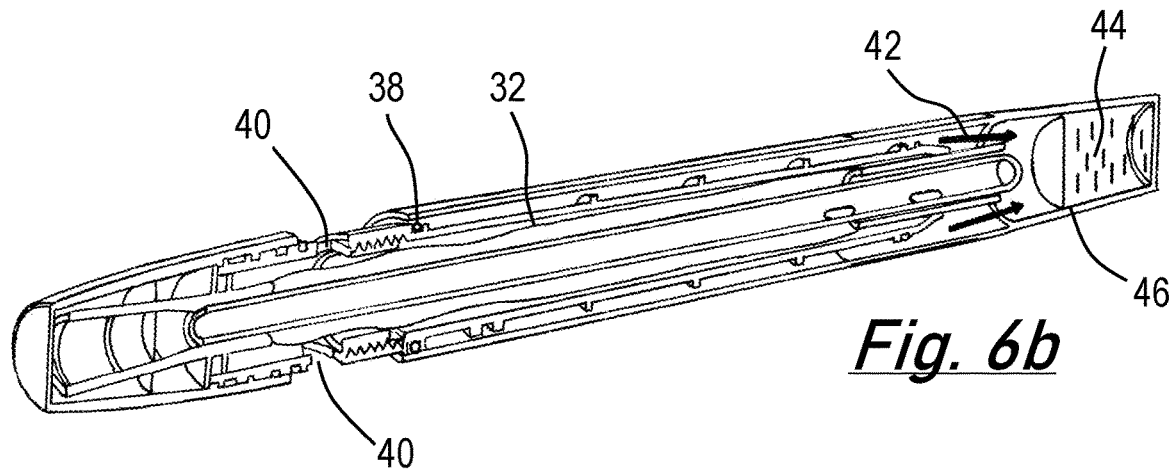
Figure 6C:
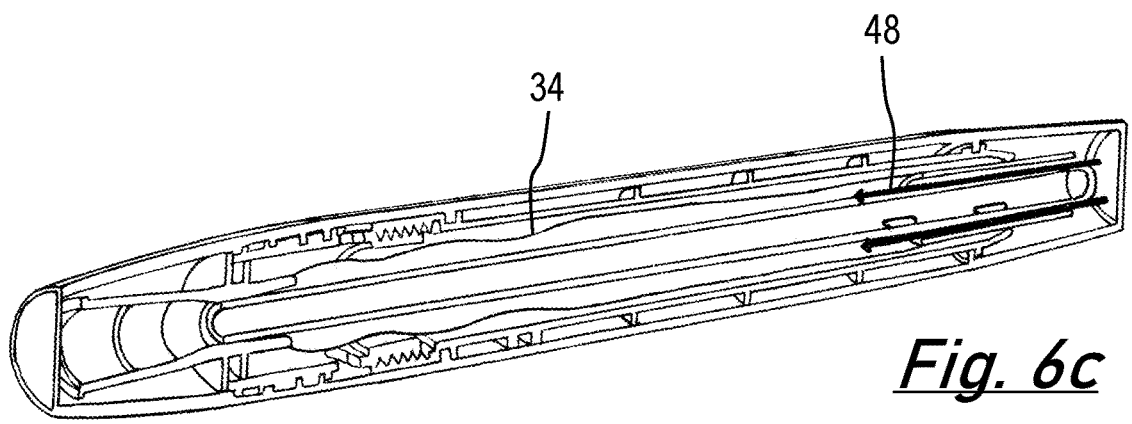

FIGS. 6a to 6c show a wetting operation of the catheter assembly 10 in which the internal housing 14 is moved distally and axially along the longitudinal axis 22 from a first position to a second position resulting in an opening of the storage chamber 28 and subsequent driving of the wetting agent distally along the catheter tube 32. FIGS. 6a to 6c show the actuation of the assembly with the cap 20 place, however, it will be appreciated that this may not be the case in some embodiments and the cap 20 may be fully removed. Further, the catheter assembly 10 is shown as being horizontal, but the assembly may be operated in a vertical orientation.

The wetting operation involves three primary phases. The first phase, shown in FIG. 6a is a closed or sealed configuration/position in which the cap 20 is retained on the main body 18 of the housing 12 for storage and transportation purposes and the storage chamber 28 is sealed and includes the wetting agent. In FIG. 6b, the cap 20 is released from the main body 18 and the internal housing 14 moved axially and distally via the cap 20 such that the proximal seal 36 element moves away from the opposing seal surface provided by the main body 18 and a flow path 42 opens to allow wetting agent 44 held in the storage chamber 28 to be moved into the proximal end of the main body 18. This may be referred to as a priming phase or charging phase in which the wetting chamber 30, or an associated priming ante-chamber 46 is primed with the wetting agent ready to be driven along the catheter tube 32. FIG. 6b may be referred to as a priming configuration or priming position.

When the movable insert i.e. the internal housing, is in the primed position, it is to be noted that the distal seal 38 maintains contact with the inner wall of the main body 18 such that the leakage of wetting agent from the storage chamber 28 to the exterior of the catheter assembly 10 is prevented. However, one or more vents may be provided at the distal end of the storage chamber 28, configured to allow gaseous communication between the storage chamber 28 and remainder of the catheter assembly 10, when the internal housing is in the primed position, one or more channels arranged between the storage chamber 28 and the vents are opened which allows gas (i.e. air) to enter the storage chamber to displace the wetting agent. Typically the assembly will be held vertically, or at least with the closed end of the main body lower than the cap, such that gravity assists in allowing wetting agent to move into the closed end of the main body and the priming chamber. Optional ribs 64 discussed below also assist in allowing wetting agent to move from the storage chamber 28 to the priming chamber.

Once the wetting agent 44 has moved into the closed end of the main body 18 and the priming chamber, the internal housing 14 can be re-inserted into the main body 18 such that the wetting agent is forced up fluid path 48 via an inlet to the wetting chamber 30 between the internal housing 14 and catheter tube 32. Air displaced from the wetting chamber 30 can exit from a suitable outlet which exhausts the displaced air outside of the catheter assembly. FIGS. 6c and 7 provide examples of suitable outlets in the form of openings 40 which are provided in the internal housing wall and located between the distal end of the internal housing 14 and distal end of the main body 28 so as to be exposed externally. There are two diametrically opposed openings 40 in the embodiment shown, however, there may be fewer or greater than two openings 40. It will be appreciated that the size, shape and position may also differ. The openings 40 shown in the embodiment are oval having a major axis extending circumferentially to allow a larger aperture for a reduced axial length.

The inlet to the wetting chamber 30 from the storage chamber 28/priming chamber 46 may be provided via the separation between the internal housing 14 and catheter tube 32. In the embodiment shown in FIGS. 6a to 6c, there is a sheath 34 surrounding the catheter tube 32 which may form and at least partially define the wetting chamber 30, or may be provided within the wetting chamber. In this case, the inlet to the wetting chamber may be provided between the catheter tube 32 and sheath 34. Additionally, or alternatively, where an insertion guide 25 is included, the inlet may be determined by the separation between the insertion guide 25 and catheter tube 32. In a further alternative, for example with no sheath 34, the wetting chamber may be at least partially formed and defined by the inner surface of the internal housing 14. The inlet may be defined by the separation between the bottom end of the internal housing 14 and the catheter tube 32.

In some embodiments, the internal housing 14 may be reciprocated upon rotation of the actuator and thus moved back and forth several times. However, it will typically be sufficient to undertake a single distal-proximal cycle to create a sufficient wetting of the catheter tube 32, thereby using the internal housing as a plunger.

As noted above, the plunging action of the internal housing 14 may be achieved by hand such that a user directly manipulates the internal housing 14 distally and proximally along a linear axial path by pulling and pushing on the internal housing 14 whilst restraining the external housing 12. However, in some embodiments it may be preferable to drive the movement of the internal housing 14 with an actuator.

The actuator, which may be referred to as a priming mechanism, may be any device which can cause the required axial movement of the internal housing 14. The internal housing 14 may be configured to move axially when rotated. In some embodiments, the actuator may comprise a cam-drive or crank in which rotational movement of the internal housing 14 is used to drive the linear, axial motion of the internal housing 14 relative to the main body 18. The rotational movement of the internal housing 14 may be provided by a rotatable actuator in the form of a rotating cap 20, for example.

In some embodiments, the rotation of the cap 20 may be used to drive the linear movement of the internal housing 14 and also to remove the cap 20 from the main body 18. Thus, the rotation of the cap 20 may comprise a first stage and a second stage. The first stage may correspond to the driving of the internal housing 14 to open the storage chamber 28 and to pump the wetting fluid around the catheter tube 32. The second stage may correspond to the releasing of the cap 20 from the main body 18 to expose the catheter 16 for use.

The simultaneous rotational and axial movement of the internal housing may be provided by one or more drive surfaces which are driven by a corresponding driving element. For example, the chamber wall provided by the external housing or the internal housing may comprise one or more axially and circumferentially extending drive surface. The other of the chamber wall and movable insert may comprise a driving element which engages with the drive surface to provide the axial movement of the movable insert upon relative rotation of the movable insert and chamber wall. The drive surface may comprise a first axially facing surface provided by a radially projecting flange, rib, thread, track or rail. The driving element may comprise a second axially facing surface of a radially extending flange, rib, thread, track, rail or pin. The drive surface and driving element may be referred to as a cam drive.

Figure 8A:
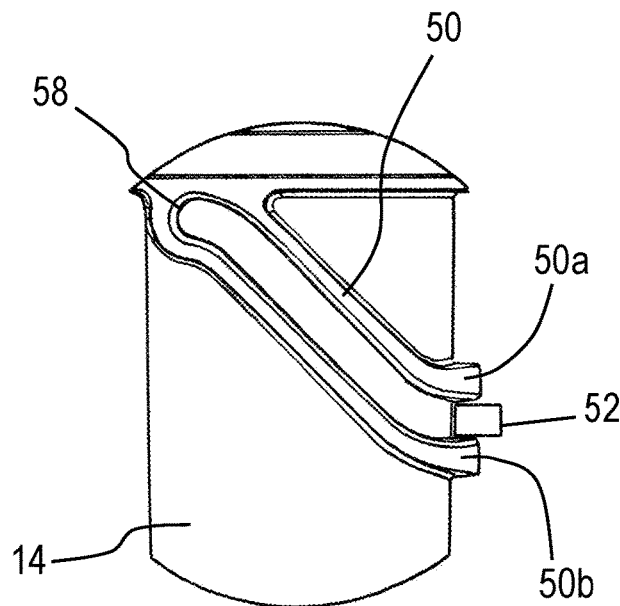
FIGS. 8a and 8b show, respectively, a side view and flattened front view schematic of a plunger track provided by the internal housing of FIG. 7.
Figure 8B:
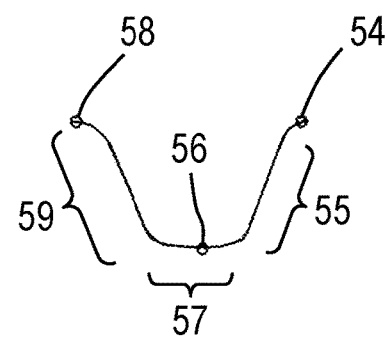

An embodiment of an actuator/priming mechanism having a drive surface and driving element will now be described in connection with FIGS. 7, 8*a* and 8*b*. FIG. 7 shows a perspective exploded view of the internal housing 14 which is described in part above. FIG. 8*a* shows a side view of a drive surface in the form of a plunger track portion of the internal housing, and FIG. 8*b* shows a schematic flattened front view of the plunger track 50 demonstrating a general shape a plunger track may have.

FIG. 7 shows a perspective view of the internal housing 14 in which there is provided an elongate thin-walled enclosure having respective seal housings 36*d* and 38*d* of a proximal seal 36 and distal seal 38 of the storage chamber 28 provided at opposing ends of the housing 14. The external surface of the internal housing 14 comprises a drive surface in the form of a track 50, which may be referred to as a plunger track, which engages with a corresponding driving element 52 (FIG. 8*a*) appended to the external housing 12 (not shown). As shown, the plunger track 50 may include a channel which receives the driving element 52 in the form of a projection, e.g. a pin, which extends from an internal surface of the external housing 12, or an intermediate member. The channel may be provided by a pair of axially separated guide rails in the form of radially projecting walls 50*a*, 50*b* which extend from the exterior surface of the internal housing 14. The walls 50*a*, 50*b* may be parallel and join to form a closed track. However, in some embodiments, the track 50 may comprise partial walls in accordance with the direction of actuation required. That is, where the internal housing is urged distally, only the distal wall may be required to provide the necessary drive surface, and vice versa.

It will be appreciated that, in some embodiments, the track 50 may be provided on the interior surface of the external housing 12 and correspondingly the driving element 52 may be appended from the exterior of the internal housing 14. It will also be appreciated that the plunger track 50 and driving element 52 may comprise any suitable features for allowing the necessary driving engagement which translates the rotational movement of the internal housing 14 into an axial movement. Thus, the track 50 and driving element 52 may comprise any combination of a channels, grooves, ridges, protuberances, recesses, notches, bearings and gears, amongst others to provide the drive surface and driving element.

The track 50 is provided proximally of the distal seal 38 such that it is located within the storage chamber 28. Providing the plunger track 50 within the storage chamber 28 is optional and it may, in some embodiments be provided either distally or proximally of the distal 38 and proximal 36 seals. However, providing the plunger track within the storage chamber 28 may allow the overall length of the assembly 10 to be shorter and may provide a convenient point to fill the storage chamber 28 with wetting agent, as discussed further below.

In some embodiments, the catheter assembly 10 may comprise a filling aperture in the external housing such that wetting agent can be introduced to the storage chamber 28 once the catheter assembly 10 has been assembled. Thus, the aperture may be provided in flow communication with the storage chamber 28. Returning to FIG. 4, there is shown an aperture 52*a* which extends through the wall of the external housing 12, e.g. the main body 18, so as to provide access to the storage chamber externally to the catheter assembly 10. The aperture 52*a* may be configured to receive any suitable nozzle or attachment which is connected to a source of wetting agent and may be referred to as a port. It will be appreciated though that the aperture 52*a* may be a conventional round through-hole.

The positioning of the filling aperture 52*a* in the described embodiment is such that it overlays the track 50, such that, following a filling procedure, the driving pin 52 can be inserted (and optionally welded in place) to plug the filling aperture 52*a* whilst extending into the track 50 so as to fulfil the function of a driving element 50. It will be appreciated that the filling aperture may simply be plugged in other embodiments and the plug may not provide a driving element 52 for the actuator for moving the movable insert.

As shown in FIG. 4, although the internal housing 14 is generally spaced from the external housing 12, the internal housing 12 may be snugly received within the external housing 12 such that there is minimal clearance between the outer edge of the track 50 and/or ribs and the internal surface of the external housing 12. Providing a minimal clearance allows the track 50 and/or ribs 64 to keep the internal housing concentric to the external housing when being moved.

To allow the wetting agent to flow from the aperture 52*a* into the storage chamber 28, the proximal rail of the track 50 may comprise a discontinuity, e.g. an aperture 52*b*, as can be seen schematically in FIG. 7. There may be a plurality of discontinuities so as to provide a 'hyphenated' guide rail. It will be appreciated that any aperture or discontinuity will typically be provided on a non-drive surface which does not require contact with the driving element 52 to actuate the axial movement of the internal housing 14. In some embodiments, there may be no drive surface on the proximal side of the aperture, particularly where the reactive force for axially translating the movable insert is required on the distal side of the driving element 52.

As best seen in the schematic view of FIG. 8*b*, the plunger track 50 is elongate and extends from a first endpoint 54 which corresponds to the closed configuration or position, to a mid-point 56 which corresponds to the primed configuration or position, to a second endpoint 58 which corresponds to the post-plunged wetted configuration or position. The track 50 may be generally cosine or U-shaped extending from the first end 54 at a distal-most location to the second point 56 at a proximal-most location to the third point 58 at the distal-most location which is angularly (circumferentially) spaced from the first point.

The separation between the respective adjacent points 54, 56, 58 provide the axial movement of the internal housing 14 as the internal housing 14 is rotated. Thus, the section 55 between the first end point 54 and mid-point 56 define, at least in part, the priming movement of the internal housing 14 in which the proximal seal 36 is opened. The end section 59 between the mid-point or primed position 56 and second end point or post-plunged wetted position 58 corresponds to the pumping movement in which the internal housing 14 is reinserted to drive the wetting agent from the priming chamber to the wetting chamber 30. The intermediate section 57 corresponds to the primed position in which the internal housing 14 extends out of the external housing 12 with the proximal seal open such that the wetting agent can flow into the priming chamber 56.

The track 50 may be continually curved or comprise one or more straight portions. For example, as can be seen in FIG. 8*b*, the track 50 comprises straight portions for the first 55 and final sections 59 which represent the majority of the transitions between the distal-most and proximal-most positions of the internal housing 14. The lower portion of the track 50 is broadly flat with little to no axial displacement and so provides a dwell period in which the internal housing 14 is rotated in the open configuration to provide sufficient time for the wetting fluid to drain from the storage chamber 28 into the priming chamber 46 provided at the proximal end of the main body 18.

It will be appreciated that the term "straight portion" used above refers to the axial trajectory of the track 50 as revealed by the front-on view taken when the track 50 is flattened out, as provided in FIG. 8*b*. The track 50 itself will continuously curve due to it extending circumferentially around the longitudinal axis 22.

The terminal ends 54, 58 of the track 50 may be provided with a change in trajectory such that the speed of the axial movement along the longitudinal axis 22 may be reduced when the movement is commencing and terminating to provide an improved tactile experience for the user. That is, leading into the actuation and out of the actuation with a reduced acceleration and deceleration may provide a less abrupt start and finish to the actuation and provide an improved user experience. Moreover, a lower axial movement may offer a mechanical advantage as movement commences, against the resistance to axial movement caused by the seals.

In use, the internal housing 14 is rotated such that the driving element 52 travels along the track 50. As the driving element 52 is held in a stationary relation to the external housing 12, rotation of the internal housing 14 results in a linear movement along the longitudinal axis 22 of the catheter assembly 10. The initial phase of the movement in the proximally extending portion of track 50 results in a distal movement of the internal housing 14 so as to open the proximal seal 36, as described above. From there, the driving element 52 enters the rotation portion 57 in which the wetting agent 44 drains out of the storage chamber 28 with a reduced amount of axial movement, which is then followed by the third portion 57 of the track which drives the internal housing distally and towards the priming chamber.

The arrangement of the track 50 is such that rotating the internal housing 14 in a single direction for a predetermined angular extent, i.e. a given rotation of the cap 20, causes a full linear cycle of movement. The predetermined angular extent may be any which is considered appropriate for the cap 20 and user experience.

The terminal end of the track 58 is provided with a closed end such that further rotation of the internal housing is not possible once the driving element 52 contacts the closed end. As such, the actuator may be provided with a mechanical stop or rotational limiter which limits the rotation of the internal housing. This can provide mechanical feedback to the user to indicate that the priming and/or wetting phase of the catheter has been achieved and the catheter can be removed. Following the mechanical feedback, the cap 50 can be removed and catheter 16 withdrawn for use.

It will be appreciated that the extent of the rotation will determine the amount of force required to move the internal housing. Thus, a short angular extent, for example 90 degrees, will result in a faster movement of the internal housing and will require a greater force when compared with a longer rotation of, for example, 270 degrees. The range of angular movement may be between 90 degrees and 360 degrees.

In embodiments where the rotation of the internal housing 14 relative to the main body 18 is achieved via the cap 20, the cap 20 and/or internal housing may comprise one or more interlocks to rotationally engage the cap 20 and internal housing 14. There may be a plurality of interlocks which may be distributed circumferentially about the cap 20 on the internal surface thereof.

Figure 9A:
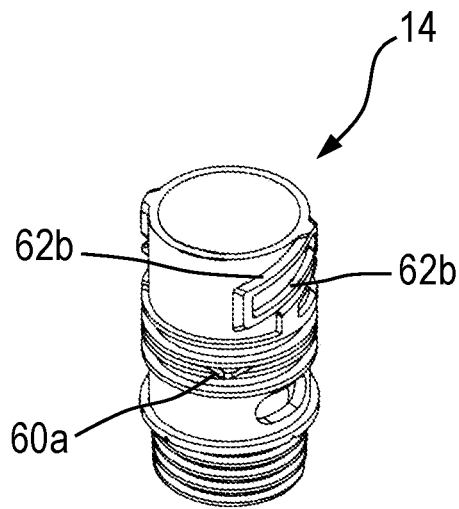
FIGS. 9a to 9c show an upper portion of the internal housing and details of a cap which may be used with the catheter assembly shown in FIG. 1.
Figure 9C:
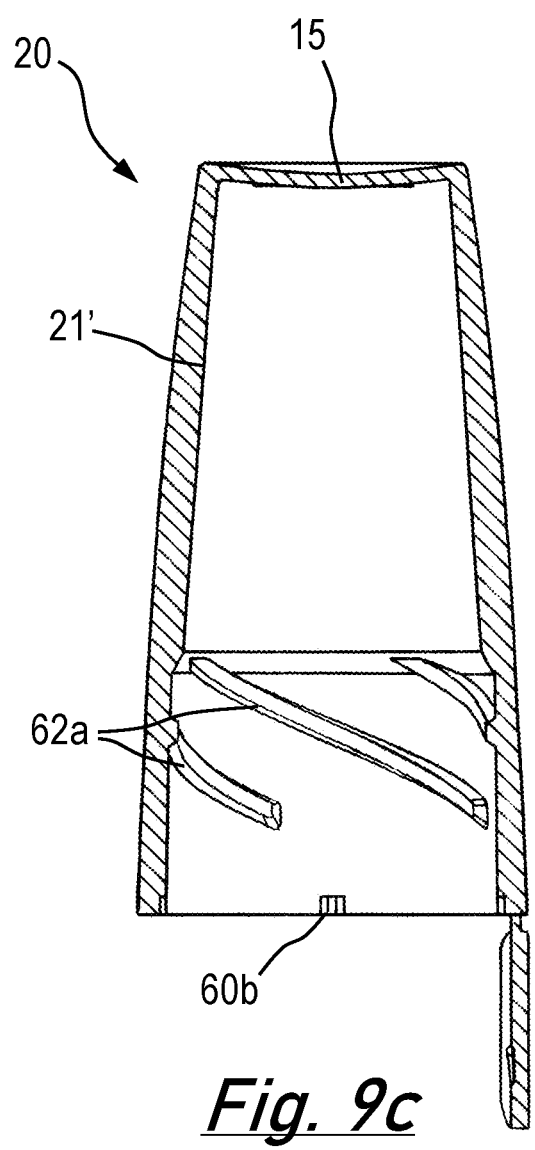
Figure 9B:
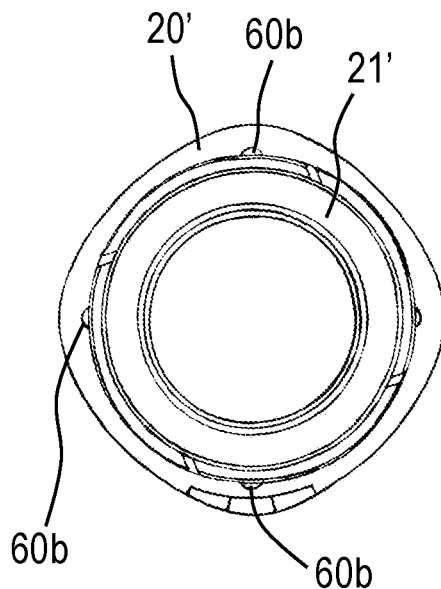

Referring to FIGS. 9*a* to 9*c*, it can be seen that an interlock may be provided by respective interengaging projections 60*a* on an external surface of the internal housing 14 which are received within corresponding recesses 60*b* in the internal surface of the cap 20. As can be seen, there may be a plurality of interlocks 60*a,b* evenly distributed about the periphery of the cap 20 and internal housing 14 to provide multiple points of engagement. The embodiment shows four interlocks, however, there may be greater than or fewer than this. The recesses 60*b* are shown as being provided in the thicker section of the cap 20 wall so as to maintain a minimal thickness at the proximal edge and provide the necessary the hoop strength. However, this is not a limitation and the recesses 60*b* may be provided in different or other circumferential locations.

The interlocks 60*a,b* may comprise a torque activated release such that, upon reaching a predetermined threshold of rotating torque on the cap, the interlocks release allowing the cap 20 to rotate relative to the internal housing 14. Thus, once the travel of the driving element 52 reaches the end of the drive surface and engages the rotational limiter, an increased torque and continued rotation of the cap 20 overcomes the interlocks and allows the cap 20 to rotate relative to the internal housing 14. Once released, the further rotation of the cap 20 may allow the cap 20 to be removed.

To provide the torque activated release, the interlocks may comprise shapes which are configured to disengage beyond a given torque. The shape of the projections 60*a* and recesses 60*b* may correspond to one another such that the surfaces of the recesses 60*b* are provided in intimate contact with the projections 60*a*. When viewed in plan, it can be seen that the contacting surfaces are inclined relative to the tangent at the respective locations such that the projections are triangular. Providing tangentially inclined surfaces contacting surfaces in this way provides a convenient way to control the torque threshold the interlocks can withstand before releasing, allowing the interlocks to release when the driving element 52 reaches the terminal end 58 of the plunger track 50.

The recesses 60*b* and projections 60*a* may be configured to prevent rotational separation only, with axial engagement between the internal housing 14 and cap 20 being provided by other features. Hence, as shown in FIG. 9*c*, the recesses 60*b* may be provided in the proximal edge of the cap 20 adjacent to the open end. This provides the recesses 60*b* with an open end along the axial direction.

To prevent the cap 20 being pulled axially off the internal housing 14 in a distal direction, the cap 20 and/or internal housing 14 may comprise an axial retention feature which retains the relative axial position with the internal housing 14 whilst the cap 20 is being rotated. In the described embodiment, the axial retention feature is provided by a screw thread 62*a* which engages with a screw thread 62*b* on an external surface of the internal housing 14. The screw thread may be used to remove the cap 20 from the internal housing 14 once the plunging action is complete and the torque threshold has been overcome. Removing the cap 20 from the screw thread may expose the catheter for a user to handle.

The screw threads 62*a,b* may comprise partial turn or full turn threads. The partial turn threads may comprise, for example, a quarter turn thread in which the cap 20 is removed following a quarter turn of the cap 20 following the rotational disengagement from the internal housing 14.

As noted above, the rotation of the cap 20 may comprise a plurality of stages. The rotation of the cap 20 may comprise a priming step and a removal step. The priming step and removal step may be sequential and be achieved by rotating the cap 20 in the same rotational direction. The sum of the first and second steps may correspond to the number or turns required to remove the wet the catheter and remove the cap 20. For example, a full 360 degree rotation of the cap 20 may result in the wetting and removal of the cap 20. The wetting phase may comprise a 270 degrees, or three-quarter turn and the removal of the cap 20 may comprise a further quarter turn. Other combinations of turns and turn steps may be possible.

The driving element may comprise a plug which is received within a filling orifice of the storage chamber 28. Thus, the main body 18 may comprise at least one aperture extending through an external wall thereof, the aperture providing access to the internal volume of the storage chamber 28 such that the wetting fluid may be received via the aperture. The aperture may be configured to receive the driving element/plug 52 following the filling procedure. Thus, the aperture may oppose the first end 54 of the track.

The internal volume of the catheter assembly may be sterilised following assembly. In order to preserve the sterility of the internal volume the catheter assembly may comprise a hermetic seal. The hermetic seal may comprise an external surface of the catheter assembly or may comprise one or more seals located within the cap 20 and/or main body 18. The hermetic seal may be broken by rotation of the cap relative to the main body. Returning to FIG. 5, there are shown hermetic seals 66 and 68 provided on either side of the joint between the main body 18 and cap 20. The seals 66 and 68 may be similar to other seals described herein and comprise elastomeric seal elements held within a seal housing.

The hermetic seals 66 and 68 may be broken when the cap 20 is removed from the main body 18. Thus, rotating the cap 20 to initiate transitioning from the sealed configuration to the primed configuration may break (i.e. open) the seal 66 or 68. In the case where the internal housing 14 is moved distally with the rotation of the cap 20, the seal 68 will open initially, thereby breaking the hermetic seal before the cap 20 is actually separated from the internal housing. However, the distal seal 38 will prevent the wetting agent leaving the distal end of the storage chamber, thereby rendering the catheter assembly in a primed by leak-resistant configuration. This is advantageous as it allows the catheter assembly 10 to be left temporarily once primed such that a user might put the catheter aside for a short time once opened, for example, to adjust position and/or clothing (or even for longer, to answer the door, say, before returning to catheterisation) prior to removing the catheter from the external housing.

Returning to FIG. 7, it can be seen that the internal housing 14 may be provided with optional ribs 64. The ribs 64 may be included to maintain the separation of the internal housing 14 and external housing 12 which defines the storage chamber 28. Hence, when ribs 64 may assist in guiding the internal housing 14 when moved axially and rotationally. The ribs 64 may also aid with the pumping action of the internal housing 14 when it is reinserted into the external housing 12. Thus, the ribs 64 may act to drive the wetting agent proximally into the closed end and up the wetting chamber 30.

The ribs 64 may extend circumferentially around the internal housing 14. The ribs 64 may be discontinuous in the circumferential direction such that a flow path may be maintained between adjacent ribs 64. As can be seen, the ribs 64 may be provided along the length of the internal housing 14. In the embodiment shown there are three sets of ribs 64 disposed at regular intervals along the length of the internal housing 14. Each set of ribs 64 includes four separate circumferential sub-ribs provide at common axial locations above a circumferential line with the ribs having the same angular length. It will be appreciated that the specific arrangement of the ribs may vary in other embodiments.

The sequential priming, wetting and cap removal rotation is shown in FIGS. 10*a* to 10*f* which show the major steps for removing a catheter from an embodiment catheter assembly.

FIG. 10*a* shows the catheter assembly 10 in a closed, pre-activation configuration in which the hermetic seal is intact and the interior cavity of the external housing 12 is sterile. FIG. 10*b* shows a first step in which the cap 20 is turned through an initial rotation phase. The initial rotation of the cap 20 rotates the internal housing 14 via the rotational engagement provided by the interlocks 60*a* and 60*b*. The rotation of the internal housing 14 causes the drive surface provided by track 50 and driving element 52 to move the internal housing 14 in an axially distal direction, together with the cap 20. As can be seen in FIG. 10*c*, the distal movement of the internal housing 14 opens the hermetic seal 68 and the proximal seal element 36*a* transitions of the divergent portion so as to open a flow path for the wetting agent, as seen in FIG. 10*d*. At this point, the wetting agent flows into the priming chamber 44 at the proximal end of the main body 18 and the catheter assembly is primed. A continued rotation of the cap 20, moves the internal housing 14 back into the main body 18 at which point the ribs 64 pump the wetting agent from the priming chamber 44 up the wetting chamber inlet provided between the internal housing and insertion guide (if present) and the catheter tube 32. Once the driving element 52 reaches the end of the drive surface provided by track 50, further rotation is not possible without an increase of torque. Thus, the user is provided with some mechanical feedback that the catheter 16 has been wetted. The above actions are carried out with a single user action, i.e. the rotation of the cap 20 in a common direction using a substantially constant torque.

Following this first rotational step of the cap 20, the cap 20 is further rotated releasing the torque activated release interlock thereby allowing the cap 20 to move relative to the internal housing 12 via the threads 62*a,b*. Following the removal of the cap 20, the catheter 16 may be grasped by the external handling surfaces on the outlet end 26 of the catheter 16 and withdrawn axially, ready for use. Where a sheath 34 has been employed, this will be in a deployed position with the catheter 16 located therein to preserve the sterility thereof during manipulation.

Referring to FIGS. 1 and 3, the catheter 16 may be any suitable catheter known in the art. As shown, the catheter 16 may comprise a catheter tube 32, and a funnel 26.

The catheter tube 32 may be an elongate thin-walled structure which extends longitudinally along the principal axis 22 of the catheter assembly 10. The catheter tube 32 may be comprised of a flexible material. A first end of the catheter tube 32 may be closed with a hemi-spherical cap, and form the insertion end 24 of the catheter 16, the hemispherical shape aiding with insertion.

Proximate to the insertion end 24 there may be provided one or more drainage apertures 33, in this embodiment the drainage apertures 33 are oval in shape with the major axis being parallel with the principal axis 22. It will be appreciated that the size and shape of the drainage apertures 33 may differ.

The exterior surface of the catheter tube 32 may be, as is known in the art, functionalised. such that when wetted by the wetting agent the co-efficient of friction of the catheter tube 32 is reduced. The outer surface of the catheter tube 32 may be comprised of, or coated in, a functionalising material; for example the outer surface of the catheter tube 32 may have hydrophilic properties. The hydrophilic properties serve to reduce the coefficient of friction of the outer surface when the wetting agent is introduced.

The end of the catheter 16 distal to the insertion end 24 is provided with a catheter outlet end 26. In this embodiment the catheter outlet end 26 is provided as a funnel 26 and is a separate component to the catheter tube, in other embodiments they may be integrally formed. The funnel is cylindrical in shape having a first open end and a second open end. The first open end is configured to receive the catheter tube 32 by the end distal to the insertion end 24. The catheter 16 is configured to provide fluid communication between the drainage apertures 33 and the catheter outlet end 26.

Projecting radially from the exterior surface of the funnel 26 there may be one or more projecting ribs. In the embodiment of FIG. 4 there are provided two projecting ribs; the first rib 35a is arranged proximate to the second end of the funnel and the second rib 35b is arranged between the first rib 35a and the first end of the funnel. The second rib 35b is sized such that its external diameter corresponds to the internal diameter of the distal end of the internal housing 14. The first rib 35a is sized such that its external diameter is greater than the internal diameter of the distal end of the internal housing 14 and less than the internal diameter of the open end of the cap 20. The arrangement of the two projecting ribs 35a,b may be provided to maintain the position of the catheter 16 relative to the internal housing 14; the second rib 35b ensuring the catheter 16 and internal housing 14 are arranged coaxially, and the first rib 35a limiting the extent to which the catheter 16 can be inserted into the internal housing 14 proximally along the principal axis 22.

A region of the exterior surface of the funnel between the second end of the funnel and the first rib 35a may be textured to provide a gripping surface for a user. Where the exterior surface of the funnel between the second end of the funnel and the first rib 35a is used as a gripping surface, the projecting ribs 35 fulfil an additional function, providing separation between a user's fingers and the (wetted) catheter tube 32.

As noted above, FIGS. 1 and 3 also show an optional sheath 34. The sheath is formed of a flexible material and is arranged surrounding the catheter tube 32. The sheath is coupled at a first end to the funnel proximate to the first open end thereof, and at a second end to the insertion guide 25. The insertion guide 25, or part thereof, is comprised of an elastically deformable material.

In use, after completing the wetting cycle and removing the cap 20, a user withdraws the wetted catheter 16 from the catheter assembly 10. Holding the gripping surface of the funnel 26 and where present, the insertion guide 25, the user directs the catheter tube 32 into a canal, vessel, passageway, body cavity, etc. for removal of fluid therefrom.

Where the sheath 34 and insertion guide 25 are present, the user grips the insertion guide 25 to guide the catheter tube 32. The user squeezes the insertion guide 25, deforming it such that it engages with the catheter tube 32, restricting axial motion of the catheter tube 32 through the insertion guide 25 and inserts a first section of the catheter tube 32 exposed from within the sheath 34 into the canal, vessel, passageway, body cavity etc. Once the first section of the catheter tube 32 has been inserted, the user relaxed their grip on the insertion guide 25, allowing it to return to its original shape, and slidably draws the insertion guide 25 along the catheter tube 16 away from the insertion end 24, furling a portion of the sheath 34 and exposing a second section of the catheter tube 16. The process is then repeated, with the user squeezing the insertion guide 25 to restrict the motion of the insertion guide 25 with respect to the catheter tube 16 and the second section of the catheter tube inserted. The process is repeated until the catheter tube is inserted sufficiently into the canal, vessel, passageway, body cavity etc.

FIG. 11 shows an axially exploded view of a catheter assembly 210 according to the present invention. FIG. 12 shows an external view of the catheter assembly 210 in a sealed configuration. The catheter assembly 210 comprises an external housing 212, a wetting agent storage chamber 228 and a catheter 216. The external housing 212, wetting agent storage chamber 228 and catheter 216 are concentrically arranged such that the catheter 216 is located within the storage chamber 228 which is located within the external housing 212 in a radially nested configuration.

The external housing 212 comprises a main body 218 in which at least a portion of the storage chamber 228 and catheter 216 are housed, and a cap 220 which is detachable so as to be removed by a user prior to use. Removal of the cap 220 exposes the catheter 216 for withdrawal from the external housing 212 for use.

The main body 218 may further comprise a catheter tube section 219 and a storage chamber section 221. The catheter tube section 221 houses the catheter tube 232 of the catheter 216. The storage chamber section 221 houses the storage chamber 230. The catheter tube section 219 and storage chamber section 221 may comprise separate components which are attached together to provide the main body portion 218, or may be provided by parts of a unitary structure. It will be appreciated that portions of the storage chamber section 219 may house portions of the catheter tube 232 and catheter tube section 221 may house portions of the storage chamber 228. Typically, the catheter tube section 221 will provide the terminal proximal end of the housing 212.

The external housing 212 provides an enclosed volume in which the catheter 216 can be housed for storage and transportation prior to use. The main body 218 and cap 220 may provide a sterile cavity in which the catheter 216 is located. The external housing 212 is generally elongate having a longitudinal axis 222 which can be taken to be the principal axis of the catheter assembly 210 which is coaxial with the longitudinal axis of the storage chamber 228 and catheter 216.

The enclosed volume provided by the external housing 212 is defined by an external wall of the housing 212 which extends from a first proximal end 213, which receives an insertion end 224 of the catheter 216, to a second distal end 215 in which a catheter outlet end 226 is received. In the embodiment shown, the second end 215 is provided by the cap 220. Thus, the removal of the cap 220 exposes the outlet end 226 of the catheter 216 such that a user can grip and remove the catheter 216 from the housing 212 for use.

The external profile of the housing 212 can be any required for aesthetic or functional purposes and may incorporate similar external features to the external housing 12 described above. Hence, the external housing 212 may be generally cylindrical, tapering towards the first end to aid insertion into a storage receptacle or pocket, for example, and tapering towards the second end along the length of the cap 220. Additionally, the cap 220 may be temporarily stored on the opposing end of the external housing 212 as shown in FIGS. 2a to 2c.

A hermetic seal may be provided between the cap 220 and main body 218 to preserve the sterility of the internal volume of the external housing 212, prior to use. The hermetic seal may comprise a sealing element, such as an O-ring seal 297b provided between the main body 218 and cap 220 as best seen in FIG. 13, in which case the O-ring seal sits on a circumferential sealing surface on the outside of the main body 218, which, when the cap 220 is sealed faces a corresponding circumferential sealing surface on the inside of the cap.

In an alternative, a hermetic seal may be provided by a tamper proof connection or strip between the main body 218 and cap 220. An example of a hermetic seal 297a formed as a tamper proof strip is provided in FIG. 12. The seal 297a comprises a portion of the external surface of the external housing 212. As such, the external housing 212 may comprise a main body 218, a cap 220 and a hermetic seal 297a. The hermetic seal 297a/b may be configured such that rotating cap 220 breaks the seal 297a. Breaking the seal 297a/b may be done during a priming step which puts the catheter assembly into a primed configuration.

The storage chamber 228 provides a reservoir for the storage of a wetting agent prior to the wetting of the catheter tube 232. The storage chamber 228 is provided at a distal end of the catheter tube 232 such that the catheter tube 232 may be drawn through wetting agent retained within the storage chamber 228 when the catheter is being withdrawn from the housing 212. Alternatively or additionally, upon opening the storage chamber 228, the wetting agent may flow down the exterior surface of catheter tube 232 (which as in the previous embodiment may be functionalised so as to be hydrophilic) towards the closed end of the main body 218

Figure 13:
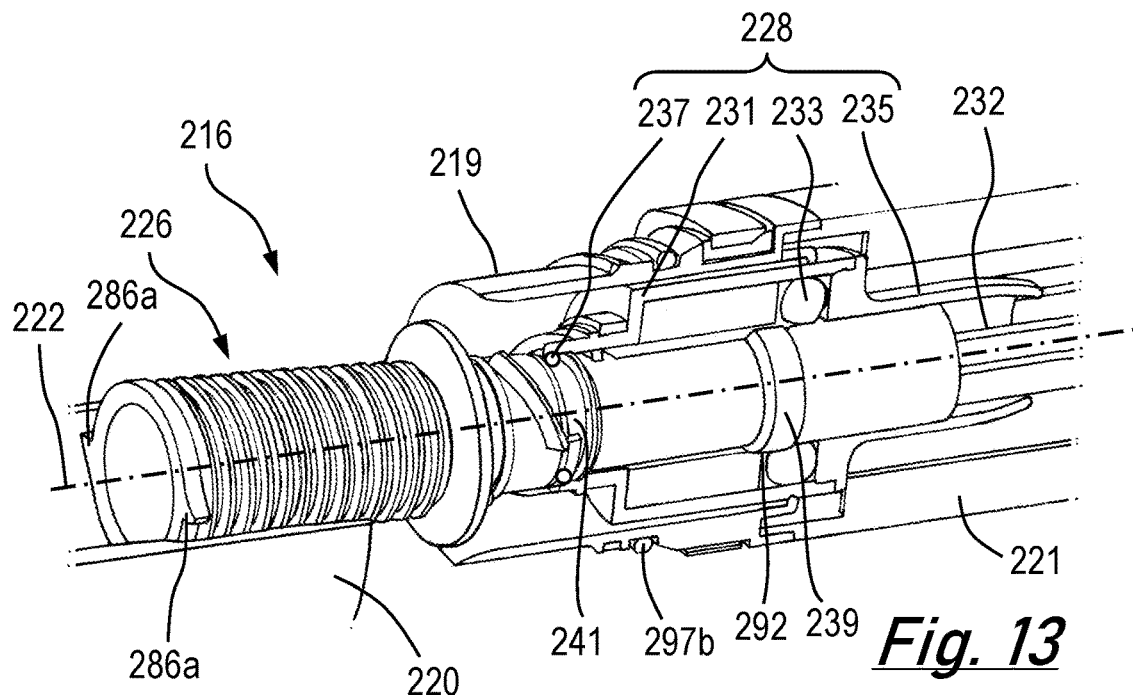
FIG. 13 shows a partial cross-sectional view of the catheter assembly of FIG. 11 showing a wetting agent storage chamber.

Referring to FIG. 13 the storage chamber 228 surrounds the catheter 216 and comprises a chamber wall 231, 235 which seals against seal surfaces 239, 241 provided on the catheter 216 and provides an annular enclosed volume in which the wetting agent is stored prior to use. The storage chamber wall 231, 235 is sealed against the catheter 216 using first and second seals 233, 237 which are axially separated and may be provided at the distal and proximal ends of the storage chamber 228. As the catheter 216 seals the storage chamber 228, it may be considered to form part of the storage chamber 228.

The catheter 216 therefore comprises, a movable insert such that it can be moved relative to the storage chamber wall 231. The catheter 216 may be configured such that it is axially movable when rotated. The rotation of the catheter 216 may be achieved by via rotating the cap 220. As such, the cap 220 and catheter 216 may be rotatably engaged.

The chamber wall 231, 235 may comprise multiple components which are joined together to provide a sealed external wall to provide the enclosed volume which is sealed against the catheter 216.

The storage chamber section 219 may be configured to prevent relative rotation of the storage chamber 228. Thus, when the catheter 216 is urged to rotate within the storage chamber 228, the storage chamber section 219 prevents the storage chamber 228 from rotating about the longitudinal axis 222. As such, the catheter 216 which passes through the storage chamber 228 can be rotated relative to the housing 212 and storage chamber 228 during a release and/or wetting procedure.

The storage chamber section 219 may also be configured to prevent axial movement of the storage chamber 228 during a release and/or wetting procedure. The axial retention of the storage chamber 228 may be limited to be below a predetermined threshold such that when an axial pulling force above the predetermined threshold is achieved, the storage chamber 228 is released from the housing 212 and able to move axially.

As can be seen from FIG. 13, the storage chamber 228 may be an elongate structure which extends coaxially along the longitudinal axis 222 to define an annular cavity in which the wetting agent may be stored. The annular cavity is defined by a radially outer wall with axially facing end walls which extend between the radially outer wall and catheter 216. The end walls may extend from the ends of the radially outer wall in the normal plane of the longitudinal axis 222, but this is not a limitation and other configurations are envisaged. The end walls may comprise or terminate at the radially inner edge in axially extending annular flanges at either or both ends of the storage chamber. An embodiment of these is described in further detail below.

As noted above, the movable insert is configured to move axially along the longitudinal axis 222 with respect to the chamber wall 231. The movement of the catheter 216 may transition the catheter 216 between a first position and a second position. In the first position the storage chamber 228 is sealed by the seal element 233a located between the chamber wall 231 and the catheter 216. The seal element 233a is aligned with sealing surfaces 233b in the first position. In the second position the sealing element 233a is configured to be axially misaligned with at the sealing surface 233b. In this way, the seal 233 can be opened in the second position, or as described below, the compression of the seal element 233a can be reduced such that the storage chamber 228 remains sealed, but the catheter 216 may be withdrawn more readily to effect the wetting of the catheter tube 232. Although the seal element 233a and sealing surface 233b are shown as being placed on the chamber wall 231 and catheter body 243 respectively, this may not be the case and they may by the other way round.

The first and second seals 233 and 237 are axially separated and seal against a portion of the catheter 216. At least one of the movable insert, e.g. the a portion of the catheter 216, and the chamber wall 231 may comprise a divergent portion over which the seal element 233a passes when transitioning between the first sealed position and second primed position. The divergent portion is such that the distance between the chamber wall 231 and movable insert at the axial location of the seal element 233a is increased when in the second primed position. The distance may be a radial distance with respect to the longitudinal axis 222. The divergent portion may comprise a widening of a cavity adjacent to the seal surface 233a. The divergence may be provided by a step or taper adjacent to the sealing surface.

Figure 14A:
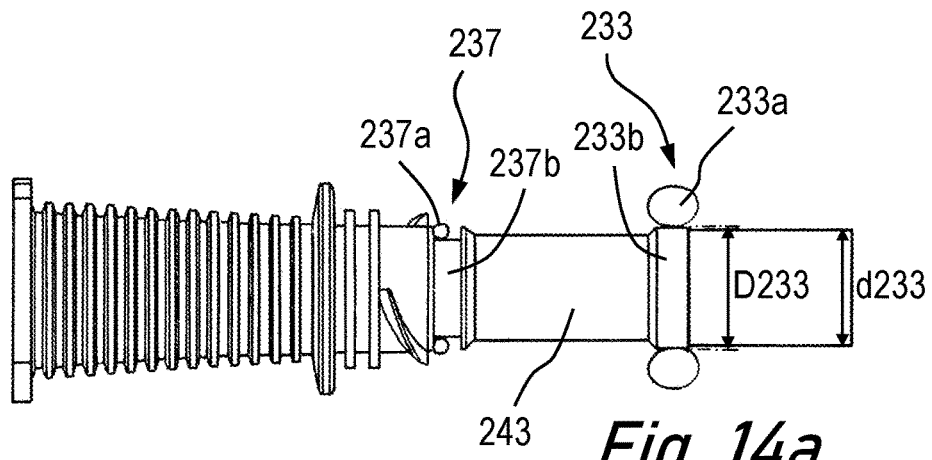
FIGS. 14a and 14b show schematic longitudinal sections of the catheter assembly of FIG. 13 in a sealed and primed configuration respectively.
Figure 14B:
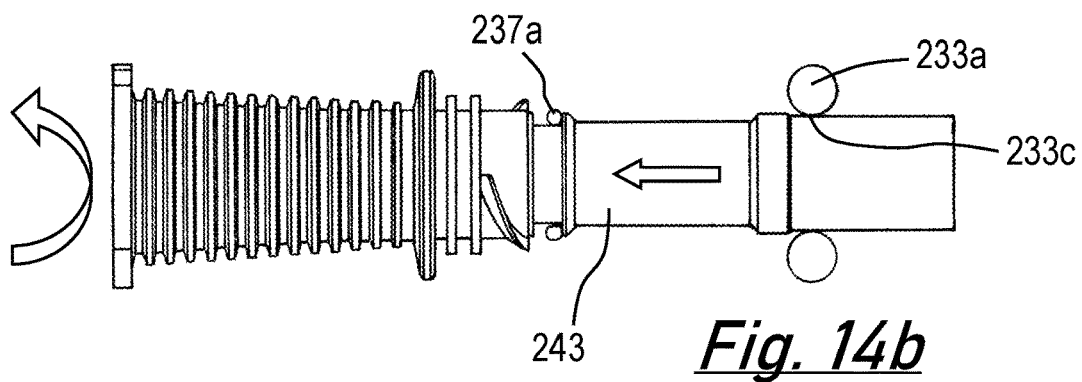

FIGS. 14a and 14b show a side view of the catheter 216 with the first 233 and second 237 seals shown in section. FIG. 14a shows the position of the catheter 216 in a sealed/storage configuration, FIG. 14b shows the catheter 216 in a primed configuration. The primed configuration is one in which the catheter 216 is configured to be removed from the external housing during a second stage of the catheter 216 deployment, (the first stage being the priming).

With reference to FIGS. 13, 14a and 14b, the first 233 and second 237 seals may be provided by respective seal elements 233a and 237a which are located against an opposing seal surface 233b and 237b on the catheter 216. The sealing surfaces 233b and 237b may be considered to be primary sealing surfaces.

In the described embodiment, the seal surfaces 233b and 237b are provided by a catheter body 243. The body 243 thus constitutes the moveable insert and is provided between the outlet end 236 of the catheter 216 and the catheter tube 232. As shown, the catheter body 243 may have an increased radius compared to the catheter tube 232 and is profiled to provide the seal surfaces 233b and 237b.

The catheter body 243 may extend to the distal end of the catheter 216 and be an extension thereof. The distal end of the catheter body 243 may provide the outlet of the catheter 216 which may be shaped externally and internally to provide the external handling surfaces and internal flow enhancing features. Hence, the exterior of the catheter body 243 may include an external handling surface which includes a plurality of grooves which aid the handling of the catheter by a user's finger tips. The internal surface may also include a funnel which diverges in a flow direction. These features of the catheter 216 have been described in connection with FIGS. 1 and 3 and will not be described further here.

The first seal surface 233b is provided at a proximal end of the catheter body 243 and storage chamber 228 and provide a raised portion against which the seal element 233a resides when in a sealed configuration. The raised portion includes a first diameter D233 which is greater than a diameter d233 on an adjacent portion of the catheter body 243 on proximal side and, optionally, distal side. As such, the sealing surface 233b is separated by a step or chamber in the profile of the catheter body 243.

In the example shown, the seal surface 233b and adjacent portion are shown as being cylindrical. Hence, the seal surface 233b comprises a cylindrical surface having a first radius with the adjacent proximal surface being provided by a second radius which is smaller than the first radius. Thus, as shown by FIG. 14b, relative axial movement between the catheter 216 and the seal element 233a which is retained by the storage chamber 228 moves off the seal surface 233b over the proximally adjacent surface defined by diameter d233, there is either: a separation between the seal element 233a and adjacent surface or a reduced contact which allows the storage chamber to be sealed but the catheter more readily withdrawn. As shown in FIG. 14b, the seal contact is maintained with the compressive force, and thus axial retention, on the catheter body 243 and catheter 216 being reduced. In this regard, the proximal shaft of the catheter body 243 may provide a secondary proximal seal surface 233c. Hence, in the sealed configuration the seal 233 may act to provide an increased sealing pressure which can help reduce the evaporation loss from the storage chamber 228.

The distal seal 237 comprises a distal seal element 237a which is sealably located against a seal surface 237b provided by the catheter body 243. In contrast to the proximal seal 233, the distal seal surface 237b is provided by a constant cross-section such that a constant seal 237 is maintained when there is relative axial movement between the catheter 216 and storage chamber 228.

As shown, the distal seal surface 237b may be defined by radial upstands which locate the seal element 237a with a defined axial range of the catheter body 243. The radial upstands may be provided as part of a groove within a surface of the catheter body 237, one or more flanges, or an increase in the diameter of the catheter body 243. FIGS. 14a and 14b show a distal sealing surface 237b having a combination of a radial flange being provided on the righthand, proximal, side, an increase in diameter being provided on the left hand, distal, side, with the seat of the seal surface 237b being provided as a groove in the surface of the catheter body 243 shaft which extends between the first 233 and second seals 237.

As can be seen in FIGS. 13 and 14b, when the catheter 216 is moved distally so as to be withdrawn from the housing 212 (as indicated by the arrow in the centre of the catheter body 243), the distal seal element 237a is retained by the radial upstand so as to be retained around the catheter body 243. The proximal seal element 233a is retained by the storage chamber 228 as the catheter is withdrawn.

It will be appreciated that the storage chamber 228 may comprise features to retain the seal elements 233a and 237a in place and urge the seal elements 233a and 237a radially inwards to provide the seal. For example, the seals 237a and 233a may be retained by a seal housing and may be overmoulded. A specific embodiment pertaining the retention of seal element 233a is provided below in connection with FIG. 16a.

The seal elements 233a and 237a may be different sizes. More specifically, the proximal seal 233 may comprise a larger seal element 233a to allow for the increased compression and increased contact area with the sealing surface 233b when in the first sealed configuration.

The seal elements 233a and/or 237a may comprise an elastomeric material. The seal elements 233a and 237b may be O-rings. Alternatively, the seal elements 233a and 237b may be X-rings or U-cup seals.

The catheter 216 is configured to move axially relative to the external housing 212 and storage chamber 228. This not only allows the catheter 216 to be withdrawn from the external housing 212 for use, but also allows the catheter tube 232 to pass through the wetting agent housed in the storage chamber 228. Thus, the catheter 216 has a sealed (or storage) configuration and a primed configuration from which the catheter 216 is withdrawn and wetted. The sealed configuration of the catheter assembly 210 and catheter 216 is shown in FIGS. 2 and 14a respectively. As described above, the primed configuration prior to the withdrawal of the catheter 216 is shown in FIGS. 13 and 14b.

The movement of the catheter 216 from the sealed configuration to the primed configuration may be achieved by a user axially withdrawing the catheter 216 in the distal direction. The withdrawal may be achieved by the user gripping the outlet end 226 of the catheter either directly, or indirectly, for example, via the cap 220.

The axial withdrawal may be achieved using an actuator. The actuator may be referred to as a priming mechanism. The priming mechanism comprise any device which can cause the required axial movement of the catheter 216 in relation to the external housing 212 and storage chamber 228. In some embodiments, the priming mechanism may comprise the catheter which is configured to be rotatable such that the rotating induces the axial movement. The priming mechanism may comprise a cam drive or crank in which a drive surface engages with a drive element such that relative rotation of the driving element or drive surface results in the axial motion of the catheter 216 relative to the main body 218. The rotational movement may be provided by a rotatable actuator such as the cap 220 which may be rotationally engaged with the catheter 216 as the movable insert.

Figure 15:
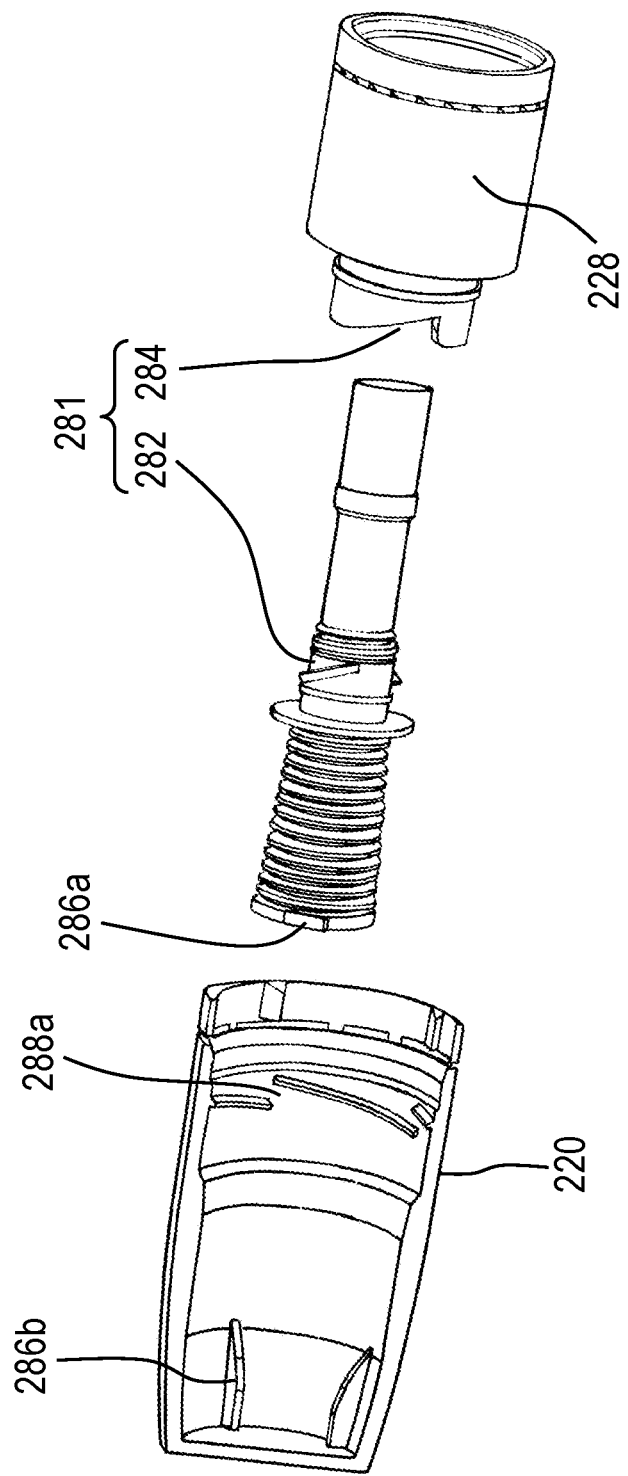
FIG. 15 shows a longitudinally exploded view of a rotatable actuator, storage chamber and movable insert according to an embodiment.

FIG. 15 shows an embodiment in which the catheter body 243 is provided with a cam drive 281. The cam drive comprises a drive surface in the form of a ramp formation provided by an axially facing end wall surface of the storage chamber wall 231, and a driving element comprising circumferentially extending fins 282 which extend axially and circumferentially so as to provide a helical projection which is functions as a screw thread/cam. The fins 282 engage with the corresponding ramp formations 284 provided on the storage chamber 228 such that rotating the catheter 216 causes the fins 282 to travel along the ramp formations 284 and urge the catheter 216 distally relative to the storage chamber 228.

Urging the catheter 216 distally results in an axial sliding of the catheter 216 relative to the storage chamber seals 233 and 237 and the movement of the proximal seal element 233a and the associated seal surface 233b, as described above in relation to FIGS. 14a and 14b.

The rotation of the catheter 216 may be achieved by the user gripping and rotating the external handling surface of the catheter outlet end 226, or via a rotation of the cap 220. Rotating the cap 220 may be achieved by providing a rotational engagement between the cap 220 and the catheter body 243.

As can be seen in FIGS. 13 and 15, the rotational engagement may be provided via corresponding radial projections 286a and 286b on the catheter body 243 and the interior of the cap 220. The projections may take any suitable form and may comprise radially extending members in the form of ribs, flanges, projections, pins, pedestals etc. as noted above, the projections may serve a dual purpose, also assisting in retaining the cap 220 on the base of the main body 218 during catheterisation.

With reference to FIGS. 11 and 15, the cap 220 is also shown as comprising screw threads 288a which engage with corresponding screw threads 288b provided on the exterior of the distal end of the main body 218 such that the cap 220 can be releasably attached to the main body 218.

As the catheter 216 rotationally engages with the cap 220, rotating the cap 220 for removal from the main body 218 via screw threads 288a and 288b, results in the catheter 216 rotating and being withdrawn from the storage chamber 228 via the cam drive 281. Thus, rotation of the cap 220 with respect to the main body 218 results in a rotation of the catheter 216. It will be appreciated from this, that the pitch of the cam-drive ribs/ramp formations will be the same as the pitch of the screw threads 288a,b.

Once the rotation of the cap 220 is complete such that the screw threads 288a,b are disengaged, the cap 220 can be removed axially off the main body 218 with the projections 286a and 286b becoming axially separated. Once the rotation of the catheter 216 is complete, the fins 282 travel circumferentially over the end of the ramp formations and no further axial movement occurs.

Although the priming mechanism shown in FIG. 15 comprises a plurality of helical fins 282, e.g. two, which engage with a corresponding number of ramp formations 284 on the storage chamber 228, it will be appreciated that the number of the drive surface/driving elements may be varied. Further, the helical surfaces which provide cam-like action may be provided by any suitable formations and the embodiments of fins and ramp formations are only provided as examples. For example, both storage chamber 228 and catheter 216 could be provided with ramp formations and/or fins, or some combination thereof. Other cam-like arrangements which translate rotational movement into linear axial movement may be provided, such as screw threads similar to those provided for the engagement of the cap 220 and main body 218.

Figure 16A:
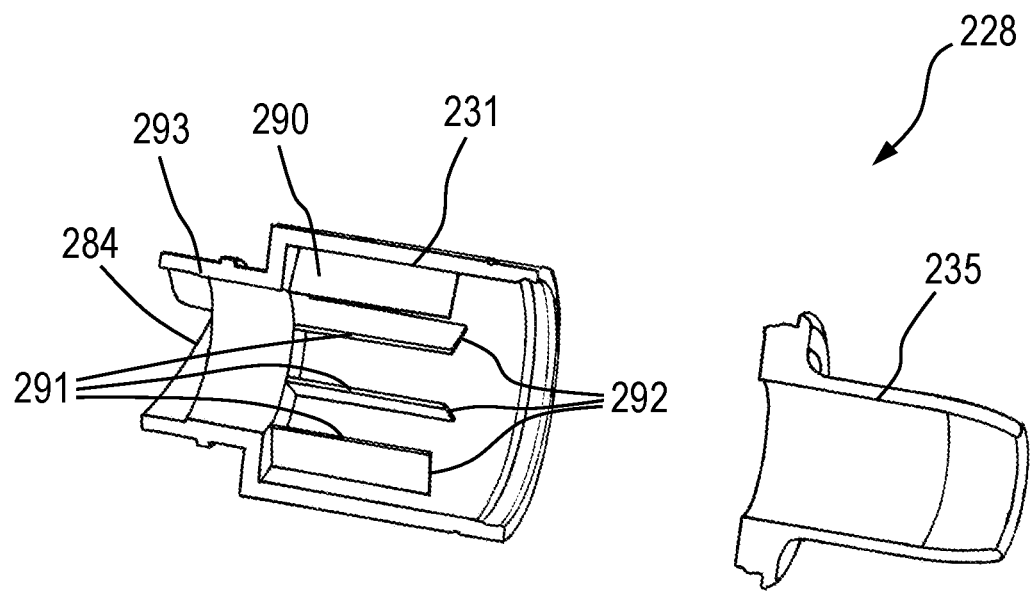
FIGS. 16a and 16b show a storage chamber according to an embodiment.
Figure 16B:
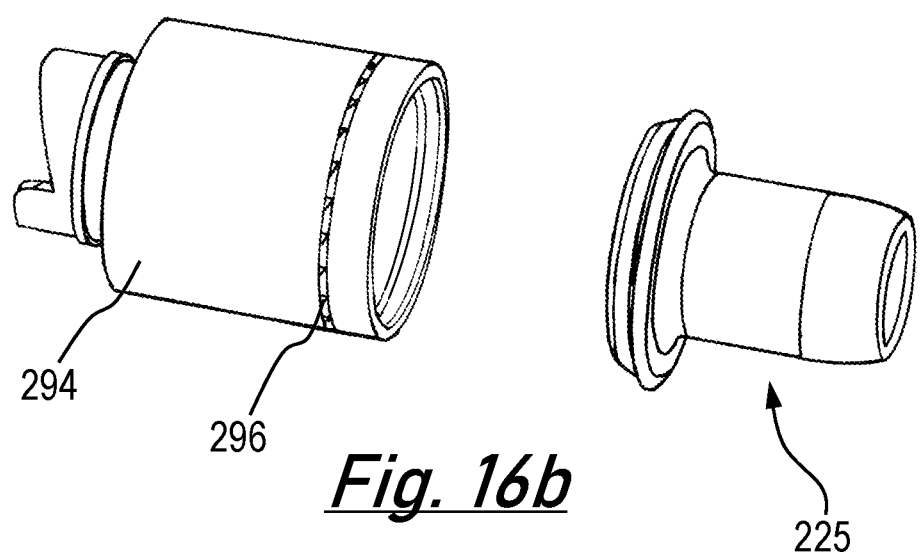

FIGS. 13, 16a and 16b show an embodiment of how the storage chamber 228 may be constructed in more detail. Thus, there is shown a storage chamber 228 provided by multi-part construction in which a first part 231 and a second part 235 are joined together to provide the storage chamber wall. FIG. 13 shows the two-part construction in which the first distal part 231 is fitted to a second proximal part 235. The proximal part 235 comprises a radially extending wall which provides the terminal axial end wall of the storage chamber compartment in which the majority of the wetting agent is located. The distal part 231 comprises a distal end wall of the storage chamber compartment and the radially outer wall.

The internal surface of the storage chamber wall comprises a plurality of radial projections in the form of fins 290. The fins 290 are circumferentially distributed so as to be angularly separated from one another about the longitudinal axis 222. The fins 290 extend axially and radially so as to lie in a plane defined by the longitudinal axis 222 of the catheter assembly. The fins 290 may be provided in diametrically opposed pairs.

As can be seen, the radially inner edges 291 of the fins 290 may be provided at a common radial distance from the central longitudinal axis 222 of the catheter 216 such that, in combination, the radial inner edges 291 of the fins 290 provide a guide tube to keep the catheter 216 and storage chamber 228 concentrically aligned. The radius of the guide tube may correspond to or be larger than the proximal sealing surface 233b such that the sealing surface 233b can pass unhindered therethrough whilst maintaining concentricity.

The proximal axial edges 292 of the fins 290 which define the axial extent of the fins 290 may terminate short of the proximal end wall of the storage chamber 228 so as to provide edges 292 which define a void in which the proximal seal element 233a can be provided. Thus, the proximal axial edges 292 of the fins 290 provide, in combination, a seat against which the seal element 233a can be located during assembly of the storage chamber 228 and also during use such that the proximal seal is axially restrained during the transition of the catheter 216 from the stowed position to the wetting position and during the withdrawal of the catheter 216.

Although FIG. 16a shows only four fins 290 in the sectional view, it will be appreciated that a fewer or greater number of fins 290 may be used. It will also be appreciated that although fins 290 provide a convenient structure between which the wetting agent can be stored whilst providing suitable strength and surface area for guiding the catheter and/or providing a seal seat, other formations may be used. For example, the formations may be provided by any combination of projections such as ribs, pins, pedestals or flanges for example.

As noted above, the distal end of the storage chamber 228 may be provided with one or more features which are used as part of a priming mechanism 281. Thus, as can be seen, the distal end of the storage chamber 228 in FIGS. 16a and 16b comprises the ramp formations 284 which engage with the helical fins 282 provided on the catheter body 243.

The ramp formations 282 are provided at the terminal end of an annular flange 293 which extends from the main storage compartment. In the embodiment shown, the ramp formations 282 are provided by triangular cut-outs in the annular flange 282, with the hypotenuse of the triangle providing the engaging surface. The use of the annular flange 282 allows the ramp formations to be located in a close radial proximity to the catheter 216 which allows the corresponding fins 282 to be smaller. The annular flange 282 also provides a convenient location for the distal seal 237 which resides between the ramp formations 284 and distal radial wall of the main storage compartment of the storage chamber 228.

The attachment of the first 231 and second 235 parts of the storage chamber 228 can be via any suitable connection such as: an interference fit, e.g. a push-fit or click-fit; by adhesion; welding; screw thread or clamp, for example. The embodiment of FIGS. 13, 16a and 16b is shown as being a click-fit attachment in which the parts 231, 235 are pushed and clicked together such that a circumferential rib is located within a corresponding groove.

The external surface of the proximal part 235 is configured to provide an insertion guide 225. Hence, the external surface may be rounded and/or tapered such that it can be utilised to comfortably locate the insertion guide 225 in the entrance to the urethra.

In more detail, in some embodiments, the insertion guide 225 (which may be referred to as a gripper) may be an annular member located radially outwardly of the catheter tube 232 or catheter body 243 when stowed. The radially outer surface of the insertion guide 225 may be configured to be gripped by a user's fingers and may include one or more surface features, such as annular grooves (not shown) for improving grip and user dexterity.

The insertion guide 225 is configured to remain external to the urethra when the catheter tube 232 is inserted and so is retractable. Hence, the catheter tube 232 can pass through the insertion guide 225 such that the insertion guide 225 moves rearwards to towards the outlet end 226 during insertion. When fully retracted, the insertion guide 225 may abut the distal end of the catheter body 243.

Thus, where the storage chamber comprises an insertion guide 225, the storage chamber 228 complete with insertion guide 225 may be released from the external housing when the catheter 216 is withdrawn.

The general procedure relating to the insertion of the catheter 216 and insertion guide 225 is described previously and not repeated here.

To enable the insertion guide 225 to be correctly placed at the insertion end 226 of the catheter ready for use (as shown in FIG. 11), the storage chamber 228 may be retained within the external housing 212 whilst the catheter 216 is removed and the proximal end of the catheter tube 232 is aligned with the insertion guide 225. In order to conveniently withdraw the insertion guide 225 from the housing 212 with the catheter 216, the catheter arrangement 210 may comprise an optional retractable sheath 234 located radially outside of the catheter tube 232. Alternatively, the insertion guide could simply be pulled out by hand.

Figure 19:
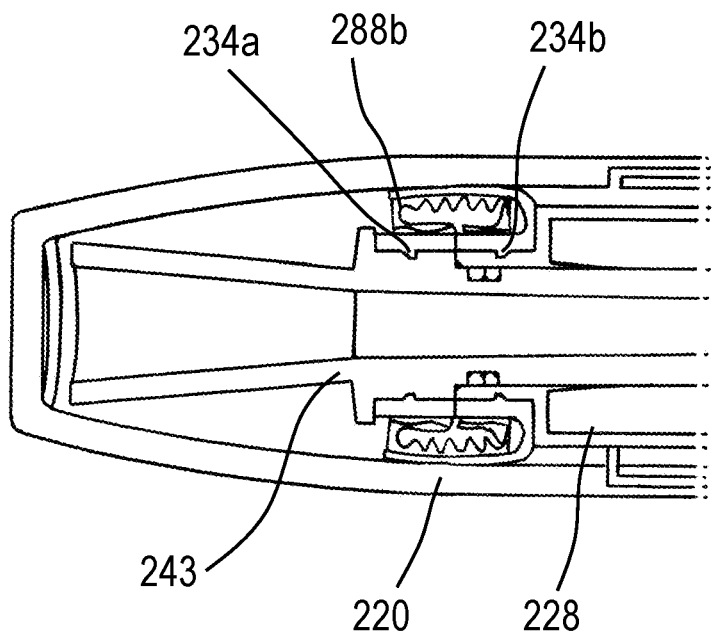
FIG. 19 shows a partial longitudinal sectional view of a retractable sheath in a stowed configuration.

FIGS. 11 and 19 show a retractable sheath 234 in a stowed configuration. The sheath 234 extends from an attachment 234a on the catheter body 243 to an attachment 234b on the distal side of the storage chamber 228. The sheath 234 is flexible and retractable with the insertion guide 225. Hence, when the catheter 216 and insertion guide 225 are located within the housing 212, the sheath 234 is provided in a stowed configuration which is depicted in FIG. 11, and when the catheter 216 is withdrawn, the sheath unfurls from the stowed configuration to a deployed configuration in which it is fully extended and acts to tether the storage chamber to the catheter such that a continued withdrawal of the sheath 234 results in the withdrawal of the storage chamber and insertion guide 225.

It will be appreciated that, in embodiments where an insertion guide 225 is not provided, the storage chamber 228 may not comprise the proximal annular flange which forms part of the proximal part 235, and may not be retained within the housing 212 when the catheter 216 is removed. In such a case, the sheath 234 may also be omitted.

Figure 18:
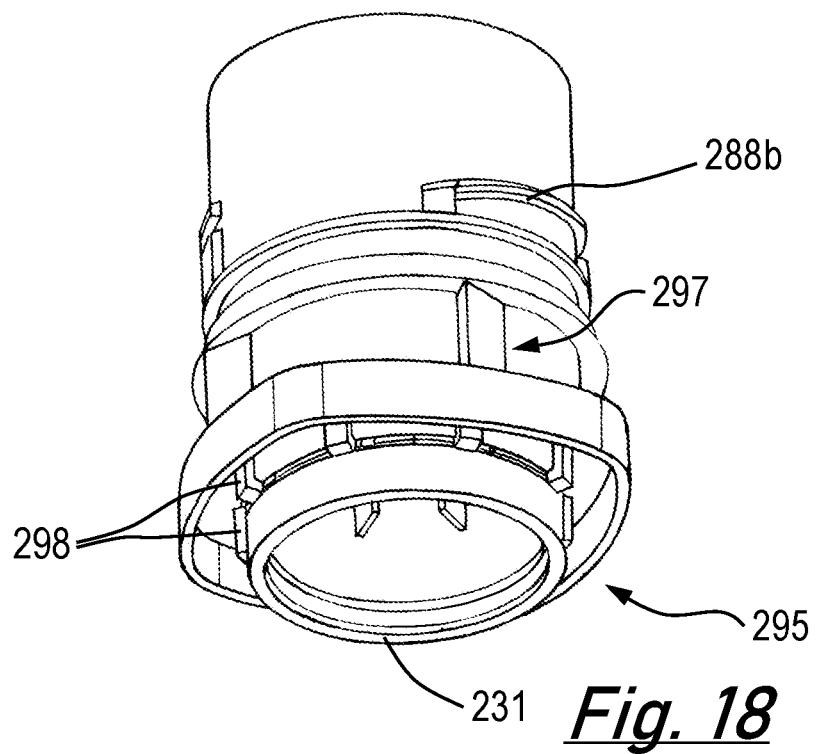

To enable its removal, the storage chamber 228 may be retained within the external housing 212 by a releasable coupling 295, (as best seen in FIG. 18 and described below). The releasable coupling 295 may release the storage chamber 228 when a predetermined amount of axial tension, i.e. a withdrawing pulling force on the storage chamber is applied or exceeded. Once the predetermined amount of axial tension has been applied or exceeded, the storage chamber may be released by the releasable coupling and withdrawn from the external housing.

The axial tension may be applied to the storage chamber 228 directly or indirectly. Thus, in some embodiments, a user may grip the storage chamber 228 or a portion thereof and withdraw it, together with the catheter 216. In some embodiments, the storage chamber 228 and catheter 216 may be coupled together such that withdrawing of the catheter 216 causes the storage chamber 228 to be withdrawn from the external housing 212. In some embodiments, the coupling between the storage chamber and catheter may be provided by a tether such as the retractable sheath 234.

Figure 17:
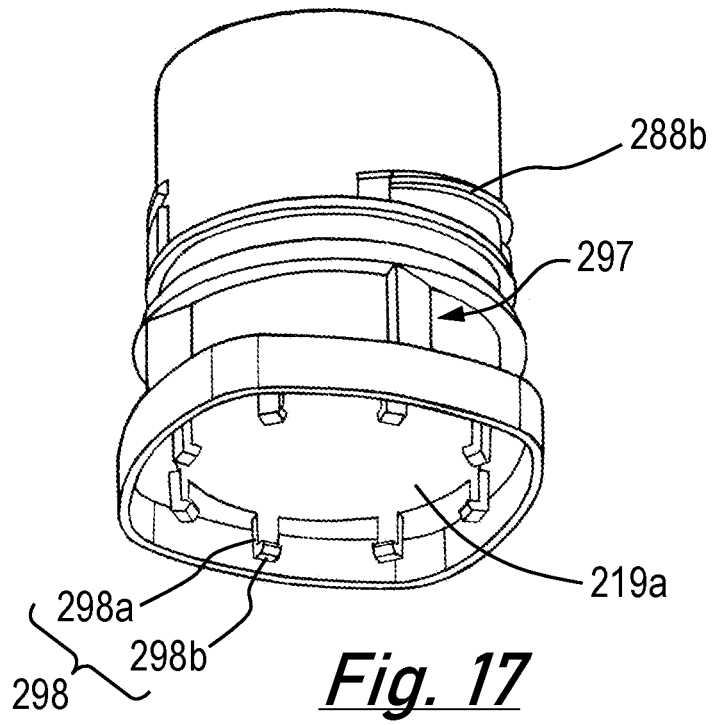
FIGS. 17 and 18 show an example of a storage chamber and releasable coupling.

To prevent the rotation of the storage chamber 228 with the catheter 216 during the transition between the sealed configuration and the primed configuration, the storage chamber 228 may be rotationally fixed to the main body 218. An embodiment of a coupling 295 configured prevent relative rotation is described in connection with FIG. 16b, which shows the exterior of the storage chamber 228; FIG. 17, which shows the storage chamber section 219 without the storage chamber 228 housed therein; and FIG. 18 which shows the storage chamber 228 and storage chamber section 219 combined. As described below, the coupling 295 may be configured to be a releasable coupling, such that the coupling 295 is released once a predetermined force threshold is exceeded in the axial direction.

The exterior of the storage chamber 228 may be provided by an external surface 294 which, in the described embodiment, is generally cylindrical. The external surface 294 may comprise one or more anti-rotation and/or axial retention features such as a one or more recesses. A plurality of circumferential recesses may be provided such those provided by the castellated annular groove 296.

The storage chamber section 219 may comprise an elongate tubular member which extends from proximal end to a distal end. The external surface of the storage member section 219 may provide a portion of the external surface of the external housing 212 and/or one or more features for attaching the cap 220 to the main body 218 such as the aforementioned screw threads 288b, and/or one or more features 297 for receiving a hermetic seal 297a shown in FIG. 11 which may be provided between the corresponding terminal ends of the cap 220 and main body 218 and which is irreversibly removed or broken as the cap 220 is removed, as well known in the art.

The interior of the storage chamber section 219 comprises a cylindrical cavity 219a in which the storage chamber 228 is received and may include one or more features of the coupling 295 for engaging the storage chamber 228 to prevent axial and/or radial movement of the storage chamber 228 relative to the housing 212.

The coupling 295 part provided by the storage chamber section 219 comprises a plurality of circumferentially distributed prongs 298 which are substantially rotationally rigid to the extent where they act in combination to prevent rotation of the storage chamber when engaged in annular castellated groove 296, and radially compliant such that, when the storage chamber 228 and chamber storage section 219 are urged axially apart, the prongs 298 flex outwardly thereby releasing the storage chamber 228. When under the predetermined axial force threshold, the prongs 298 remain engaged with the castellated groove 296 on the external surface 295 of the storage chamber wall.

The number of prongs in FIGS. 17 and 18 is eight. However, the number may be greater or fewer than this in some embodiments.

The castellated groove 296 comprises an annular groove which extends around the external surface 294 of the storage chamber 228 and is partitioned so as to provide and a circular array of recesses in which the tips of the prongs 298 can be received. It will be appreciated that in other embodiments, the recesses may be fewer in number and more dispersed than shown.

The prongs 298 comprise projections having a limb 298a and a tip portion 298b. The limb 298a extends axially towards the proximal end of the main body 218 from a radially extending internal surface of the storage chamber section 219. The limbs 298a extend from a distal fixed end to a proximal free end. The free end includes the tip portion 298b which extends radially inwards to provide hooks which are received in the recesses of the storage chamber external surface 294 so as to provide a clasp. The radially inner surface of the storage chamber section which receives the storage chamber 228 is flush with the internal surface of the cylindrical housing in which the storage chamber is received.

When viewed along the longitudinal axis in the distal direction, the radially inner edge of the proximal end of the prong tip portions 298b are tapered such that prongs 298 can more readily receive and be urged apart by the storage chamber 228 when the storage chamber 228 is inserted into the storage chamber section 219 along the longitudinal axis.

As noted, the releasably coupling requires an increased axial force to activate. The increase in force ensures that the catheter tube is fully withdrawn such that the storage chamber 228/insertion guide 225 is in the correct location relative to the insertion end and that the retractable sheath is fully extended. It may also provide mechanical feedback to the user to indicate that the catheter has been withdrawn to its full extent and can be reinserted if required.

In some embodiments, when the storage chamber 228 is left within the housing 212 following the withdrawal of the catheter 216, the storage chamber 228 may be attached to or form part of the housing 212 and the coupling 295 may not be required.

In use, and with reference to the catheter assembly shown in FIG. 2, a user may rotate the cap 220 to break the hermetic seal 297a/297b. The rotation of the cap 220 results in the rotation of the catheter 216 via the rotational engagement provided by radially projections 286a and 286b. The rotation of the catheter 216 results in the drive surface and driving elements provided by cam drive 281 urging the storage chamber 228 and catheter 216 axially apart and an axial sliding of the proximal seal element 233a to provide the catheter assembly in a primed configuration. This requires a first step in which a single action from a user, i.e. the rotation of the cap 220 in a first direction transitions the catheter assembly from a sealed configuration to a primed configuration.

Following the separation of the seal 233, the catheter 216 may be axially withdrawn through the storage chamber 228 which functionally acts as a wetting chamber during the withdrawal. If required, the catheter may be reinserted into the storage chamber 228 and withdrawn multiple times to ensure a complete wetting of the catheter tube 232 prior to removal.

Where the catheter 216 incorporates an insertion guide 225, the insertion guide 225 may form part of the storage chamber 228 and may be removed from the housing 212 with the catheter 216.

It will be appreciated that the above described embodiments in which the catheter includes a movable insert which is rotated to axially release, either partially or fully, a seal of the storage chamber is advantageous as the mechanical advantage of using a priming mechanism allows the seal to be tighter. Without the mechanical advantage of the priming mechanism, the tighter more effect seal would be difficult to displace by hand, particularly for weaker or more infirm users.

According to a further embodiment of the present invention there is provided a catheter assembly 310.

Referring to FIGS. 20 21a, 21b, and 21c, the catheter assembly 310 comprises an external housing 312 and a catheter 316. The catheter 316 comprises a catheter tube 332 and a sheath 334. The external housing 312 and catheter 316 are concentrically arranged such that the catheter 316 is located within the external housing 312 in a radially nested configuration.

The catheter assembly 310 may be configured such that the catheter 316 may be wetted prior to being withdrawn from the external housing 312. The wetting agent used to wet the catheter 316 prior to use and may be held in a wetting agent storage chamber which is defined between the external housing 312 and a first portion of the catheter 316. The wetting agent may be delivered to the catheter 316 via a wetting chamber which is defined between the external housing 312 and a second portion of the catheter 316. The catheter 316 may be movable and may comprise a movable insert.

Again, referring to FIGS. 20 21a, 21b, and 21c, the external housing 312 comprises a main body 318 in which a portion of the catheter 316 is housed and a cap 320, the cap 320 comprising part of the catheter 316, i.e. remaining integral with the catheter even during catheterisation and release of urine from the body.

The external housing 312 provides an enclosed volume in which the catheter 316 can be housed for storage and transportation prior to use. The main body 318 and cap 320 may provide a sterile cavity in which the catheter 316 is located. The external housing 312 is generally elongate having a longitudinal axis 322 which can be taken to be the principal axis of the catheter assembly 310. In this embodiment, axial or radial should be taken to be with reference to the longitudinal axis 322 unless stated otherwise.

The enclosed volume provided by the external housing 312 is defined by an external wall of the housing 312 which extends from a first proximal end 313, which receives an insertion end 324 of the catheter 316, to a second distal end 315 in which a catheter outlet end 326 is received. In the embodiment shown, the second end 315 is provided by the cap 320, which comprises part of the catheter 316, and the outlet end 326. The cap 320 may provide an external handling surface with which a user may withdraw the catheter 316 from the main body 318.

The external profile of the housing 312 can be any required for aesthetic or functional purposes and, in the example shown, is generally cylindrical, tapering towards the first end to aid insertion into a storage receptacle or pocket, for example, and tapering towards the second end along the length of the cap 320.

The cap 320 comprises an open-ended generally cylindrical body having a circumferential external wall which extends coaxially along the longitudinal axis 322, being open at both ends. The cap 320 mates with the distal end of the main body 318, such that the cap 320 is received within the open distal end of the main body 318. However, it will be appreciated that the cap 320 could receive an open end of the main body 318 in some embodiments.

The external housing 312 may be used to transport the catheter 316 ready for use and also to dispose of the catheter 316 following use.

Figure 22A:
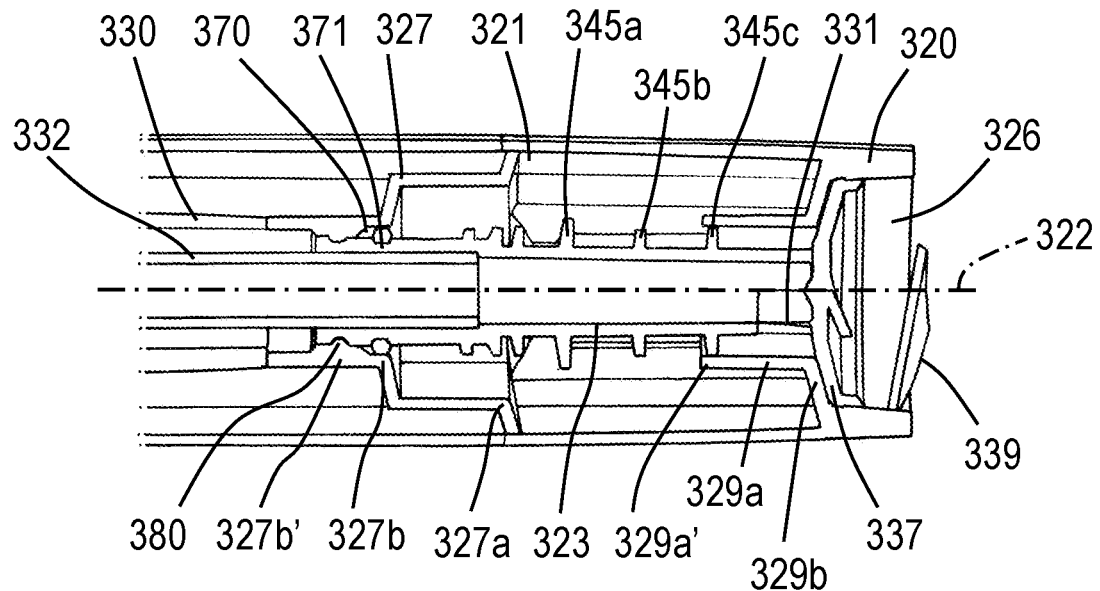
FIG. 22a shows a cross sectional view of the wetting mechanism of the catheter assembly of FIG. 20 in a closed configuration.
Figure 22B:
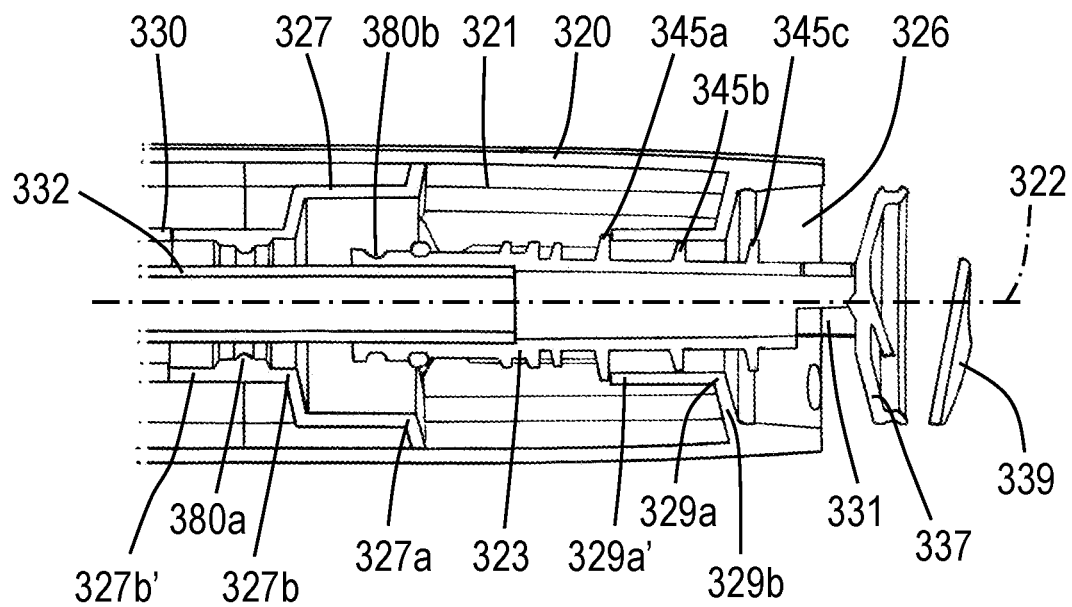
FIG. 22b shows a cross sectional view of the wetting mechanism of the catheter assembly of FIG. 20 in an open configuration.

With reference to FIGS. 20, 22a and 22b, the cap 320 may provide an enclosure which defines a wetting agent storage chamber 321 for a wetting agent (not shown). The wetting agent storage chamber 321 is formed between the cap 320 and a moveable insert which, in this embodiment, is provided by a connector 323 which comprises a part of the catheter 316, connecting the catheter tube 332 to the catheter outlet 326, as will be described in detail below. Thus, the connector 323 may be provided within the external housing 312 in a spaced relation so as to define a cavity 321 therebetween.

The axial bounds of the wetting agent storage chamber 321 may be defined by a first 327 and a second 329 radially projecting wall projecting in from an inner wall of the cap 320. The first wall 327 may be arranged closer to the insertion end 324 of the catheter 316 than the second wall 329, which may be arranged proximate to the second distal end 315 of the main body.

The first 327 and second 329 walls may comprise one or more steps. As illustrated in FIGS. 22a and 22c, the first wall 327 is formed as a separate component to the remainder of the cap 320, and comprises two steps, a first step 327a and a second step 327b; the second step 327b arranged radially inwards and axially toward the insertion end 324 of the first step 327a. Both steps in the first wall comprise a first section projecting radially inwards and a second portion extending axially towards the insertion end 324, thus forming two tubular sections, arranged coaxially with the cap 320. The second tubular section 327b' may form a first sealing surface 327b' for sealing the wetting agent storage chamber 321 (described in detail below). The second wall 329 may comprise one or more steps. As illustrated in FIGS. 22a,b, the second wall 329 comprises a single step, with a first portion 329a projecting radially inwards from the inner wall of the cap 320 and the second portion 329b extending perpendicular to the first portion 329a and axially towards to the insertion end 324 so as to form a tubular section arranged co-axially and radially inwards to the cap 320. The second portion 329b of the second wall may form a second sealing surface 329b for sealing the wetting agent storage chamber 321 (described in detail below). The cavity may be referred to as a wetting agent storage chamber 321 or a reservoir 321.

The wetting agent storage chamber 321 is sealed in a first configuration (as shown in FIG. 22a) such that the wetting agent is retained therein, and open in a second configuration (as shown in FIG. 22b) such that the wetting agent can flow out of the wetting agent storage chamber 321 and contact the catheter tube 332. When in the open configuration, the internal volume of the wetting agent storage chamber 321 may be in fluid communication with a wetting chamber 330 in with the catheter tube 332 is located such that the wetting agent can flow from the wetting agent storage chamber 321 to the wetting chamber 330 and thus to the catheter tube 332.

With reference to FIGS. 22a,b, the connector 323 is radially nested within the cap 320, the two components defining the wetting agent storage chamber 321. The connector 323 may comprise a tubular wall which is configured to define a portion of the wetting agent storage chamber 321 on a radially outer side thereof and a portion of the drainage path (as described in detail below) on a radially inner side thereof.

The connector 323 may comprise an elongate thin-walled structure which extends longitudinally along the principal axis 322 of the catheter assembly 310. The connector 323 comprises an open first end which is configured to receive the catheter tube 332 and a closed second end proximate to the outlet end 326. The second end of the connector may comprise a drain 331, an end wall 337 and a tab 339 for opening the drain 331. The end wall 337 may be a radially extending, axially facing disk with a first face which closes the second end of the connector 323 and a second face opposite the first. On the second face of the end wall 337 there may be arranged a tab 339 flexibly joined to the end wall 337 in the form of a ring pull. Arranged on the connector 323 proximate to the end wall 337 are one or more apertures which form a drain 331, providing a fluid connection between the interior to the connector 323 and the exterior of the catheter assembly 310.

As previously stated, the connector 323 is located radially within the cap 320, to facilitate this the radially outer surface of the connector proximate to the first open end may be shaped and sized to rest in the second tubular section 327b' of the cap, forming the corresponding part of the first sealing surface. To improve the wetting agent storage chamber seal, a sealing means, such as a sealing element 370 may be provided. In the illustrated embodiment the sealing element is provided in the form of an O-ring 370 arranged on the radially outer surface of the connector, within a recess 371 to restrict the motion of the O-ring 370 relative to the connector 323. It will be appreciated by those skilled in the art that the sealing element may also be provided on the first wall 327, or on both the connector 323 and the first wall 327.

To ensure that the wetting agent storage chamber 321 remains sealed during transport and storage, and to ensure that it is not accidently deployed into the second configuration, the connector 323 and first wall 327 may also comprise a retention mechanism 380. The retention mechanism 380 comprises a retention clip 380a, arranged circumferentially within and projecting radially inwards of the first sealing surface 327b'; and a corresponding groove 380b arranged on the radially outer surface of the connector 323. It will be appreciated that the shape, and optionally, material of the retention mechanism 380 can be selected to ensure the retention mechanism 380 disengages when a predetermined force is applied.

To further facilitate the arrangement of the cap 320 and connector 323, the connector 323 may be provided with a plurality of projecting ribs 345 projecting radially outward about the circumference of the outer surface of the connector. As seen in FIG. 22a,b there are provided three ribs 345, a first rib 345a is arranged approximately half way along the axial length of the connector 323, with the second 345b and third 345c ribs arranged between the first 345 and the drain 331. The first rib 345a extends such that its radial diameter is greater than the radial inner diameter of the second sealing surface 329b. The second 345b and third 345c ribs are configured such that they may slidably move in an axial direction within the second sealing surface.

The combination of a first, larger stop rib 345a and two smaller guide ribs 345b 345c provide a number of functions. Firstly, they provide a seal to prevent wetting agent from leaking from the catheter assembly 310 during storage and transport. Secondly, the guiding ribs 345b,c guide the motion of the connector in and between the sealed configuration (as shown in FIG. 22a) where the third rib 345c is arranged against the second sealing surface 329b and the open configuration (as shown in FIG. 22b) where the second rib 345b is arranged against the second sealing surface 329b. The stop rib 345a limits the extent of the distal axial movement of the connector 323 and catheter tube 332, such that they cannot be moved beyond the open configuration and pulled out of the cap 320.

In use, the user pulls the tab 339, once a predetermined force is applied, the retention mechanism 380 disengages, such that the connector 323 and catheter tube 332 move in a distally axial motion relative to the cap 320 moving the wetting agent storage chamber 321 from the sealed configuration to the open configuration. The O-ring 370 moves axially away from the first sealing surface 327b', breaking the seal of the wetting agent storage chamber 321.

As the connector 323 is moved axially through the cap 320 the alignment is maintained by the second 345b and third 345c ribs, with at least one arranged against the second sealing surface 329b at all times. The extent to which the wetting agent storage chamber can be opened being defined by the first rib 345a contacting the second sealing surface 329b.

Once the catheter 316 is in the open configuration, the wetting agent is released from the wetting agent storage chamber 321 into the wetting chamber 330, wetting the catheter 316, as described below.

Referring to FIGS. 21 and 22a-c, the catheter 316 may be any suitable catheter known in the art. In this embodiment the cap 320 comprises part of the catheter 316, the cap 320 is formed in two parts a top cap 320a which defines the radially outer wall of the wetting agent storage chamber and a bottom cap 327 which forms the first wall 327.

As shown, the catheter 316 also comprises a catheter tube 332.

The catheter tube 332 may be may be an elongate thin-walled structure which extends longitudinally along the principal axis 322 of the catheter assembly 310. The catheter tube 332 may be comprised of a flexible material. A first end of the catheter tube 332 may be closed with a hemi-spherical shape, and form the insertion end 324 of the catheter 316, the hemispherical shape aiding with insertion.

Proximate to the insertion end 324 there may be provided one or more drainage apertures 333 which act as inlets for receiving urine from the patient's bladder. In this embodiment the drainage apertures 333 are oval in shape with the major axis being parallel with the principal axis 322. It will be appreciated that the size and shape of the drainage apertures 333 may differ.

The exterior surface of the catheter tube 332 may be, as outlined in the previous embodiments, functionalised such that when wetted by the wetting agent the co-efficient of friction of the catheter tube 332 is reduced.

The end of the catheter 316 distal to the insertion end 324 is provided with a catheter outlet end 326. In this embodiment the catheter outlet end 326 is provided as part of the connector, in other embodiments they may be a separate component. The catheter 316 is configured to provide fluid communication between the drainage apertures 333 and the drain 331.

FIGS. 20 and 21c and 22a,b also show an optional sheath 334. The sheath is formed of a flexible material and is arranged surrounding the catheter tube 332. The sheath is coupled at a first end to the cap 320 on the first wall 327 thereof, and at a second end to an insertion guide 325. The insertion guide 325, or part thereof, is comprised of an elastically deformable material.

In use, after completing the wetting cycle as described above, the user withdraws the wetted catheter 316 from the catheter assembly 310. Holding the gripping surface of the cap 320, and where present, the insertion guide 325, the user directs the catheter tube 332 into a canal, vessel, passageway, body cavity, etc. for removal of fluid therefrom.

Where the sheath 334 and insertion guide 325 are present, the user grips the insertion guide 325 to guide the catheter tube 332. The user squeezes the insertion guide 325, deforming it such that it engages with the catheter tube 332, restricting axial motion of the catheter tube 332 through the inserter guide 325 and inserts a first section of the catheter tube 332 exposed from within the sheath 334 into the canal, vessel, passageway, body cavity etc. Once the first section of the catheter tube 332 has been inserted, the user relaxes their grip on the insertion guide 325, allowing it to return to its original shape, and slidably draws the insertion guide 325 along the catheter tube 316 away from the insertion end 324, furling a portion of the sheath 334 and exposing a second section of the catheter tube 316. The process is then repeated, with the user squeezing the insertion guide 325 to restrict the motion of the insertion guide 325 with respect to the catheter tube 316 and thereafter the second section of the catheter tube is inserted. The process is repeated until the catheter tube 316 is inserted sufficiently into the canal, vessel, passageway, body cavity etc.

In this embodiment, the catheter 316 is a female urinary catheter 316, with the catheter configured for insertion into a female patient's bladder via the urethra. Upon insertion into the patient's bladder fluid enters the interior of the catheter tube 16 via the drainage apertures 333, flowing through the catheter 316 to and discharged at the drain 326.

Once the bladder is drained the catheter 316 can with withdrawn from the bladder and urethra, placed back within the main body 318 for disposal as outlined above.

The one or more embodiments are described above by way of example only. Many variations are possible without departing from the scope of protection afforded by the appended claims.

For example, whilst the embodiments are all female intermittent urinary catheters, with an exemplary length of between 90 mm to 200 mm. e.g. between 130 mm and 155 mm, such as about 135 mm and the catheter assemblies have a length corresponding to the length of the catheter, such as a closed length of the casing of between 2 mm and 10 mm longer than the length of catheter (e.g. 10-25 cm; between 140 mm and 165 mm, such as 142 mm), it is considered that teachings could be applied to male urinary intermittent catheters (which are typically longer) or even other types of catheter. Similarly, although the embodiments have functionalised hydrophilic surfaces which become slippery when wetted with a wetting agent such as water, the wetting agent could be a lubricant instead.

The invention claimed is:

1. A catheter assembly comprising:
   a catheter having a distal outlet end and a proximal insertion end;
   a wetting agent storage chamber;
   an external housing, the external housing at least partially enclosing the catheter and the storage chamber; and,
   a sheath connected between the catheter and the storage chamber such that withdrawing the catheter from the external housing causes withdrawal of the storage chamber from the external housing via the sheath;
   wherein the sheath is deployable from a stowed configuration in which the sheath is furled completely between the outlet end and storage chamber, to an extended configuration in which the sheath is unfurled and contains a catheter tube of the catheter located therein.

2. The catheter assembly of either of claim 1, wherein the catheter and storage chamber are held within the external housing such that a first predetermined force is required to withdraw the catheter from the external housing and a second predetermined force is required to disengage the storage chamber for withdrawal from the external housing.

3. The catheter assembly of claim 1, further comprising an insertion guide configured to move over the insertion end of the catheter for use, the insertion guide comprising an external handling surface and configured to aid the placement of the insertion end at the urethra of a patient, wherein the storage chamber comprises the insertion guide.

4. The catheter assembly of claim 1, further comprising a release mechanism arranged to releasably retain the storage chamber.

5. The catheter assembly of claim 4, wherein the release mechanism comprises a releasable coupling between the external housing and storage chamber.

6. The catheter assembly of claim 5, wherein the releasable coupling comprises one or more projections extending from either or both the external housing and wetting agent chamber, the projections being received in one or more corresponding recesses provided in the other of the external housing and wetting agent chamber.

7. The catheter assembly of claim 6, wherein the catheter assembly comprises an equal number of releasable projections and recesses.

8. The catheter assembly of claim 6, wherein the projections and recesses are configured to remain engaged when subjected to a first predetermined force and configured to disengage when subject to a second predetermined force.

9. The catheter assembly of claim 8, wherein the first and second predetermined forces are axial.

10. The catheter assembly of claim 9, wherein the projections are elongate having a longitudinal axis and are configured to deflect away from the longitudinal axis when the second predetermined force is applied or exceeded.

11. The catheter assembly of claim 10, wherein the catheter is elongate and defines a principal longitudinal axis of the catheter assembly, wherein the longitudinal axis of the projections extend in the direction of the principal longitudinal axis.

12. The catheter assembly of claim 10, wherein the deflection is in a radially outwards direction.

13. The catheter assembly of any of claim 6, comprising a plurality of projections and recesses distributed circumferentially about the principal axis.

14. The catheter assembly of claim 13, further comprising a seal element in the storage chamber and a movable insert received within the storage chamber, wherein the seal element is located between the storage chamber and the movable insert and is radially inwards and axially aligned with the plurality of projections and/or recesses.

15. The catheter assembly of claim 6, wherein the release mechanism is configured to prevent relative rotation of the external housing and wetting agent chamber.

16. The catheter assembly of claim 1 wherein the catheter is provided with a hydrophilic surface.

17. The catheter assembly of claim 1 wherein the catheter has a length of between 90 mm to 200 mm.

18. The catheter assembly of claim 1 wherein the assembly has a length of between 2 mm and 10 mm longer than the length of catheter.

19. The catheter assembly of claim 1 having a length of 10-25 cm.

20. The catheter assembly of claim 1 having a length of between 140 mm and 165 mm.

* * * * *